(12) United States Patent
Bergstein

(10) Patent No.: US 8,846,325 B2
(45) Date of Patent: Sep. 30, 2014

(54) METHODS OF CANCER DIAGNOSIS AND THERAPY TARGETED AGAINST A CANCER STEM LINE

(76) Inventor: Ivan Bergstein, New York, NY (US)

(*) Notice: Subject to any disclaimer, the term of this patent is extended or adjusted under 35 U.S.C. 154(b) by 594 days.

(21) Appl. No.: 12/187,177

(22) Filed: Aug. 6, 2008

(65) Prior Publication Data

US 2009/0011441 A1    Jan. 8, 2009

Related U.S. Application Data

(63) Continuation of application No. 11/271,381, filed on Nov. 10, 2005, now Pat. No. 8,038,998, which is a continuation of application No. 09/468,286, filed on Dec. 20, 1999, now Pat. No. 7,361,336, which is a continuation-in-part of application No. 08/933,330, filed on Sep. 18, 1997, now Pat. No. 6,004,528.

(51) Int. Cl.
| | | |
|---|---|---|
| G01N 33/567 | (2006.01) | |
| G01N 33/574 | (2006.01) | |
| A61K 49/00 | (2006.01) | |
| G01N 33/50 | (2006.01) | |
| C07K 16/30 | (2006.01) | |

(52) U.S. Cl.
CPC .............. C07K 16/30 (2013.01); G01N 33/574 (2013.01); G01N 33/5017 (2013.01)
USPC ............................ 435/7.21; 435/7.23; 424/9.1

(58) Field of Classification Search
None
See application file for complete search history.

(56) References Cited

U.S. PATENT DOCUMENTS

| | | | |
|---|---|---|---|
| 4,894,326 | A | 1/1990 | Matsuura |
| 5,169,835 | A | 12/1992 | Chan |
| 5,300,500 | A | 4/1994 | Lee |
| 5,489,516 | A | 2/1996 | Broudy et al. |
| 5,530,101 | A | 6/1996 | Queen et al. |
| 5,587,458 | A | 12/1996 | King |
| 5,688,657 | A | 11/1997 | Tsang |
| 5,730,982 | A | 3/1998 | Scheinberg |
| 5,808,002 | A | 9/1998 | Buhring |
| 5,843,633 | A | 12/1998 | Yin et al. |
| 5,869,045 | A | 2/1999 | Hellstrom et al. |
| 5,877,299 | A | 3/1999 | Thomas et al. |
| 5,942,602 | A | 8/1999 | Weis et al. |
| 5,980,896 | A | 11/1999 | Hellstrom et al. |
| 5,990,281 | A | 11/1999 | de Sauvage et al. |
| 6,004,528 | A | 12/1999 | Bergstein |
| 6,129,915 | A | 10/2000 | Wels et al. |
| 6,258,939 | B1 | 7/2001 | Reiter et al. |
| 6,506,881 | B1 | 1/2003 | Adair et al. |
| 7,361,336 | B1 | 4/2008 | Bergstein |
| 7,427,400 | B2 | 9/2008 | Bergstein |
| 7,504,103 | B2 | 3/2009 | Bergstein |
| 7,608,259 | B2 | 10/2009 | Bergstein |
| 2001/0055751 | A1 | 12/2001 | Reiter et al. |
| 2007/0036800 | A1 | 2/2007 | Bergstein |
| 2007/0036801 | A1 | 2/2007 | Bergstein |
| 2007/0036802 | A1 | 2/2007 | Bergstein |
| 2007/0036803 | A1 | 2/2007 | Bergstein |
| 2007/0036804 | A1 | 2/2007 | Bergstein |
| 2007/0041984 | A1 | 2/2007 | Bergstein |
| 2008/0305107 | A1 | 12/2008 | Bergstein |
| 2009/0011441 | A1 | 1/2009 | Bergstein |
| 2009/0022740 | A1 | 1/2009 | Bergstein |
| 2009/0022741 | A1 | 1/2009 | Bergstein |
| 2009/0028878 | A1 | 1/2009 | Bergstein |
| 2009/0028879 | A1 | 1/2009 | Bergstein |

FOREIGN PATENT DOCUMENTS

| | | |
|---|---|---|
| WO | WO 90/12885 | 11/1990 |
| WO | WO 94/07474 | 4/1994 |
| WO | WO 95/07348 | 3/1995 |
| WO | WO95/30439 | 11/1995 |
| WO | WO 96/16668 | 6/1996 |
| WO | WO 97/22360 | 6/1997 |
| WO | WO 97/35614 | 10/1997 |
| WO | WO 00/40229 | 7/2000 |
| WO | WO 02/40717 | 5/2002 |
| WO | WO 03/016470 | 2/2003 |
| WO | WO2007053648 | * 5/2007 |

OTHER PUBLICATIONS

Melhem et al (Cancer Research, 1992, vol. 52, pp. 5853-5864).*
abstract of Chan et al (Journal of Clinical Oncology, 1990, vol. 8, pp. 689-704).*
Martins-Neves et al (BMC Cancer, 2012, vol. 12., 16 pages).*
Verrelle et al (JNCI, 1991, vol. 83, pp. 111-116).*
the abstract of Han et al (Zhongguo Putong Waike Zazhi, 2012, vol. 21, pp. 1389-1393).*
Joensuu et al (American Journal of Pathology, 1993, vol. 143, pp. 867-874).*
Gorai et al (International Journal of Cancer, Sep. 4, 1997, vol. 72, pp. 821-827).*
Berezovska et al., 2000, "Rapid Notch1 nuclear translocation after ligand binding depends on presenilin-associated gamma-secretase activity," Ann. N. Y. Acad. Sci. 920:223-6 (abstract).
Bodey et al., 2000, "Failure of cancer vaccines: the significant limitations of this approach to immunotherapy," Anticancer Res. 20(4):2665-76.
Bonnet et al., 1997, "Human acute myeloid leukemia is organized as a hierarchy that originates from a primitive hematopoietic cell," Nat. Med. 3(7):730-7.
Boucher et al., 1995, "The expression of trophoblastic cell markers by lung carcinomas," Hum. Pathol. 26(11):1201-6.
Chen et al., 1997, "Use of arsenic trioxide (As2O3) in the treatment of acute promyelocytic leukemia (APL): I. As2O3 exerts dose-dependent dual effects on APL cells," Blood 89(9):3345-53.

(Continued)

Primary Examiner — Karen Canella
(74) Attorney, Agent, or Firm — Jones Day

(57) ABSTRACT

Improved methods for treatment of cancer which involve the targeting of slow-growing, relatively mutationally-spared cancer stem line are provided. These methods are an improvement over previous cancer therapeutic methods because they provide for very early cancer treatment and reduce the likelihood of clinical relapse after treatment.

5 Claims, 6 Drawing Sheets

(56) References Cited

OTHER PUBLICATIONS

Cripps et al., 2002, "Phase II randomized study of ISIS 3521 and ISIS 5132 in patients with locally advanced or metastatic colorectal cancer: a National Cancer Institute of Canada clinical trials group study," Clin. Cancer Res. 8(7):2188-92.
Door, 1997, "Three A's of repopulation during fractionated irradiation of squamous epithelia: Asymmetry loss, Acceleration of stem-cell divisions and Abortive divisions," Int. J. Radiation Biol. 72(6):635-643.
Eck et al., 1996, "Gene-Based Therapy," The Pharmacological Basis of Therapeutics, Goodman and Gillman, Eds., pp. 77-10.
Grim et al., 1998, "Intracellular expression of the anti-erbB-2 sFv N29 fails to accomplish efficient target modulation," Biochem. Biophys. Res. Commun. 250(3):699-703.
Haynes et al., 1985, "The ultrastructural immunohistochemistry of oncofoetal antigens in large bowel carcinomas," Virchows. Arch. A Pathol. Anat. Histopathol. 405(2):263-75.
Heikinheimo et al., 1987, "Oncoplacental protein SP1—a constitutive and inducible late differentiation marker of the human myelomonocytic lineage," Blood 70(5):1279-83.
Hope et al., 2003, "Human acute myeloid leukemia stem cells," Arch. Med. Res. 34(6):507-14.
James et al., 1998, "The therapeutic potential of ribozymes," Blood 91(2):371-82.
Jones et al., 1998, "Antibodies for targeted gene therapy: extracellular gene targeting and intracellular expression," Adv. Drug. Delivery Reviews 31:153-170.
Lin et al., 1997, "Neuroblasts: a model for the asymmetric division of stem cells," Trends Genetics 13(1):33-39.
Marshall et al., 2004, "A phase II trial of ISIS 3521 in patients with metastatic colorectal cancer," Clin. Colorectal Cancer 4(4):268-74.
Metcalf, 1983, "Early events in the suppression of myeloid leukemic cells by biological regulators," Haematol. Blood Transfus 28:320-6.
Miraglia et al., 1997, "A novel five-transmembrane hematopoietic stem cell antigen: isolation, characterization, and molecular cloning," Blood 90(12):5013-21.
Miyamura et al., 1991, Sapporo Igaku Zasshi 60:183-196 (abstract).
Mizutani, 1990, Sapporo Medical Journal 59:345-356 (abstract).
Moroz et al., 1993, "Oncoprecipitins: A novel type of natural substances and oncofetal antigens," Pure and Appl. Chem. 65(6):1253-1264.
O'Brien et al., Recent Clinical Developments in Gynecologic Oncology, Paul Morrow et al., Ed., pp. 167-180.
Orkin et al., 1995, "Report and Recommendation of the Panel to Assess the NIH Investment in Research on Gene Therapy," NIH.
Otto et al., 1997, "Lung stem cells," Int. J. Exp. Pathol. 78(5):291-310.
Oza et al., 2003, "Phase II study of CGP 69846A (ISIS 5132) in recurrent epithelial ovarian cancer: an NCIC clinical trials group study (NCIC IND.116)," Gynecol. Oncol. 89(1):129-33.
Passegue et al., 2003, "Normal and leukemic hematopoiesis: are leukemias a stem cell disorder or a reacquisition of stem cell characteristics?," Proc. Natl. Acad. Sci. U. S. A. 100 Suppl 1:11842-9.
Rooney et al., 1988, "Molecular cloning of a cDNA for human pregnancy-specific beta 1-glycoprotein:homology with human carcinoembryonic antigen and related proteins," Gene 71(2):439-49.
Sachs, 1991, "The control of growth and differentiation in normal and leukemic blood cells," Cancer 67(S10):2684-2694.
Sakakibara et al., 1996, "Mouse-Musashi-1, a neural RNA-binding protein highly enriched in the mammalian CNS stem cell," Dev. Biol. 176(2):230-42.
Schlom, 1991, Molecular foundations of Oncology, Samuel Broder, Ed., pp. 95-134.
Schultze et al., 2004, "DCs and CD40-activated B cells: current and future avenues to cellular cancer immunotherapy," Trends Immunol. 25(12):659-64.
Sherley et al., 1995, "Expression of the wild-type p53 antioncogene induces guanine nucleotide-dependent stem cell division kinetics," Proc. Natl. Acad. Sci. U. S. A. 92(1):136-40.
Shtalrid et al., 1987, "Review of clinical and haematological response to low-dose cytosine arabinoside in acute myeloid leukaemia," Eur. J. Haematol. 38(1):3-11.
Stedman's Medical Dictionary, 27th Edition, 1985.
Taichman et al., 2002, "NotchI and JaggedI expression by the developing pulmonary vasculature," Dev. Dyn. 225(2):166-75 (abstract).
Ten Have-Opbroek et al., 1997, "The alveolar type II cell is a pluripotential stem cell in the genesis of human adenocarcinomas and squamous cell carcinomas," Histol. Histopathol. 12(2):319-36 (abstract).
Tolcher et al., 2002, "A randomized phase II and pharmacokinetic study of the antisense oligonucleotides ISIS 3521 and ISIS 5132 in patients with hormone-refractory prostate cancer," Clin. Cancer Res. 8(8):2530-5.
Verma et al., 1997, "Gene therapy—promises, problems and prospects," Nature 389(6648):239-42.
Vile et al., 2000, "Cancer gene therapy: hard lessons and new courses," Gene Ther. 7(1):2-8.
Baselga et al., "Phase I studies of anti-epidermal growth factor receptor chimeric antibody C225 alone and in combination with cisplatin," J. Clin, Oncol., 2000, 18(4):904-914.
Baselga et al., "Phase II study of weekly intravenous recombinant humanized anti-p185HER2 monoclonal antibody in patients with HER2/neu-overexpressing metastatic breast cancer," J. Clin. Oncol., 1996, 14(3):737-744.
Baselga et al., "Phase II study of weekly intravenous trastuzumab (Herceptin) in patients with HER2/neu-overexpressing metastatic breast cancer," Semin. Oncol., 1999, 26(4 Suppl. 12):78-83.
Bos et al., "Phase I studies of anti-epidermal growth factor (EGFR) chimeric monoclonal antibody C225 in patients with EGFR overexpressing tumors," Abstract No. 1381 at the 1996 ASCO Annual Meeting.
Cobleigh et al., "Multinational study of the efficacy and safety of humanized anti-HER2 monoclonal antibody in women who have HER2-overexpressing metastatic breast cancer that has progressed after chemotherapy for metastatic disease," J. Clin. Oncol., 1999, 17(9):2639-2648.
Denardo et al., "Radioimmunotherapy for breast cancer using indium-111/yttrium-90 BrE-3: Results of a phase I clinical trial," J. Nuclear Med., 1997, 38(8):1180-1185.
Frodin et al. (abstract), "MAb17-1A and cytokines for the treatment of patients with colorectal carcinoma," 2002, Hybrid Hybridomics, 21:99-101.
Gires et al., "On the abundance of EpCAM on cancer stem cells," 2009, Nat. Rev. Cancer, 9:143.
Gunnett et al., "Phase II study of anti-epidermal growth factor receptor (EGFr) antibody C225 alone in patients (pts) with metastatic renal cell carcinoma (RCC)," Abstract No. 1309 at the 1999 ASCO Annual Meeting.
Hempel et al., "Transplantation of ex vivo tumor cell purged PBSCT in breast cancer patients treated with high dose chemotherapy followed by supplementary immunotherapy with MOAB 17-1-A phase 1 study," Abstract No. 554 at the 1998 ASCO Annual Meeting.
Kawasaki et al., "Metastatic potential of lymphoma/leukemia cell lines in SCID mice is closely related to expression of CD44," 1996, Jpn. J. Cancer Res., 87:1070-1077.
Moseley et al., "Carcinomatous meningitis: antibody-guided therapy with I-131 HMFG1," J. Neurol. Neurosurg. and Psych., 1991, 54:260-265.
Nicholson et al., "Radioimmunotherapy after chemotherapy compared to chemotherapy alone in the treatment of advanced ovarian cancer: a matched analysis," Oncol. Rep., 1998, 5(1):223-226.
Notice of Allowance in file history of U.S. Appl. No. 09/468,286, filed Dec. 20, 1999.
Notice of Allowance in file history of U.S. Appl. No. 11/583,841, filed Oct. 18, 2006.
Notice of Allowance in file history of U.S. Appl. No. 11/583,857, filed Oct. 18, 2006.
Pegram et al., "Phase II study of receptor-enhanced chemosensitivity using recombinant humanized anti-p185HER2/neu monoclonal antibody plus cisplatin in patients with HER2/neu-overexpressing metastatic breast cancer refractory to chemotherapy treatment," J. Clin. Oncol., 1998, 16(8):2659-2671.

(56) References Cited

OTHER PUBLICATIONS

Pronzato et al. (abstract), "A phase II study with danazol in metastatic breast cancer," 1987, Am. J. Clinical Oncology, 10:407-409.
Ragnhammar et al., "Effect of monoclonal antibody 17-1A and GM-CSF in patients with advanced colorectal carcinoma—long-lasting, complete remissions can be induced," Int. J. Cancer, 1993, 53:751-758.
Riethmuller et al., "Randomised trial of monoclonal antibody for adjuvant therapy of resected Dukes' C colorectal carcinoma. German Cancer Aid 17-IA Study Group," Lancet, 1994, 343(8907):1177-1183.
Schrier et al., "High dose 90Y Mx-diethylenetriaminepentaacetic acid (DTPA)-BrE-3 and autologous hematopoietic stem cell support (AHSCS) for the treatment of advanced breast cancer: a phase I trial," Cancer Res. (Suppl.), 1995, 55:5921s-5924s.
Slovin et al., "Epidermal growth factor receptor (EGFr) monoclonal antibody (MoAb) C225 and doxorubicin (DOC) in androgen-independent (AI) prostate cancer (PC): results of a phase Ib/IIa study," Abstract No. 1108 at the 1997 ASCO Annual Meeting.
U.S.P.T.O. Office Action, dated Oct. 1, 2007, issued in connection with U.S. Appl. No. 11/583,841.
U.S.P.T.O. Office Action, dated Feb. 13, 2009, issued in connection with U.S. Appl. No. 11/583,744.
U.S.P.T.O. Office Action, dated Mar. 3, 2008, issued in connection with U.S. Appl. No. 11/583,744.
U.S.P.T.O. Office Action, dated May 23, 2008, issued in connection with U.S. Appl. No. 11/583,744.
U.S.P.T.O. Office Action, dated Jun. 24, 2009, issued in connection with U.S. Appl. No. 11/583,860.
U.S.P.T.O. Office Action, dated Jun. 25, 2009, issued in connection with U.S. Appl. No. 11/583,859.
U.S.P.T.O. Office Action, dated Jul. 10, 2009, issued in connection with U.S. Appl. No. 11/583,871.
U.S.P.T.O. Office Action, dated Jul. 16, 2008, issued in connection with U.S. Appl. No. 11/583,744.
U.S.P.T.O. Office Action, dated Sep. 12, 2007, issued in connection with U.S. Appl. No. 11/583,744.
U.S.P.T.O. Office Action, dated Sep. 26, 2007, issued in connection with U.S. Appl. No. 11/583,857.
Weiner et al., "Phase II multicenter evaluation of prolonged murine monoclonal antibody 17-1A therapy in pancreatic carcinoma," J. Immunother Emphasis Tumor Immunol., 1993, 13(2):110-116.
Beachy et al., 1997, "Multiple Roles of Cholesterol in Hedgehog Protein Biogenesis and Signaling." Cold Spring Harbor Symposia on Quantitative Biology, vol. LXII 191-204.
Cao et al., 2006, "Glycogen synthase kinase-3β positively regulates the proliferation of human ovarian cancer cells." Cell Res. 16:671-77.
Chen et al., 2004, "Activity-Dependent Internalization of Smoothened Mediated by β-Arrestin 2 and GRK2." Science 306:2257-60.
Chiang et al., 1996, "Cyclopia and defective axial patterning in mice lacking Sonic hedgehog gene function." Nature 383:407-13.
Degos et al., 1995, "All-trans-retinoic acid as a differentiating agent in the treatment of acute promyelocytic leukemia." Blood 85:2643-53.
Farber et al, 1984, "The multistep nature of cancer development."Cancer Res 44:4217-23.
Farber et al, 1991, "Cellular adaptation in the origin and development of cancer." Cancer Res. 51:2751-61.
Feldmann et al., 2007, "Blockade of Hedgehog Signaling Inhibits Pacreatic Cancer Invasion and Metastases: A new Paradigm for Combination Therapy in Solid Cancers." Cancer Res 67(5):2187-96.
Fujii et al., 2007, "An Antagonist of Dishevelled Protein-Protein Interaction Suppresses β-Catenin-Dependent Tumor Cell Growth." Cancer Res. 67(2):573-9.
Genbank Accession No. L37882, "Human frizzled gene product mRNA, complete cds.".

Harding et al., 1995, "A screen for modifiers of Deformed function in Drosophila." Genetics 140: 1339-52.
Hoang et al., 1996, "Primary structure and tissue distribution of FRZB, a novel protein related to Drosophila frizzled, suggest a role in skeletal morphogenesis."J. Biol. Chem. 271(42):26131-7.
Holliday et al., 1979, "A new theory of carcinogenesis." Br. J. Cancer 40:513-22.
Hou et al, 1985, "Measurement of Antibody-Depndent Cell-Mediated Cytotoxicity by Hb-Enzyme Release Assay (Hb-ERA)." J. of Immunol. Methods 85:325-33.
Incardona et al., 1997, "Alterd Sonic Hedgehog Function is an Early Event in Cyclopamine-Induced Holoprosencephaly." 30th Annual Northwest Regional Developmental Biology Conference; Friday Harbor, Washington.
Jordan, 2007, "The leukemic stem cell." Best Practice & Reearch Clinical Haematology 20(1):13-18.
Karhadkar et al., 2004, "Hedgehog signalling in prostrate regeneration, neoplasia and metastasis." Nature 431:707-12.
Kennedy et al., 1984, "Timing of the steps in transformation of C3H 10T 1/2 cells by X-irradiation." Nature 307:85-6.
Klein et al., 1996, "A molecular mechanism for the effect of lithium on development." Proc. Natl. Acad. Sci 93(16):8455-9.
Mayr et al., 1997, "Fritz: a secreted frizzled-related protein that inhibits Wnt activity." Mechan. of Dev. 63:109-25.
Miyazaki et al., 2006, "Treatment of Eyelid Epithelial Neoplasm by Targeting Sonic Hedgehog Signaling: An Experimental Study." Jpn J. Opthalmol 50:305-11.
Nagayama et al., 2005, "Therapeutic potention of antibodies against FZD10, a cell-surface protein for synovial sarcomas." Oncogene 24:6201-12.
Pierce et al, 1988, "Tumors as caricatures of the process of tissue renewal: prospects for therapy by directing differentiation." Cancer Res 48:1996-2004.
Pierce et al., 1978, "Cancer: a problem of developmental biology." New Jersey, Prentice Hall.
Roessler et al., 1996, "Mutations in the human Sonic Hedgehog gene cause holoprosencephaly" Nature Genetics 14:357-60.
Rubin et al., 1985, "Cancer as a dynamic developmental disorder." Cancer Res 45:2935-42.
Sanchez et al., 2005, "In vivo inhibition of endogenouse brain tumors through systemic interference of Hedgehog signaling in mice." Mech. Dev. 122(2):223-230.
Stecca et al., 2005, "Interference with HH-GLI signaling inhibits prostate cancer." Trends in Molec. Med. 11(5): 199-203.
Vogelstein et al., 1993, "The multistep nature of cancer." Trends genetics 9:138-41.
Yu et al., 2007, "Association of Dishevelled with the Clathrin AP-2 Adaptor is Required for Frizzled Endocytosis and Planar Cell Polarity Signaling." Develop. Cell 12:129-41.
Zhao et al., 1995, "A human homologue of the Drosophila polarity gene frizzled has been identified and mapped to 17q21.1." Genomics 27(2):370-73.
Zhu et al., 2003, "Altered location of Drosophila Smoothened protein activates Hedgehog signal transduction." Genes & Dev 17:1240-52.
Zilberberg et al., 2004, "The Low Density Lipoprotein Receptor-1, LRP1, Interacts with Human Frizzled-1 (HFz1) and Down-regulates the Canonical Wnt Signaling Pathway." J. Biol. Chem. 279(17):17535-42.
Bui and Reiter, Stem cell genes in androgen-independent prostate cancer. Cancer Metastasis Rev. 1998-1999;17(4):391-9.
Gels et al., Importance of a new tumor marker TRA-1-60 in the follow-up of patients with clinical stage I nonseminomatous testicular germ cell tumors. Ann Surg Oncol. Jun. 1997;4(4):321-7.
Peters et al., Day-6 bone marrow aspirate for the prediction of response to remission induction therapy for acute myelogenous leukaemia. Blut. Aug. 1988;57(2):91-5.
Sigal et al., The liver as a stem cell and lineage system. Am J Physiol. Aug. 1992;263(2 Pt 1):G139-48.
Tanaka et al. Nihon Igaku Hoshasen Gakkai zasshi. Nippon acta radiological, 1996, vol. 13, pp. 967-973 (Abstract).
Watt FM., Epidermal stem cells: markers, patterning and the control of stem cell fate. Philos Trans R Soc Lond B Biol Sci. Jun. 29, 1998;353(1370):831-7.

(56) References Cited

OTHER PUBLICATIONS

Gecz et al., Assignment of a Polycomb-like chromobox gene (CBX2) to human chromosome 17q25. Genomics. Mar. 1, 1995;26(1):130-3.
Schumacher and Magnuson, Murine Polycomb- and trithorax-group genes regulate homeotic pathways and beyond. Trends Genet. May 1997;13(5):167-70.
Satijn et al., Interference with the expression of a novel human polycomb protein, hPc2, results in cellular transformation and apoptosis. Mol Cell Biol. Oct. 1997;17(10):6076-86.
Stone et al., The tumour-suppressor gene patched encodes a candidate receptor for Sonic hedgehog. Nature. Nov. 14, 1996;384(6605):129-34.

* cited by examiner

Conventional Model

OSES Model

OSES-based antibody therapy

Induction of asymmetric cancer stemline mitosis

Induction of symmetric cancer stemline differentiation/apoptosis

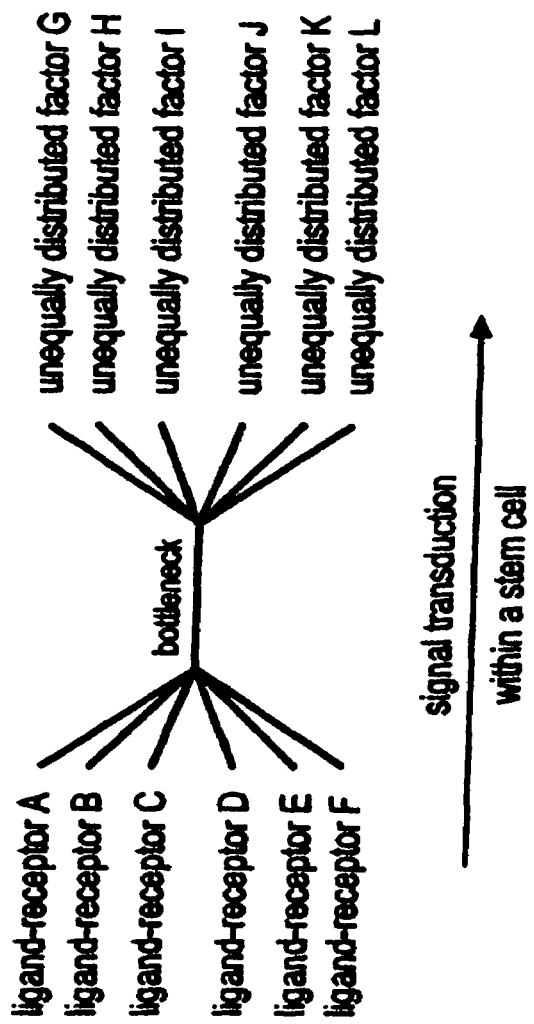

asymmetric mitosis stem cell symmetric mitosis stem cell

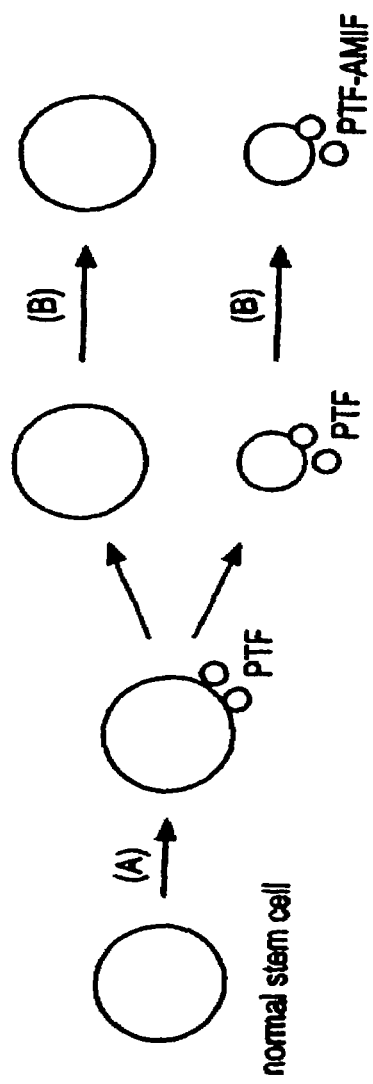
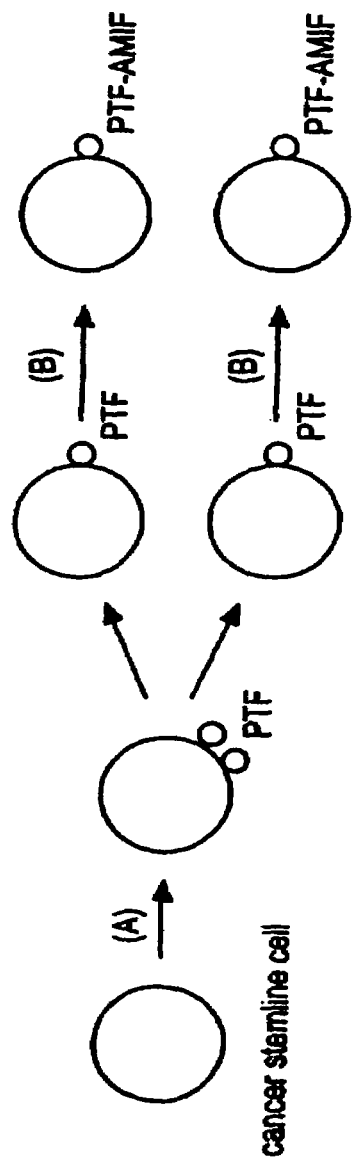

METHODS OF CANCER DIAGNOSIS AND THERAPY TARGETED AGAINST A CANCER STEM LINE

CROSS REFERENCE TO RELATED APPLICATIONS

This application is a continuation of U.S. application Ser. No. 11/271,381, filed Nov. 10, 2005 now U.S. Pat. No. 8,038,998, which is a continuation of U.S. application Ser. No. 09/468,286, filed Dec. 20, 1999, now U.S. Pat. No. 7,361,336, issued Apr. 22, 2008, which is a continuation-in-part of U.S. application Ser. No. 08/933,330, filed Sep. 18, 1997, now U.S. Pat. No. 6,004,528, issued Dec. 21, 1999, each of which is incorporated by reference in its entirety herein.

FIELD OF THE INVENTION

The present invention relates to novel methods for the diagnosis and treatment of cancer, and is based on the novel OSES ("one-step epigenetic switch") model of carcinogenesis.

BACKGROUND OF THE INVENTION

Classical cancer models to date which have attempted to explain the character of cancer cells have typically described them as fast-growing and highly mutant cells. These cancer cells are hypothesized to have been produced during carcinogenesis because of a multi-step neo-Darwinian evolutionary process involving mutation-selection events at the cellular level (Fearon et al, "A Genetic Model for Colorectal Tumorigenesis", *Cell,* 61:759-767 (1990); Nowell, "The Clonal Evolution of Tumor Cell Populations", *Science* (Washington, D.C.), 194:23-28 (1976)).

Related to this, conventional cancer diagnoses and therapies to date have attempted to selectively detect and eradicate neoplastic cells that are largely fast-growing and mutant. For example, conventional cancer chemotherapies (e.g., alkylating agents such as cyclophosphamide, anti-metabolites such as 5-Fluorouracil, plant alkaloids such as vincristine) in a similar manner to conventional irradiation therapies both exert their toxic effects on cancer cells by interfering with numerous cellular mechanisms involved in cell growth and DNA replication. Other less commonly used experimental cancer therapies have included use of immunotherapies wherein the administration of therapeutic agents which selectively bind mutant tumor antigens on fast-growing cancer cells (e.g., monoclonal antibodies) have been attached to therapeutic moieties such as toxins, radionuclides or chemotherapeutic agents for the purpose of eradicating fast-growing mutant cancer cells. Similarly, newer experimental gene-directed therapies have attempted to exploit certain cancer-related mutations by correcting or replacing such defect by, e.g., inserting wildtype versions of such mutant genes (e.g., p53) into cancer cells, inhibiting overactive oncogenes (e.g., ras) in tumor cells, or by using existing mutations in cancer cells as targets for other therapeutic (e.g., viral) vectors (Feng et al, "Neoplastic reversion accomplished by high efficiency adenoviral-mediated delivery of an anti-ras ribozyme", *Cancer Res.,* 55:2024-2028 (1995); Bischoff et al, "An adenovirus that replicates in p53-deficient human tumor cells", *Science,* 274:373-376 (1997)). While all of these methods (i.e., conventional chemotherapies, radiation, immunotherapies, and gene therapies) may, by their design, eradicate a significant proportion of a given tumor mass by destroying the large populations of highly proliferative and mutant neoplastic cells thus resulting in a clinical remission, in time the tumor may recur at the same or different site(s), thereby indicating that not all cancer cells have been eradicated by these methods. A number of reasons for tumor relapse have been offered within the conventional paradigm. These include insufficient chemotherapeutic dosage (limited by onset of significant side effects), and/or emergence of cancer clones which are resistant to therapy.

The novel model for carcinogenesis presented here (termed the OSES model) offers an alternative explanation for relapse wherein (as will be discussed in more detail) a clandestine slow-growing relatively mutationally-spared cancer stem line acts as the immortal founder line of a tumor and produces as its progeny the highly proliferative mutant cancer cell populations targeted by conventional therapies mentioned above. Accordingly, it will be shown that this cancer stem line (hypothesized to exist by the OSES model) is not targeted by conventionally-based therapies (designed to target fast-growing largely mutant cells rather than slow-growing non-mutant cells). In this manner, the untargeted cancer stem line can gradually regrow the tumor mass following standard therapy thereby leading to treatment failure and clinical relapse.

Recently much evidence has been accumulated which raises significant concerns as to the validity of classical cancer models based on the neo-Darwinian paradigm—and thus also to the efficacies of cancer therapies wholly based on this model. So that the invention may be understood, previous conventional cancer models and their inadequacies are discussed below.

There is extensive evidence that cancer results from the evolution of an increasingly "cancer-like" tissue type leading ultimately to one with malignant capability (Furth, "Conditioned and autonomous neoplasms: a review", *Cancer Res.,* 13:477-492 (1953); Foulds, "The natural history of cancer", *J. Chronic Dis.,* 8:2-37 (1958)). That mutagenesis is causally involved in the initiation of this process is a concept which has stemmed largely from demonstrations that genotoxic carcinogens can cause cellular transformation and that this "initiated" phenotype is rare, permanent, focal and heritable. (Berenblum, "Sequential aspects of chemical carcinogenesis: skin, in: F. F. Becker (ed.), *Cancer: a Comprehensive Review,* pp. 451-484, New York, Plenum Publishing Corp. (1982); Cohen et al, "Genetic Errors, Cell Proliferation, and Carcinogenesis", *Cancer Res.,* 51:6493-6505 (1991)). Moreover, that a mutant gene can bestow a transmissible cancer phenotype is evidenced by transfection and transgenic experiments as well as recent genetic linkage analyses of human familial cancers (Weinberg, "Oncogenes, Anti-oncogenes, and the Molecular Basis of Multistep Carcinogenesis", *Cancer Res.,* 49: 3713-3721 (1989); Tsukamoto et al, "Expression of the int-1 gene in transgenic mice is associated with mammary gland hyperplasia and adenocarcinomas in male and female mice", *Cell,* 55: 619-625 (1988); Knudson, "Hereditary cancer, oncogenes, and antioncogenes", *Cancer Res.,* 45: 1437-1343 (1985)). It is also clear that while the onset of carcinogenesis requires an initial (acquired or inherited) mutagenic insult, subsequent alterations are also necessary for attainment of malignancy (Nowell, "The Clonal Evolution of Tumor Cell Populations", *Science* (Washington D.C.), 194: 23-28 (1976)).

This concept is supported by findings that certain cultured cells transfected with a single oncogene required additional alterations to become fully transformed. (Weinberg, "Oncogenes, Anti-oncogenes, and the Molecular Basis of Multistep Carcinogenesis", *Cancer Res.,* 49:3713-3721 (1989)). Moreover, epidemiological data implicating a series of rate limiting steps in the pathogenesis of human cancers has lent support to the concept that a gradual cellular progression toward increasing malignancy is driven by neo-Darwinian mutation-selection (Miller, "On the Nature of Susceptibility to Cancer", *Cancer,* 46:1307-1318 (1980).

Also, the well-documented association between increasing mutational load and tumor grade has led to the seemingly most parsimonious mechanistic explanation of these data whereby mutations cause both the initiation as well as progression of neoplasia via a continuum of mutation-selection events at the cellular level (Nowell, "The Clonal Evolution of Tumor Cell Populations.", *Science* (Washington D.C.), 194: 23-28 (1976); Fearon et al, "A Genetic Model for Colorectal Tumorigenesis", *Cell,* 61: 759-767 (1990)). Additional support for this neo-Darwinian model derives from recent high-resolution molecular analyses of human tumor biopsy specimens that reveal a tight correlation between the appearance of certain defined genetic alterations and the transition to increasingly "cancerous-appearing" tumor regions (Fearon et al, "A Genetic Model for Colorectal Tumorigenesis", *Cell,* 61: 759-767 (1990); Sidransky et al, "Clonal expansion of p53 mutant cells is associated with brain tumor progression", *Nature* (Lond.), 355: 846-847 (1992); Sato et al, "Allelotype of Breast Cancer: Cumulative Allele Losses Promote Tumor Progression in Primary Breast Cancer", *Cancer Res.,* 50: 7184-7189 (1990)).

However, it should be noted that there is a body of cancer literature not readily accounted for by standard neo-Darwinian mutation-selection models. Namely, there are a host of independent data describing unexpectedly elevated transformation rates observed in certain carcinogen-treated cells not fully accounted for by somatic mutation alone as well as the capability of some highly malignant tumor types to differentiate or even revert to normal under certain conditions—findings also not readily explained by conventional mutation-selection models (Kennedy et al, "Timing of the steps in transformation of C3H 10T1/2 cells by X-irradiation", *Nature* (Lond.), 307: 85-86 (1984); Rubin, "Cancer as a Dynamic Developmental Disorder", *Cancer Res.,* 45: 2935-2942 (1985); Farber et al, "Cellular Adaptation in the Origin and Development of Cancer", *Cancer Res.,* 51: 2751-2761 (1991)). Accordingly, alternative models to mutation-selection (e.g., invoking a role for potentially reversible non-mutational/epigenetic alterations as effectors of cellular evolution toward increasing malignancy) have been advanced by several investigators in order to explain these and other related phenomena.

For example, as alluded to, while only a minority of mouse prostate cells exposed to methylcholanthrene initially become transformed, the entire population of treated cells rear progeny with an increased propensity for transformation at subsequent cell divisions despite removal of the carcinogenic agent. Similarly, treatment of various rodent cells with other types of carcinogens, namely X-irradiation or retroviral infection, also results in transformation of progeny of initially untransformed cells at an overall rate difficult to reconcile by somatic mutagenesis alone (Farber et al, "Cellular Adaptation in the Origin and Development of Cancer", *Cancer Res.,* 51:2751-2761 (1991)). In addition, Rubin has demons that although only a small fraction of growth-constrained NIH3T3 cells form transformed foci, the entire population of these murine fibroblasts gives rise to clones with elevated transformation rates (Rubin, "Cellular epigenetics: Control of the size, shape, and spatial distribution of transformed foci by interactions between the transformed and nontransformed cells", *Proc. Nat. Acad. Sci.* USA, 91: 6619-6623 (1994)). In a related manner, while only a minority of in vivo DMBA-treated murine skin cells become transformed, heritable phenotypic alterations are present in the entire basal skin cell layer exposed to this chemical carcinogen thereby corroborating those mentioned in vitro experiments cited in support of a widespread heritable phenotypic effect by certain carcinogens beyond that which can be attributed wholly to their mutagenic effects (Farber et al, "Cellular Adaptation in the Origin and Development of Cancer", *Cancer Res.,* 51: 2751-2761 (1991)).

It has also been noted, as mentioned, that a variety of cancer cell types can differentiate to varying degrees. For example, human neuroblastoma cells sprout axons and dendrites when grown as explants and murine leukemic cells differentiate into benign granulocytes and macrophages when grown in vitro. Moreover, tritiated thymidine labeling of rodent squamous cell carcinomas and skeletal muscle tumors illustrates that poorly differentiated cells within these tumors can give rise to well-differentiated squamous epithelia and multinucleated myotubes, respectively. In addition, somatic tissues of transplantable mouse teratocarcinomas have been shown to be benign differentiated progeny of a subpopulation of poorly differentiated embryonal carcinoma cells within these particular tumors. Most recently, all-trans-retinoic acid (ATRA) has been found to be efficacious in the treatment of human acute promyelocytic leukemia (APL) by inducing terminal differentiation of malignant leukocytes (Pierce et al (eds.), "Cancer: a problem of developmental biology", New Jersey: Prentice Hall Inc. (1978); Degos et al, "All Trans-Retinoic Acid as a Differentiating Agent in the Treatment of Acute Promyelocytic Leukemia", *Blood,* 85: 2643-2653 (1995)).

Accordingly, it had been suggested by some investigators that conventional cancer models may not adequately explain elevated transformation rates of certain cells types (not adequately explained by somatic mutation alone), or the differentiation capability of certain tumor cells presumably having arisen via a cascade of random genetic derangements. Based on these and other related observations, Rubin, Farber, and Pierce among others have theorized that the ability of certain cancer cells to differentiate might suggest that a cancer cell originates from potent developing/renewing cells which undergo defective morphogenesis rather than from mutant cells which undergo dedifferentiation. Moreover, it has been argued by several investigators that mechanistically such defective morphogenesis is likely to arise from a series of non-mutational (i.e., epigenetic) alterations (rather than mutations) which by definition leave the genome fairly intact and differentiation-related genes functional. Cited in additional of this cancer theory is the observation that certain malignant cells can not only produce differentiated progeny but can also do so in a relatively orderly manner which mimics normal tissue development under specified conditions. For example, neuroblastoma growth and differentiation is regulated when placed into neurula-stage embryos, and the behavior of melanoma cells is controlled when transplanted into fetal skin (Podesta et al, "The neurula stage mouse embryo in control of neuroblastoma", *Proc. Natl. Acad. Sci.* USA, 81: 7608-7611 (1984); Gerschenson et al, "Regulation of melanoma by the embryonic skin", *Proc. Natl. Acad. Sci.* USA, 83: 7307-7310 (1980)). In addition, leukemic cells differentiate into normal hematopoietic tissue when injected into mouse embryos during leukocyte progenitor development and placement of malignant embryonal carcinoma cells into the embryonic milieu of a developing blastocyst results in complete reversion and differentiation of these cells into multiple tissue types leading to the formation of viable murine chimeras (Pierce et al (eds.), "Cancer: a problem of developmental biology", New Jersey: Prentice Hall Inc. (1978); Gootwine et al, "Participation of myeloid leukaemic cells injected into embryos in hematopoietic differentiation in adult mice", Nature (London), 299: 63-65 (1982)). In a related manner, restoration of native environmental conditions at a particular adult tissue locale (i.e., without transplantation) causes certain tumors to "behave" as a normal tissue—e.g., resolution of normal physiologic hormonal balance causes some murine endocrine tumors to regress and certain rodent sarcomas induced by implantation of an inert material into connective tissues revert when proper tissue architecture is restored (Rubin, "Cancer as a Dynamic Developmental Disorder", Cancer Res., 45: 2935-2942 (1985)).

That altered epigenesis can lead to neoplasia is an idea which is also supported a significant literature documenting the unexpected reversibility of certain carcinogen-transformed cells in culture (Kennedy et al, "Timing of the steps in transformation of C3H 10T1/2 cells by X-irradiation", Nature (Lond.), 307: 85-86 (1984); Rubin, "Cancer as a Dynamic Developmental Disorder", Cancer Res., 45: 2935-2942 (1985)). This idea is also supported by demonstrations that apparently non-mutational events such as transplantation of normal rodent tissues (e.g., testis, pituitary, embryonic ectoderm) to ectopic sites can lead to their neoplastic transformation, while replacement of some of these cancer cell types back into their endogenous micro-environments results in their reversion to normalcy (Rubin, "Cancer as a Dynamic Developmental Disorder", Cancer Res., 45:2935-2942 (1985); Farber and Rubin, "Cellular Adaptation in the Origin and Development of Cancer", Cancer Res., 51:2751-2761 (1991)). Also, evidence that some pre-malignant lesions may be reversible during their early stages has led to the proposal by Farber that a "pre-malignant" phenotype may be no more than a programmed adaptive (epigenetic) cellular response rather than an aberrant product of random permanent mutational events (Farber, "The Multistep Nature of Cancer Development", Cancer Res. 44:4217-4223 (1984); Farber and Rubin, "Cellular Adaptation in the Origin and Development of Cancer", Cancer Res., 51:2751-2761 (1991)).

Accordingly, Rubin, a major proponent of the epigenetic model for cancer, had theorized that the evolution toward malignancy might be due to the progressive selection (i.e., evolution) of increasingly "cancer-like" cells undergoing advantageous epigenetic fluctuations. Moreover, Rubin, as well as Prehn, have offered that the presence of mutational alterations in tumors may not always have a causal role in tumor progression, but rather may be the result of genomic instability associated with the malignant phenotype thereby representing a cancer-related "epiphenomenon". (Rubin, "Cancer as a Dynamic Developmental Disorder", Cancer Res., 45:2935-2942 (1985); Prehn, "Cancers Begets Mutations versus Mutations Beget Cancers", Cancer Res., 54:5296-5300 (1994).

However, considering increasing current molecular evidence in support of a causal role for mutagenesis in human cancer, it is no wonder that attempts have been made not only to consider alternative explanations for the action of epigenesis in carcinogenesis (i.e., other than aberrant morphogenesis which has been linked to the unpopular notion of a non-causal epiphenomenal role for mutations in cancer), but also more radically to regard epigenesis-related data in general as largely anecdotal. Notwithstanding, documentation that a variety of epigenetic alterations (such as changes in DNA methylation and genomic imprinting) are present in human biopsy specimens of a number of different tumor types has undoubtedly helped to resurrect epigenesis as a real cancer-related entity rather than an experimental quirk (Goelz et al, "Hypomethylation of DNA from benign and malignant human colon neoplasms", Science (Washington, D.C.), 228: 187-190 (1985); Feinberg, "Genomic imprinting and gene activation in human cancer", Nature Genet., 2: 110-113 (1993)). Accordingly, current cancer models largely of the mutation-selection variety now regularly include aspect of altered epigenesis into a more general neo-Darwinian paradigm wherein both mutagenesis and epigenesis contribute to cancer evolution by acting as independent effectors of cell variability (Vogelstein et al, "The multistep nature of cancer", Trends Genet., 9: 138-141 (1993)). Thus, in contrast to past models of epigenesis (which have regarded mutations as non-causal), this combined paradigm is able to maintain the well documented causal role for mutagenesis in carcinogenesis.

However, it should be noted that while combining mutagenesis and epigenesis into one general paradigm has the obvious appeasing benefits that accompany compromise, it is still not obvious how such a combined paradigm is any more apt than pure mutagenic models to explain instances of tumor cell regulation, differentiation, or regression if it still invokes rare irreversible (genomic) derangements as major effectors of cell variability. In reference to that model which best accounts for these enigmatic data (i.e., the depiction of cancer as an aberrancy in tissue morphogenesis), it is clear that its current state of relative obscurity can be largely attributed to its unfortunate coupling to the ill-fated notion that cancer-related mutations are mere epiphenomena—a stance clearly at odds with recent data. However, by dismissing this entire model because of an overzealous error in deducting its consequences, is it possible that some have effectively "thrown out the baby with the bathwater", so to speak? Alternatively, if one uncouples the concept of aberrant morphogenesis from any particular stance as to the causality of mutagenesis in carcinogenesis, cancer could then be viewed in a new light as an epigenetic defect in tissue morphogenesis but one which could also, in a seemingly contradictory manner, be abetted by mutations. For example, mutagenesis could cause cancer, not via standard stepwise mutation-selection, but rather by triggering an actively developing/renewing is adult tissue to undergo a largely epigenetic-driven aberrant morphogenetic program. Moreover, subsequent to the birth of a cancer cell in this manner, mutagenesis could then act in another novel non-neo-Darwinian manner by blocking cancer cell reversion (i.e., rather than by promoting progression of pre-cancerous intermediates). Such a model would maintain the causal role of mutagenesis in carcinogenesis while more readily accounting for the epigenetic nature of certain cancers than does the current combined neo-Darwinian model. The preceding scenario is the basis for the OSES model for carcinogenesis, the specific mechanisms of which will be discussed in more detail.

Accordingly, this report will contend that upon closer analysis of the cancer literature: 1) the data normally cited in favor of mutation-selection are not exclusive to the conventional paradigm but rather are also consistent with an alternative and novel non-neo-Darwinian model (termed the OSES model), and that 2) this novel OSES model may have a advantage in being more able than the conventional paradigm to accent for certain past as well as more recently described enigmatic cancer-related phenomena.

Thus, the present invention is based on a novel and improved model for carcinogenesis which incorporates and indeed reconciles the presence of the seemingly conflicting processes of epigenesis and mutagenesis that occur during carcinogenesis. Moreover, based on this novel model of carcinogenesis (i.e., the OSES model), the present invention further provides novel and improved methods for the diagnosis and treatment of cancer. These novel methods should alleviate and potentially prevent problems associated with those of conventional cancer diagnosis and therapy, in particular, the need for methods which provide for much earlier cancer diagnosis than is currently available, as well as the need for more successful initial therapies for cancer that are not as susceptible to tumor relapse as are conventional treatment regimens.

OBJECTS OF THE INVENTION

Thus, it is an object of the invention to provide a novel cancer model—termed the OSES (one step-epigenetic switch) cancer model—which clarifies and repairs the inadequacies of previous cancer models.

Moreover, it is a further object of the invention to provide novel methods of treatment and diagnosis of cancer which are based on the OSES model.

It is a more specific object of the invention to provide a method of cancer diagnosis which identifies slow-growing, relatively mutationally-spared symmetrically-dividing stem cells (i.e., a cancer stem line) which is the immortal founder line that rears those (largely mortal) highly proliferative mutant cancer cells normally targeted by conventional diagnostic methods.

It is a more specific object of the invention to provide a method of cancer therapy which targets slow growing, relatively mutationally-spared symmetrically dividing stem cells (i.e., a cancer stem line) which is the immortal founder line that rears those (largely mortal) highly proliferative mutant cancer cells normally targeted by conventional therapies.

It is another specific object of the invention to provide novel and improved cancer therapies which eradicate a cancer stem line thereby destroying the immortal portion of the tumor (i.e., the cancer stem line) and in doing so providing a true cure by preventing clinical relapse.

It is a more specific object of the invention to provide cancer therapies which target antigens present on the cancer stem line for the purpose of dying the cancer stem line.

It is another specific object of the invention to provide a novel method of cancer therapy which induces, in a cancer stem line, a permanent switch from symmetric to asymmetric mitosis.

It is still another specific object of the invention to provide a novel method of cancer therapy which induces, in a cancer stem line, terminal differentiation and/or programmed cell death.

It is still another specific object of the invention to spare normal stem cells of significant OSES-based therapy-induced toxicities.

BRIEF DESCRIPTION OF THE INVENTION

The present invention provides novel methods for the treatment and detection of cancer which follow from the OSES model of carcinogenesis. In brief, the OSES model concludes that a clandestine relatively mutationally-spared immortal founder line (i.e., cancer stem line) exists within tumors and is responsible for fueling tumor immortality. Since the cancer stem line is directly derived from normal stem cells, as will be described, the cancer stem line (like a normal stem cell) is slow-growing and non-mutant and (like a normal stem cell) rears a transit population of highly proliferative progeny cells (which may be mutant in the case of cancer stem line progeny). Such highly proliferative and largely mortal cancer stem line progeny make up the bulk of the resulting tumor mass (in an analogous manner to which proliferative mortal progeny of normal stem cells make up the bulk of a normal developing tissue).

Essentially, while conventional cancer models invoke the presence of highly proliferative mutant cancers (hypothesized to be produced by stepwise neo-Darwinian mutation-selection), they have been largely unaware of the OSES-proposed presence of an underlying slow-growing relatively mutationally-spared immortal cancer stem line that rears such proliferative mutant cells as its mortal progeny.

Moreover, this deficiency by conventional models explains many of the inadequacies of treatment regimens derived thereof, e.g., conventional chemotherapies, irradiation, experimental immunotherapies, as well as newer gene directed therapies designed for treatment of cancer. In general, such conventionally-based methods attempt to eradicate fast-growing mutant cancer cells. This idea has clinical utility as, if successful, such methods may destroy the highly proliferative mutant progeny of the cancer stem line and thereby diminish tumor burden (since mortal cancer stem line progeny make up the bulk of the tumor mass), thus potentially effecting clinical remission (due to significant decrease in tumor cell burden). However, a problem associated with such treatments is that the targeted highly proliferative mutant cancer cells are largely mortal while their immortal progenitor, i.e., the cancer stem line, will remain spared of such therapies. This is disadvantageous as the cancer stem line over time can rear more highly proliferative mutant cancer cells, thereby effecting an increase in tumor cell burden and clinical relapse.

By contrast, the subject invention provides novel therapies which eradicate the slow-growing relatively mutationally-spared cancer stem line which is the progenitor of of the larger population of highly proliferative, largely mortal, often mutant cancer cells. Therefore, the present invention may provide a true cancer "cure" as it would eradicate the founder line thereby alleviating and potentially preventing clinical relapse.

Also, the present invention provides novel methods of cancer diagnosis by early detection of cancer step lines. This will be effected by detecting factors (e.g., but not exclusive to, cell surface antigens, or intracellular factors) spec to cancer stem lines, e.g., via use of cancer stem line-specific monoclonal antibodies attached to a readily detectable moiety (e.g., fluorescent or radionuclide tag).

As noted, the subject cancer stem line, which can be considered to be the progenitor of highly proliferative mutant cancer cells, is directly derived from normal stem cells and as will be present is functionally equivalent to stem cells that have undergone an aberrant one-step epigenetic switch (OSES) in mitotic mode from an asymmetric to a symmetric type. Therefore, the methods of therapy which arise from the OSES model of carcinogenesis will include, but are not exclusive to, the following:

(i) specific cytotoxic targeting of the cancer stem line, e.g., via immunotherapy designed to cancer stem line-specific antigens (some of which are expressed in and inherited en bloc from normal stem cells;

(ii) induction of permanent switch, in the cancer stem line, from symmetric back to asymmetric mitosis, e.g., via activating/suppressing cellular factors which are involved in this switch in normal stem cells; and/or (iii) induction of permanent terminal differentiation and/or apoptosis of the cancer stem line by forcing the cancer stem line from a symmetric proliferative mitotic program to a symmetric terminal differentiation/apoptotic program whereby proliferative capacity is irreversibly lost.

DETAILED DESCRIPTION OF THE FIGURES

FIGS. 1A and 1B show mitotic of cell division modes (normal versus cancerous). Large circles represent individual stem cells, small circles represent their differentiating progeny cells.

FIG. 1A shows normal asymmetric mitosis of stem cells. The immortal stem line in this case is the renewed normal stem cell while all of its progeny are mortal and destined to differentiate. This represents an arithmetic growth pattern.

FIG. 1B shows symmetric mitosis of stem cells (i.e., cancer). The immortal stem lines in this case are the cancer stem lines which fuel tumor growth. This represents an exponential growth pattern. It should be noted that, by the OSES model, stem cells which are dividing asymmetrically are intrinsically the same as those dividing symmetrically, i.e., the mitotic mode by which stem cells divide is determined by their local surroundings. Thus asymmetrically dividing stem cells have normal surroundings while disrupted surroundings lead stem cells to divide symmetrically.

FIG. 2A illustrates the conventional model, wherein cells that survive standard chemotherapy are speculated to have aquired mutations which make them resistant to therapy.

Figure 2A:
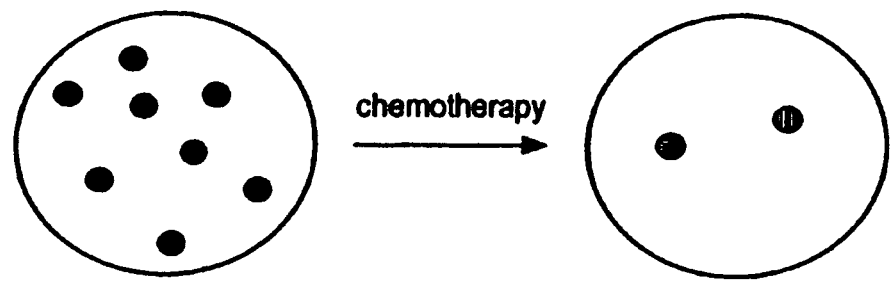
FIGS. 2A and 2B illustrate possible explanations for relapses that follow conventional chemotherapies. Large circles represent tumors, small circles within the large circles represent individual tumor cells; ●=mutant cancer cells susceptible to therapy; ○=cancer stem line cells; ⊕● mutant cancer cells resistant to therapy.
Figure 2B:
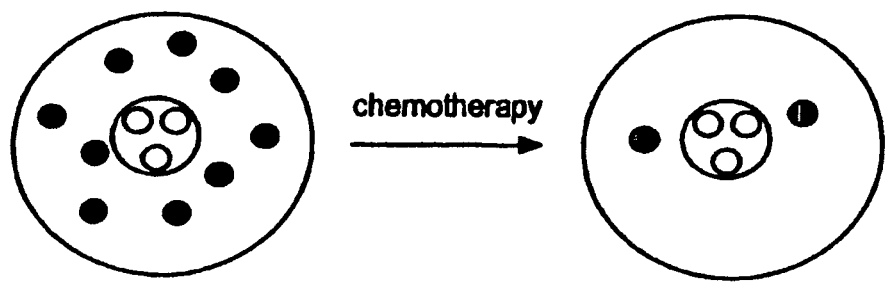

FIG. 2B illustrates the OSES model, wherein cells that survive standard chemotherapy are speculated to have either acquired mutations which make them resistant, or may constitute a sub-population of relatively mutationally-spared cells that are slow-growing (i.e., the cancer stem line) and are thus spared by therapies designed to attack fast-growing mutant cells. By this model, mutationally-resistant cells may have a finite life-span (having been initiated down a differentiation pathway) thereby making their presence following standard chemotherapy less problematic than the presence of an immortal cancer stem line. It should be noted that the presence of cancer stem line cells resistant to standard therapies is a novel OSES-based proposal not predicted by conventional models.

Figure 3A:
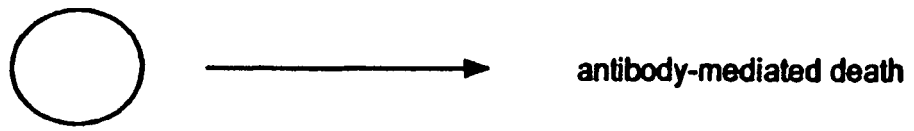
Figure 3B:
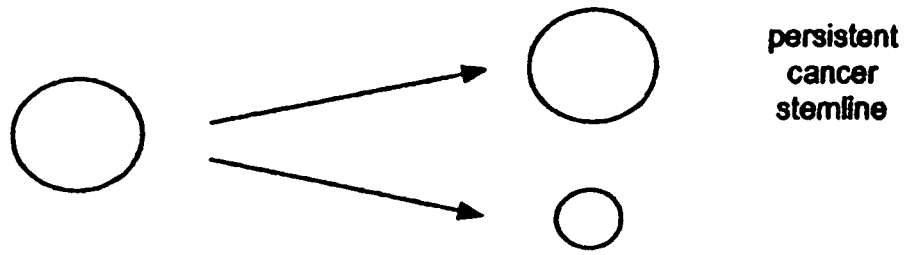
Figure 3C:
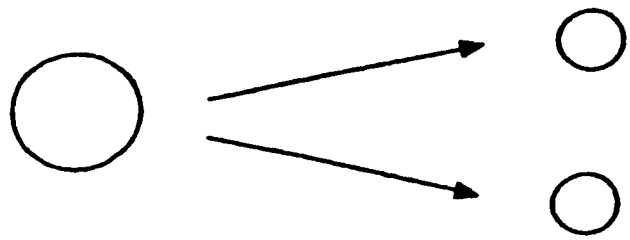

FIGS. 3A, 3B and 3C contain schematic of novel OSES-based cancer therapies. Large circles represent immortal cancer stem line cells, small circles represent mortal progeny cells of the cancer stem line that are either differentiating or undergoing programmed cell death.

FIG. 3A illustrates that monoclonal antibody therapy to antigens present on a cancer stem line leads to cytotoxicity of the cancer stem line.

FIG. 3B illustrates that certain OSES-based therapies force a cancer stem line cell to undergo asymmetric mitosis (i.e., arithmetic growth).

FIG. 3C illustrates other OSES-based therapies force a cancer stem line to undergo symmetric differentiation or programmed cell death (apoptosis) thereby extinguishing the cancer stem line and tumor immortality.

FIG. 4 depicts the asymmetric mitotic pathway of a stem cell. Multiple ligand-receptor binding action (left side of figure) leads to a signal transduction pathway (arrow) characterized by induction of multiple intracellular activators and inhibitors of this pathway acting positively and negatively, respectively (along branches on both sides of figure). This pathway ultimately leads to the unequal segregation of factors (right side of figure) to 2 qualitatively distinct daughter cells (i.e., asymmetric mitosis). Somewhere amid this pathway may exist one or more "bottlenecks" (only one has been displayed for simplicity) wherein cellular decisions are made from a consensus of competing signals. Such "bottlenecks" present convenient points at which to therapeutically intervene (for the purpose of coercing asymmetric or symmetric mitosis) because they harbor less factors to be interfered with.

Figure 5A:
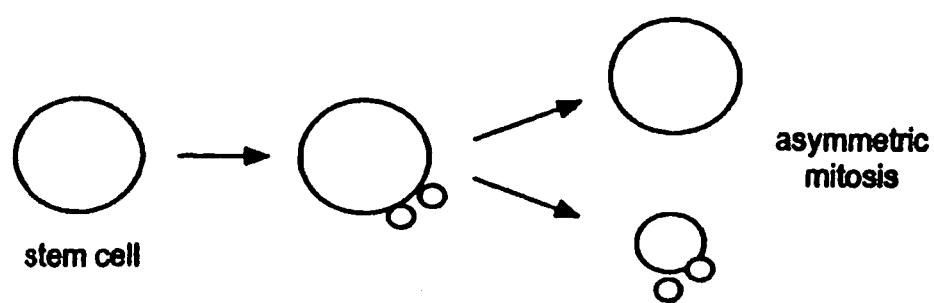
Figure 5B:
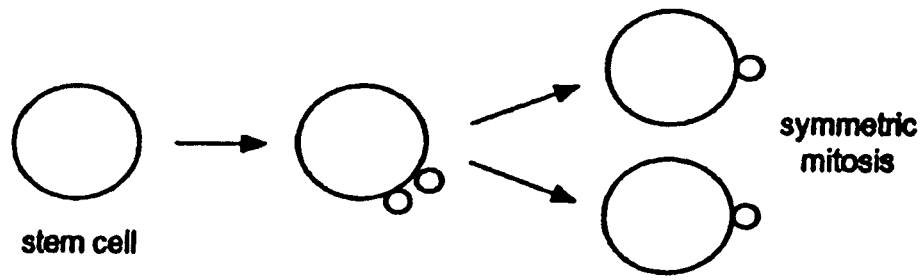

FIGS. 5A and 5B show segregation of certain cellular factors during asymmetric versus symmetric mitosis. Large circles represent individual stem cells, the medium-sized circle represents a differentiated progeny cell of a stem cell, smaller circles represent cellular factors (e.g., but not exclusive to, numb or notch proteins) that are apportioned to daughter cells during mitosis.

FIG. 5A depicts asymmetric mitosis, whereby certain intracellular factors are unequally apportioned to the differentiated daughter cell.

FIG. 5B depicts asymmetric mitosis, whereby the same intracellular factors are equally apportioned to both daughter cells.

FIGS. 6A and 6B depict sparing normal stem cells of toxicity derived from OSES-based induction of symmetric differentiation/apoptosis of a cancer stem line. Large circles represent individual stem cells, the medium-sized circle represents a differentiated progeny cell of a stem cell, smaller circles represent cellular factors (e.g., but not exclusive to, numb or notch proteins) that are apportioned to daughter cells during mitosis. PTF=pre-treatment factor; AMIF=asymmetric mitosis inhibiting factor.

FIG. 6A depicts pre-treatment of normal stem cells and a cancer stem line with PTF (designed to bind a cellular factor apportioned to daughter cells) will result in loss of the PTF by normal stem cells after asymmetric mitosis, and maintenance of the PTF by a cancer stem line after symmetric mitosis.

FIG. 6B depicts subsequent treatment of normal stem cells and a cancer stem line with AMIF will inhibit asymmetric mitosis only in a cancer stem line and not in normal stem cells (since, by design, the AMIF requires the presence of the PTF for function). In this manner induction of differentiation or starvation (not shown in figure) will result in symmetric differentiation and/or apoptosis only of the cancer stem line while sparing normal stem cells.

DETAILED DESCRIPTION OF THE INVENTION

Stem Cells and Cancer

As noted supra, the present invention relates to the realization that the origin of cancer involves the birth and subsequent persistence of a population of slow-growing relatively mutationally-spared cancer cells, i.e., the cancer stem line. Such slow-growing relatively mutationally-spared cancer cells are directly derived from normal stem cells via a one-step switch in mitotic mode, to be described in more detail. It is this origin which explains the growth pattern of a cancer stem line (i.e., like normal stem cells from which it is derived, a cancer stem line is slow-growing but rears a large transit population of highly proliferative cells. It is also these properties of a cancer stem line, inherited directly from normal stem cells, that will determine the novel OSES-based methods to contain it and by doing so to treat human cancer.

Normal adult stem cells are "embryonic-like" remnants of early development which function in adult tissues as founder cells responsible for cell lineage development/-tissue renewal (Potten et al, "A Comparison of Cell Replication in Bone Marrow, Testis, and Three Regions of Surface Epithelium", *Biochim. Biophys. Acta*, 560:281-299 (1979); Wolpert, "Stem cells: a problem in asymmetry", *J. Cell Sci. Suppl.*, 10:1-9 (1988)). These poorly-differentiated immortal cell types reside in well-defined environmental niches localized to the basal layer of renewing tissue types including semi-niferous tubules (in the case of primordial germ cells) as well as epidermis, intestinal crypts, and mammary terminal ducts among others. It is within these sequestered regions that stem cells ensure proper tissue renewal, as described independently by Potten and Wolpert, by maintaining a constant founder cell population while concomitantly replacing aged cells and in doing so creating a local microenvironment wherein maturing/differentiating progeny cells migrate away from a fixed stem cell position (Potten et al, "A Comparison of Cell Replication in Bone Marrow, Testis, and Three Regions of Surface Epithelium", *Biochim. Biophys. Acta*, 560:281-299 (1979); Wolpert "Stem cells: a problem in asymmetry", *J. Cell Sci. Suppl.*, 10:1-9 (1988)).

In some ways this well-defined stem cell microenvironment resembles that of developing embryonic tissues. For example, as adult tissue renewal is fueled ultimately by the production of differentiated cells by an environmentally-sequestered stem cell, a developing embryonic germ layer similarly forms from cellular descendants of a region of spatially confined progenitor cells, in this case at the posterior end of a mammalian embryo. In addition, the local architecture of a developing/renewing adult cell lineage, characterized by progressive migration of maturing stem cell progeny from a fixed stem cell position, resembles that of developing embryonic trophectoderm and endoderm wherein directed movement of cell progeny and consequent alterations in their relations with neighboring tissues results in a restriction of potency (Spemann (ed.), "Embryonic Development and Induction", New York: Hafner, Inc. (1962); Wolpert, "Positional information and pattern formation", *Phil. Trans. Roy. Soc. Lond., Ser B.*, 295:441-450 (1981); Gurdon, J. B. Embryonic induction—molecular prospects, *Development*, 99:285-306 (1987); Gardner et al, "Multilineage 'stem' cells in the mammalian embryo", *J. Cell Sci. Suppl.*, 10:11-27 (1988)).

Based on the observations, it is also theorized that disruption of the well-defined microenvironment of an adult stem cell may have similar consequences to altering the surroundings of an embryonic cell. As will be discussed (and as mentioned earlier), there are several classic experiments which demonstrate that alterations to the surroundings of a developing embryonic tissue can result in aberrant development and "neoplasia" (Rubin, "Cancer as a Dynamic Developmental Disorder", *Cancer Res.*, 45:2935-2942 (1985); Pierce et al (eds.), "Cancer: a problem of development biology", New Jersey: Prentice Hall Inc. (1978)). Accordingly, it is theorized here that the disturbance of the local environment of a stem cell (in manners to be discussed) could, in a similar way to disrupting an embryonic environment, predispose potent cell types (i.e., stem cell in is case) to aberrant development and "neoplasia". An examination of some of the recently-described molecular mechanisms by which embryonic and adult cell lineages normally develop as well as some of the potential mechanisms by which they can go awry supports this theory.

During embryogenesis, one role of the surrounding spatial architecture of developing tissues is to act as a dynamic scaffold that directs differentiation, morphogenesis, and fulfillment of a proper developmental plan (Spemann (ed.), "Embryonic Development and Induction", New York: Hafner, Inc. (1962); Wolpert, L., Positional information and pattern formation, Phil. Trans. Roy. Soc. Lond., Ser B., 295: 441-450 (1981); Gurdon, "Embryonic induction—molecular prospects", *Development*, 99:285-306 (1987); Gardner et al, "Multilineage 'stem' cells in the mammalian embryo", *J. Cell Sci. Suppl.*, 10: 11-27 (1988)). Mechanistically, it had been previously suggested by Holtzer that developing embryonic cells might limit their potency and differentiate, when surrounded by a proper inducing environment (i.e., scaffolding), via a switch from symmetric to asymmetric mitotic division leading to formation of differentiated cell types (Stamatoyannopoulos et al (eds.), "Globin Gene Expression and Hematopoietic Differentiation", pp. 213-227. New York: A. R. Liss, Inc. (1983)).

There is now indeed strong evidence that certain key developmentally-regulated cell fate decisions during embryogenesis are mediated specifically by a timely switch from symmetric to asymmetric mitotic division. This process has been likened to a highly conserved one-step epigenetic mitotic switch, as described by Herskowitz, that regulates vegetative growth in lower eukaryotes (Horvitz et al, "Mechanisms of Asymmetric Cell Division: Two Bs or Not Two Bs, That is the Question", *Cell*, 68: 237-255 (1992)). Mechanistically, a variety of intracellular proteins (e.g., NOTCH and m-NUMB) have been found to be unequally segregated to daughter cells at asymmetric mitosis during mammalian development. These findings coupled with the demonstration that equal segregation or, alternatively, loss of expression of these and other related factors can lead to a switch in mitotic mode from asymmetric to symmetric division strongly indicates a causal role (by preferentially segregated intracellular factors) in determining the fate of their host cell. Moreover, the proper apportioning of such intracellular factors has been shown to be affected by certain extrinsic locally-acting factors and their downstream signaling pathways thereby providing molecular support for past proposals that morphogenesis is dependent on a proper surrounding environment (i.e., scaffold) wherein intercommunication between developing embryonic cell types occurs, e.g., presumably by triggering a switch from symmetric to asymmetric embryonic cell mitosis (Lin et al, "Neuroblasts: a model for the asymmetric division of stem cells", *Trends Genet.*, 13: 33-39 (1997); Wolpert, "Positional information and pattern formation", *Phil. Trans. Roy. Soc. Lond, Ser B.*, 295: 441-450 (1981)). It would follow from this idea that disruption of the surrounding environment of developing embryonic cells (e.g., via ectopic transplantation of embryonic cells out of their native environment) would disturb developmentally-regulated local induction of asymmetric embryonic cell mitosis which in turn could allow such developing cells to continue to proliferate via symmetric mitosis (i.e. exponentially)—an aberrant process which would resemble "neoplasia".

As previously mentioned, when embryonic ectoderm is ectopically transplanted to adult tissues it can form a neoplasm (i.e., teratocarcinoma) which then regressed if replaced back into the embryonic milieu of a developing blastocyst (Pierce et al (eds.), "Cancer a problem of developmental biology", New Jersey: Prentice Hall Inc. (1978)). By conventional models, one might have to invoke mutation-selection to create this neoplasm followed by a enigmatic "bypassing" of such permanent genomic derangements to account for its reversibility. However, consider an alternative novel explanation whereby placement of ectodermal cells into a foreign tissue milieu results in an interruption of native signals that normally induce them to undergo asymmetric mitosis thereby leading to persistence of symmetric mitoses, i.e., effectively a one-step-epigenetic switch (OSES) from asymmetric to symmetric embryonic cell mitosis, resulting in symmetric mitoses out of proportion to asymmetric mitoses, a net proliferation of misplaced embryonic cells, and a disorderly/neoplastic (e.g., "teratocarcinomatous") phenotype. In this manner, the reversibility of certain teratocarcinomas upon placement into blastocysts, rather than reflecting a "bypass"

of permanent mutations, could indicate that this tumor is no more than a collection of misplaced ectodermal cells which maintain a capability to resume proper morphogenesis upon restoration of endogenous differentiation-inducing signals (because they did not amass mutational changes and thus did not need to bypass any). Assuming embryonic and adult tissue development are mechanistically related processes, as allude to, then disruption of the latter process (e.g., via carcinogen-induced tissue damage), like disturbance of the former (e.g., via ectopic transplantation) might also lead to aberrant epigenesis and neoplasia via a similar mechanism.

Figure 1A:
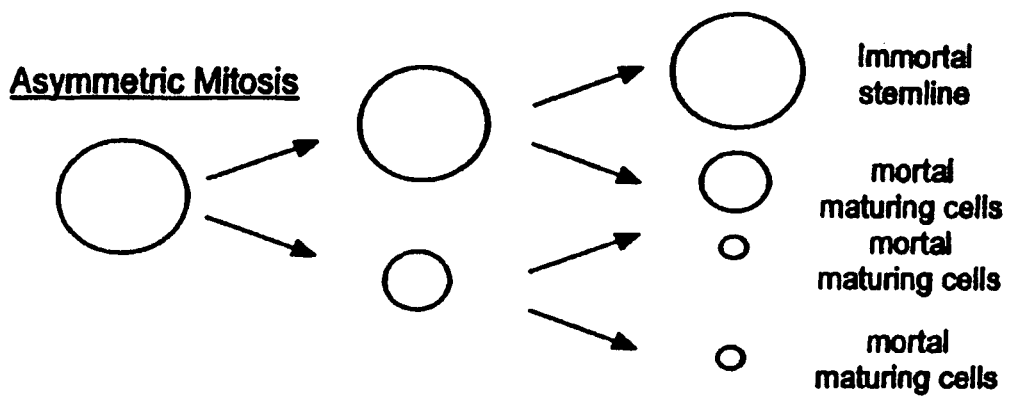

Like their developing embryonic counterparts, there is evidence that adult stem cells act via a similar asymmetric mitotic process which also relies on a signaling pathway induced by extrinsic cues derived from neighboring cells (and/or extracellular matrix) (Lin et al, "Neuroblasts: a model for the asymmetric division of stem cells", *Trends Genet.*, 13: 33-39 (1997); Potten et al, "A Comparison of Cell Replication in Bone Marrow, Testis, and Three Regions of Surface Epithelium", *Biochim. Biophys. Acta*, 560: 281-299 (1979); Wolpert, "Stem cells: a problem in asymmetry", *J. Cell Sci. Suppl.*, 10: 1-9 (1988)). However, in contrast to the relatively "loose" architectural arrangement of developing embryonic tissue and seemingly stochastic manner by which developing embryonic cells asymmetrically produce less potent progeny that differentiate, the well-defined microenvironmental stem cell niche may make stem cells subject to a relatively more continual flow of extrinsic inducing signals thereby regulating in a relatively less stochastic process characterized by regular asymmetric mitoses at the completion of each and every stem cell cycle. (See FIG. 1A)

Figure 1B:
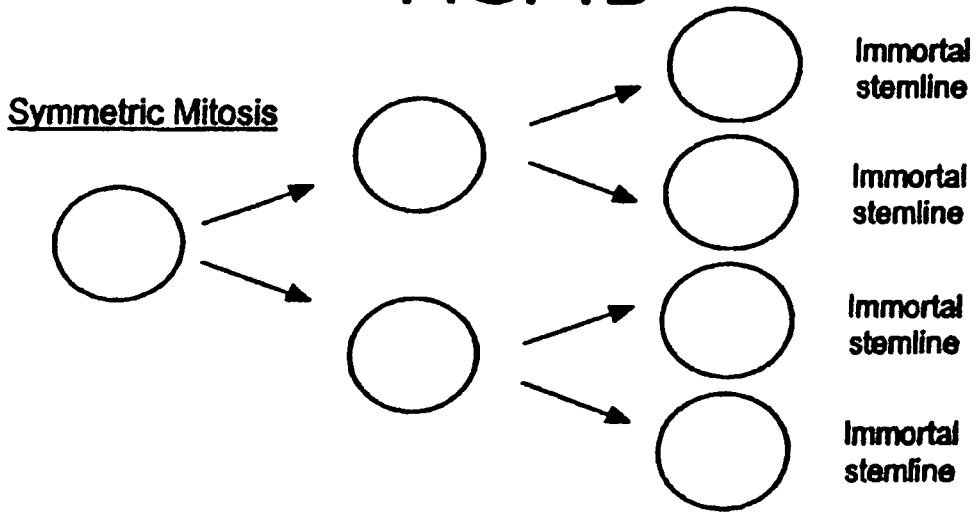

Thus, by this model, despite the clear architectural difference between embryonic and adult tissues, the processes of embryogenesis and adult tissue renewal can still be analogous and driven by similar mechanisms (i.e., symmetric and timely asymmetric mitoses). Accordingly, disturbance of an embryonic milieu (e.g., due to ectopic ectodermal cell transplantation) will result in tumor formation due to maintenance of an embryonic phenotype arising from a preponderance of symmetric embryonic cell mitoses. Similarly, disruption of a stem cell microenvironment would also lead to neoplastic growth arising from persistence of a stem cell phenotype due to continued symmetric stem cell mitoses. More specifically, disturbance to the regular flow of local inducing signals necessary for ensuring regular asymmetric stem cell mitoses, a disturbance arising possibly from carcinogen-induced damage of a developing stem cell milieu (a microenvironment which consists largely of non-stem cells responsible for providing such inducing signals to their stem cell neighbors) will result in disruption of this normally tightly-controlled process thereby leading effectively to a one-step epigenetic switch (OSES) from asymmetric to symmetric stem cell mitoses. (See FIG. 1B)

It also follows from such a model that symmetrically-dividing stem cells "crowded" within a stem cell niche would be correspondingly subject to local inducing signals which normally only affect the fate of a single sequestered stem cell. In this manner, symmetrically-dividing stem cells would in effect "overload the system" (i.e., too many cells and not enough differentiation-inducing signals) thereby causing them to adopt a more stochastic mode of differentiation-induction characteristic of developing embryonic tissues. Accordingly, the timing of induction of asymmetric stem cell mitosis within a disrupted milieu would no longer be regular thereby potentially leading to net proliferation, unplanned differentiation, and a disorderly-appearing tissue mass. By this model, the phenotype of symmetrically-dividing adult stem cells, of the germline as an example (i.e., primordial germ cells), would approximate the teratocarcinomatous appearance proposed for symmetrically-dividing ectodermal cells when ectopically transplanted thereby obviating the need to invoke a multi-step evolutionary process in the birth of this tumor from primordial germ cells. In this manner, the unstructured histopathologic phenotype characteristic of early solid tumors could represent pre-existing cancer cells and their irregularly-differentiating progeny rather than a collection of "pre-cancerous" intermediates. Accordingly, symmetrically-dividing adult stem cells are synonymous with cancer cells.

Interestingly, there is evidence that stem cells are the cell type of origin for a variety of hematologic as well as solid malignancies which begs the question as to how many more alterations would be required by stem cells, which are already poorly-differentiated and "immortal", to assume a neoplastic phenotype? It had been previously described by Pierce that certain cancer cell types were no less differentiated at the histopathological level than stem cells from their corresponding lineages of origin. In addition, the renewal rates of a variety of developing tissues known to harbor stem cells (e.g., bone marrow, gastrointestinal tract, and testis) have been reported to be comparable to the exponential growth rates of corresponding cancer cell types derived from these tissues (Sell et al, "Maturation Arrest of Stem Cell Differentiation as a Common Pathway for the Cellular Origin of Teratocarcinomas and Epithelial Cancers", *Lab. Invest.*, 70:6-22 (1994)); Pierce et al (eds.), "Cancer: a problem of development biology", New Jersey: Prentice Hall Inc. (1978)). Based on these mentioned findings it appears that the major difference between a stem cell and a cancer cell arising from the same tissue of origin is the mode by which these two poorly-differentiated immortal cell types divide (i.e., asymmetric mitosis leading to arithmetic cellular growth vs. symmetric mitosis leading to exponential cellular growth, respectively), an epigenetically-derived trait.

Since there is evidence that the developmental decision to switch from symmetric to an asymmetric mitotic mode can occur in one-step via an epigenetically-controlled mechanism (Horvitz and Herskowitz, "Mechanisms of Asymmetric Cell Division: Two Bs or Not Two Bs, That is the Question", *Cell*, 68:237-255 (1992)), multiple mutational derangements are likely unnecessary for an aberrant switch from the latter to the former to occur in developing adult tissues (i.e., stem cells). Comparison of the respective genomes and expression profiles of stem cells and cancer cells using conventional molecular biological techniques (e.g., subtraction hybridization) will allow one to more accurately substantiate the noted gross (morphological and mathematical) similarities between these cell types.

Support for the proposed OSES model can be sought by experimentally inducing stem cells to divide symmetrically and observing whether the resultant phenotype resembles neoplasia. Since the phenotype of a stem cell is usually described in the context of arithmetic cell division leading to orderly tissue renewal without a net increase in cell number (i.e., asymmetric mitosis) it has not yet been shown what consequences would arise if the phenotype of a stem cell were to persist in both of its daughter cells (i.e., symmetric mitosis). If local extrinsic signals are responsible for ensuring regular asymmetric stem cell mitoses then one might have to experimentally disperse stem cells from their sequestered niches in order to examine a true stem cell phenotype without environmental influence. Namely, dissection of certain adult stem cells out of their well-defined microenvironments, according to the OSES model, should result in loss of local inductive signals required for asymmetric stem cell mitosis (as with transplanted embryonic cells) thereby leading to a switch to symmetric stem cell mitoses and tumor formation. In addition, experimental reimplantation of such a lesion back into its native stem cell microenvironment should effect carcinogenic reversion and resumption of normal lineage development—a phenomenon previously demonstrated for teratocarcinomas (Pierce et al (eds.), "Cancer: a problem of development biology", New Jersey: Prentice Hall Inc. (1978)). Stem cells of the hematologic lineage have been successfully purified using various monoclonal antibody techniques thereby making the proposed experiments feasible at least for the hematopoietic system (Uchida et al, "Heterogeneity of hematopoietic stem cells", Curr. Opin. Immunol., 5: 177-184 (1993). There has also been some success in transplanting stem cells of non-hematologic tissues (e.g., intestinal epithelium) but purification of these cells awaits further technical improvements (Gordon, "Differentiation and self-renewal in the mouse gastrointestinal epithelium", Curr. Opin. Cell Bio., 6: 795-803 (1994)). Antigens and other specific gene products differentially expressed by stem cells and their differentiated progeny in a variety of different cell types are being identified at an ever-increasing pace (e.g., integrins in developing skin) and could act as potential molecular targets for the purpose of separating stem from non-stem cells in preparation for transplantation to test the OSES model (Sigal, "The liver as a stem cell and lineage system", Am. J. Physiol., 263: G139-G148 (1992); Jones et al, "Stem Cell Patterning and Fate in Human Epidermis", Cell, 80: 83-93 (1995)).

Closer examination of some previous reports of tumor formation that follows ectopic transplantation of certain adult tissues (e.g., pituitary and testis) to foreign tissue locales should confirm (or deny) through utilization of more current techniques that the neoplasms that arise from such transplants are derived specifically from the stem cells of these tissues as would be predicted by the OSES model (Rubin, "Cancer as a Dynamic Developmental Disorder", Cancer Res., 45:2935-2942 (1985); Faber and Rubin, "Cellular Adaptation in the Origin and Development of Cancer", Cancer Res., 51:2751-2761 (1991)). Moreover, experimental retransplantation of these tumors back within the confines of the stem cell microenvironments of their respective tissues of origin should confirm whether recreation of normal cell lineage development, as predicted by the OSES model, can occur.

In summary, by the OSES model, as discussed, cancer "initiation" is caused by (e.g., carcinogen-induced) damage to a developing stem cell milieu, and more specifically from damage to those (non-stem) cells that normally induce their stem cell neighbors to undergo regular asymmetric mitoses. Since a considerable proportion of the non-stem cells which surround a stem cell are a stem cell's own progeny, might damage specifically to this particular cell population lead indirectly to a stem cell-derived cancer? In this manner, perpetuation of a mutant differentiation-related gene by a stem cell to its non-stem cell progeny (but not expressed in a stem cell which does not itself differentiate) could lead to aberrant cell differentiation (due to expression of a mutant differentiation-related genes in differentiating cells) and an disrupted stem cell microenvironment (due to aberrantly differentiating cells within the milieu). This scenario in turn like that of embryonic cells placed in a foreign milieu, will permit developing (stem) cells to become neoplastic by predisposing them to symmetric mitoses. It follows from this idea that germline inheritance of certain mutant differentiation-related genes (e.g., TP53, RB-1, BRCA-1) might lead to a novel non-neo-Darwinian manner in which to endow a cancer predisposition whereby such genes adversely affect the differentiation capabilities of non-stem cells thereby predisposing neighboring stem cells to symmetric mitoses. Evidence that an inherited cancer predisposition can be affected by mutagenic effects on (non-neoplastic) cells which neighbor a neoplasm is provided by Varmus' group wherein some mammary tumors derived from germline TP53/Wnt-1 altered mice may be more aggressive when surrounded by p53−/− cells than by "less-mutated" p53+/− cells (Donehower et al, "Deficiency of p53 accelerates mammary tumorigenesis in Wnt-1 transgenic mice and promotes chromosomal instability", Genes Dev., 9: 882-895 (1995)). However, are these proposals by the OSES model also consistent with well-corroborated data correlating mutagenesis with the latter "progression" phase of cancer development?

Along similar lines, if symmetrically-dividing stem cells (i.e., cancer cells) are susceptible to local differentiation-inducing signals (which would induce tumor regression) then how could a mass of such cells continue to grow in size and eventually invade, i.e., "progress" rather than regress?

Tumor Progression

It is a well-documented phenomenon that most tumor types evolve at the tissue level from a "benign-appearing" to an increasingly "cancerous-appearing" lesion (Furth, "Conditioned and autonomous neoplasms: a review", Cancer Res., 13: 477-492 (1953); Foulds, "The natural history of cancer", J. Chronic Dis., 8: 2-37 (1958)). This metamorphosis could in theory result from either the stepwise evolution of increasingly cancerous cellular intermediates (i.e. conventional model) or alternatively from the gradual emergence in numbers of a subpopulation of cancer cells created via a one-step non-evolution press (i.e. the OSES model). The correlation between mutational accumulation and tumor "progression" at the tissue level has been cited in support of the former idea (Weinberg, "Oncogenes, Anti-oncogenes, and the Molecular Basis of Multistep Carcinogenesis", Cancer Res., 49: 3713-3721 (1989); Nowell, "The Clonal Evolution of Tumor Cell Populations.", Science (Washington D.C.), 194: 23-28 (1976)). Additional support for neo-Darwinian cellular evolution has arisen from recent high resolution molecular analyses of human tumor biopsy specimens revealing that adjoining "pre-cancerous" and "cancerous" tumor regions can share certain rare mutational alterations—findings cited as evidence for a direct lineage from a "benign" cell to a "cancerous" one. Moreover, demonstration of the presence of certain unique genetic alterations solely within "cancerous" portions of a tumor has been interpreted as further evidence of a causal role for mutation in effecting the cellular transition from "benign" to "malignant" (Fearon and Vogelstein, "A Genetic Model for Colorectal Tumorigenesis", Cell, 61:749-767 (1990); Sidransky et al, "Clonal expansion of p53 mutant cells is associated with brain tumor progression", Nature (Lond.), 355:846-847 (1992)).

However, these mentioned observations cited in support of neo-Darwinian cellular evolution are also consistent with the OSES model. Namely, while the presence of a rare mutation within both a "benign-appearing" and an adjoining "cancerous-appearing" portion of a tumor may be interpreted as evidence for conventional neo-Darwinian evolution at the cellular level, this is not the only explanation for such a finding. Rather, the sharing of a rare mutation by adjacent tumor regions may merely reflect a common ancestry for cells within such neighboring sites without definitively revealing which cells arose from which. Accordingly, a reverse temporal scenario to that of conventional mutation selection but consistent with the OSES model is possible whereby a direct lineage between cells within adjacent "benign" and "cancerous" tumor regions is maintained but via reversion of "cancerous" cells into "benign" ones (e.g., via cancer cell differentiation), rather than via progression of the latter to the former. In this way, mutations present in adjoining "benign" and "cancerous" tumor regions would be considered essentially "neutral", i.e., not adversely affecting the ability of cancer cells to differentiate. In a related manner, detection of unique mutations solely within a "cancerous" region of a tumor, although cited in support of conventional mutation-selection, is also consistent with the OSES model which explains these genetic alterations as acquired features of pre-existing cancer cells rather than as effectors of "progression" toward malignancy. Thus, such mutations present solely within a "cancerous" portion of a tumor would represent selectively advantageous genetic alterations that inhibit cancer cell differentiation/regression into "benign" cells. In this manner, such advantageous mutations might be expected to hasten the emergence of a clone of pre-existing cancer cells from amongst its slowergrowing (i.e. differentiating/regressing) non-mutant neighbors. So the presence of clonal mutant outgrowths in tumors, a finding often cited in support of conventional neo-Darwinian models, is also consistent with the OSES model. In other words, these mentioned tumor-related data alone are insufficient to categorically determine the lineage history of related tumor cell populations and thus do not rule out the idea of differentiation from "cancerous" to "benign" (i.e., the OSES model). Accordingly, higher resolution lineage analyses, comparing respective tumor regions using multiple independent cellular markers, may be required to better discern between these two divergent accounts.

By the OSES model then the phenomenon of tumor "progression" would correspond to a gross histopathologic change due to the gradual emergence of pre-existing cancer cells rather than the stepwise selection of individual "pre-cancerous" intermediates. The preferential outgrowth of a clone(s) of cancer cells from amongst its slower-growing (i.e. differentiating/regressing) neighbors could then be attributed to the advantageous acquisition of mutations which inhibit that mutant clone's ability to differentiate. More specifically, by the OSES model peripherally-located cancer cells in a tumor mass may be the most susceptible population to selective pressure for differentiation-impairing mutations thereby effectively "shielding" the more centrally-located cancer cells of such pressures (and thus of significant mutational accumulation). Accordingly, expansion of peripherally-located mutants which are differentiation-defective (and which may or may not have a limited proliferative capability) might further shield a more centrally-located subpopulation thereby allowing it to expand and act as an "immortal" founder line (i.e. cancer stem line) that is relatively mutationally-spared. This idea is consistent with reports that certain human tumors (e.g., breast carcinomas) have a higher histopathological grade in their more central regions as well as with findings that some highly aneuploid tumor types have a chromosomal distribution pattern best accounted for by the presence of a stem line which is near-euploid (Lennington et al, "Ductal carcinoma in situ of the breast. Heterogeneity of individual lesions", *Cancer*, 73:118-124 (1994); Makino, "Further Evidence Favoring The Concept of the Stem Cell In Ascites Tumors Of Rats", *Ann. N.Y. Acad. Sci.*, 63:818-830 (1956); Shapiro et al, "Isolation, Karyotype, and Clonal Growth of Heterogeneous Subpopulations of Human Malignant Gliomas", *Cancer Res.*, 41:2349-2357 (1981)). If some mutations could affect tumor growth behavior subsequent to the birth of a cancer cell (e.g., by inhibiting cancer cell differentiation) then another potential non-neo-Darwinian explanation for an inherited cancer predisposition (in addition to predisposing to the early "initiation" stage of cancer by causing non-stem cells to aberrantly differentiate) might also derive from germline inheritance of a mutant gene that accelerates the latter "progression" stage of cancer by thwarting differentiation/reversion of cells which are already cancerous.

It should be noted that it had been previously described by Pierce that certain malignant cell types including neuroblastoma, leukemia, rhabdomyosarcoma, and mammary adenocarcinoma are capable of "differentiating" into benign tissues. Namely, classic experiments involving thymidine labeling of rat squamous cell carcinomas and single cell cloning of murine teratocarcinomas revealed that the poorly-differentiated cells within these particular tumor types had given rise to well-differentiated tumor cells but not vice versa (i.e., not via dedifferentiation). It was further shown in these experiments that the poorly-differentiated cells within these neoplasms were the cell types responsible for tumor growth and invasion while their well-differentiated progeny had essentially lost malignant growth potential and were thus deemed to be "benign" (Pierce et al (eds.), "Cancer: a problem of development biology", New Jersey: Prentice Hall Inc. (1978)). A question not adequately addressed at the time but which may be able to be evaluated by current molecular techniques is whether the "benign" cells within these particular experimental rodent tumors are analogous to those "benign" cells normally classified as "pre-cancerous" in human tumors. In other words, as hypothesized here, cells within a "benign-appearing" region of human tumors may actually constitute differentiated progeny of pre-existing cancer cells rather than "pre-cancerous" intermediates. Re-exploration of these mentioned early experiments with current molecular biological techniques should elucidate whether rodent tumors previously shown to harbor evidence of cancer cell differentiation also possess a mutational distribution similar to that described for human neoplasms—a distribution that has been attributed to conventional mutation-selection. Detection of a similar mutational distribution should provide further evidence that the OSES model (which invokes cancer cell differentiation) provides an equivalent explanation as neo-Darwinism for the presence of "benign-appearing" cells within human cancers—and a better explanation than conventional models for cases of epigenesis in carcinogenesis (as argued previously).

It is also noted that there are cases in which cancer-related mutations do not clearly accumulate with tumor "progression". Such data have not been readily accounted for by conventional models, but when analyzed more closely, are indeed consistent with the predictions of the OSES model.

Mutational Accumulation Without "Progression"

As mentioned, the well documented correlation between mutational accumulation and cancer development might in theory be accounted for by more than one model (i.e. neo-Darwinism or OSES). However, there also exists data of a different type wherein mutational accumulation does not always proceed in sync with the early stages (i.e. "initiation") or latter stages (i.e. "progression") of cancer development. Such findings, as will be described in part, are difficult to reconcile by a classical neo-Darwinian paradigm which, by definition, invokes selection as the primary explanation for the presence, in large numbers of cells, of mutations that would otherwise be rarely found.

For example, there are some newly described enigmatic cancer-related phenomena wherein the presence of detectable mutations at an early stage of cancer development does not always signify "selection". Namely, a variety of genomic alterations have been detected not only in cancer cells but surprisingly also in synchronous histologically normal cells of the same tissue type (e.g., loss of heterozygosity (LOH) of WT-1 or hypermethylation of H19 in kidney, LOH of breast cancer-related loci in mammary gland, and mutator phenotype (MP) defects in colon) (Parsons et al, "Mismatch Repair Deficiency in Phenotypically Normal Human Cells", *Science* (Washington D.C.), 268: 738-740 (1995); Chao et al, "Genetic mosaicism in normal tissues of Wilms' tumor patients", *Nature Genet.*, 3: 127-131 (1993); Moulton et al, "Epigenetic lesions at the H19 locus in Wilms' tumor patients", *Nature Genet.*, 7: 440-447 (1994). Deng et al, "Loss of Heterozygosity in Normal Tissue Adjacent to Breast Carcinomas", *Science* (Washington D.C.), 274: 2057-2059 (1996)). By conventional models, rare mutations become detectable predominantly by selection alone. Accordingly, the data mentioned above provide somewhat of a paradox for conventional thinking which considers detectable mutations by definition to be selectively advantageous, and that those non-neoplastic cells harboring such genetic changes should therefore display some evidence of "overgrowth" histopathology—a prediction which is not supported by these mentioned studies. These findings are, however, consistent with the OSES model which predicts that mutations act in "initiation" not by accumulating in and promoting growth of future cancer cells (i.e. stem cells) but rather by causing genetic changes in neighboring non-stem cells which impair their differentiation capability—a process that in turn leads to an altered tissue milieu predisposing to symmetric stem cell mitoses. In this manner, there should be a lag period characterized by detectable mutagenesis (followed by aberrant differentiation) before any histopathologic evidence of proliferative activity is evident. This scenario predicted by the OSES model, unlike the one predicted by conventional models, is consistent with the mentioned studies.

In a related manner, there are several other reports, as alluded to, wherein mutations also do not entirely correlate with the latter stages cancer evolution. For example, a subset of human colorectal tumors possess functional alterations at some cancer-related loci (e.g., c-K-RAS or TP53) in "benign" but surprisingly not in adjacent "cancerous" regions (Shibata et al, "Genetic Heterogeneity of the c-K-ras Locus in Colorectal Adenomas but not in Adenocarcinomas", *J. Natl. Cancer Inst.*, 85: 1058-1062 (1993); Ohue et al, "A Frequent Alteration of p53 Gene in Carcinoma in Adenoma of Colon", *Cancer Res.*, 54: 4798-4804 (1994); Kaklamanis et al, "p53 Expression in Colorectal Adenomas", *Am. J. Path.* 142: 87-93 (1993)). Similarly, LOH at various loci have been detected in pre-invasive but not adjoining invasive regions of a subset of human breast carcinomas (O'Connell et al, "Molecular genetic studies of early breast cancer evolution", *Breast Cancer Res. Treat.*, 32: 5-12 (1994)). In a related manner, a subset of primary gastric tumors with mutant TP53 display only wildtype TP53 at metastatic foci (Strickler et al, "p53 Mutations and Microsatellite Instability in Sporadic Gastric Cancer: When Guardians Fail", *Cancer Res.*, 54: 4750-4755 (1994)). By the OSES model, "cancerous" cells could, upon induction by local differentiation-inducing signals (as mentioned in the previous section) pass on a "neutral" mutation to a large population of its "benign" progeny. This idea would explain the seemingly enigmatic presence of certain mutations in a "less-cancerous" region but not in a correspondingly "more-cancerous" region. By conventional thinking, however, one may have to infer from these data that either cells within "more-cancerous" regions had not arisen from ones within "less-cancerous" regions, or that neoplastic cells wild-type at a given locus had somehow out-competed their corresponding mutant. By either of these explanations, the classic clonal selection hypothesis by Nowell is violated (Nowell, "The Clonal Evolution of Tumor Cell Populations", *Science* (Washington D.C.), 194: 23-28 (1976)). Accordingly, in an effort to maintain a neo-Darwinian model, one may have to speculate that a "surreptitious" mutator phenotype (MP)-like mechanism may have acted in a (seemingly wild-type) clone to enable its selection over detectably-mutant competitors—an idea which awaits experimental support. However, while combining conventional genetic alterations (e.g., in c-K-RAS or TP53) with an MP-like mechanism might appear to provide an adequate neo-Darwinian explanation for these data, this idea clashes with observations that these distinct mutational mechanisms usually do not coexist within the same tumor (Perucho, "Microsatellite instability: The mutator that mutates the other mutator", *Nature Med.*, 2: 630-631 (1996). Accordingly, conventional neo-Darwinian models do not adequately account for these mentioned cases—cases which are more completely explained by the OSES model.

A discussion of some of the testable differences between the OSES and conventional models is set forth below.

Testable Differences Between the OSES and Conventional Cancer Models

There are a number of testable differences between the OSES model and conventional cancer models. Some of these differences are discussed below.

The expression profile of a stem cell is inherited en bloc by a cancer cell. Based on the proposal that a one-step epigenetic switch (OSES) from asymmetric to symmetric stem cell mitosis is responsible for the birth of a cancer cell, it follows from such a model that cancer cells will inherit an expression profile largely en bloc from stem cells. In this manner, the expression profile of a cancer cell will be generally the same as that for a stem cell, i.e., no major epigenetic or mutational alterations will be incurred, with the caveat that a stem cell by virtue of its environmental sequestration passes its phenotypic state on to only one of its daughter cells via asymmetric mitosis whereas a cancer cell (i.e., symmetrically-dividing stem cell) passes its inherited stem cell phenotypic state on to both daughter cells via symmetric mitosis unless extrinsically induced to transiently divide asymmetrically by local signals. In contradistinction to previously described epigenetic models as well as current neo-Darwinian models for cancer which each invoke a stepwise accumulation of heritable cellular alterations in the evolution of a cancer cell, the OSES model depicts the cancer cell phenotype not as a collection of mutational and/or epigenetic traits acquired in a stochastic piecemeal fashion but rather as a state inherited directly from a stem cell precursor in one step without the need for further changes (Holliday, "A New Theory of Carcinogenesis", *Br. J. Cancer*, 40-513-522 (1979); Rubin, "Cancer as a Dynamic Developmental Disorder", *Cancer Res.*, 45:2935-2942 (1985); Vogelstein et al, "The multistep nature of cancer", *Trends Genet.*, 9:138-141 (1993)).

Differentiation-Related Genes are Inherited by Cancer Cells from Stem Cells Largely in an Epigenetically Down-Regulated State.

Genes which do not function in maintenance of the stem cell phenotype (e.g., genes involved in enactment of differentiation/asymmetric mitosis) are likely to be normally down-regulated in stem cells during most of their cell cycle until G1-S at which time they become up-regulated in preparation for asymmetric production of differentiated progeny (Villarreal "Relationship of Eukaryotic DNA Replication to Committed Gene Expression: General Theory for Gene Control", *Microbiol. Rev.,* 512-542 (1991)). Therefore, according to the OSES model differentiation-related gene complexes will be inherited by cancer cells from stem cells en bloc in an epigenetically down-regulated state. In this manner, stochastic acquisition by cancer cells of mutations to differentiation-related loci would not initially be expected to endow them with any particular selective advantage (or disadvantage) since these gene complexes should be down-regulated/unexpressed anyway. However, by the OSES model, if a cancer cell was subsequently extrinsically induced by local signals to asymmetrically produce differentiated progeny then its differentiation-related genes would be predicted to become transiently up-regulated. If these genes had been significantly mutationally damaged while unexpressed then subsequent up-regulation of such mutant genes upon enactment of a proper differentiation program would lead to a defective differentiation capability thereby endowing such mutant cancer cells with a selective growth advantage over their differentiating neighbors.

There is evidence in support of these proposals, i.e. that a cancer cell expression profile is inherited en bloc from a stem cell and that differentiation-related pathways in particular are inherited by a cancer cell from a stem cell in a down-regulated state. For example, there are a number of reports indicating that certain gene complexes, namely those involved in differentiation, may be largely down-regulated in stem cells for the majority of their cell cycle (Wolpert, L., Stem cells: a problem in asymmetry, *J. Cell Sci. Suppl.,* 10:1-9 (1988); Villarreal, "Relationship of Eukaryotic DNA Replication to Committed Gene Expression: General Theory for Gene Control", *Microbiol. Rev.,* 512-542 (1991)). It follows from the OSES model that a cancer cell should maintain the expression profile of its precursor stem cell and therefore be expected to harbor such gene complexes in their native down-regulated state. Demonstration that certain differentiation-related genes are initially epigenetically down-regulated in both stem cells and cancer cells, then up-regulated during (stem cell or cancer cell) differentiation, and subsequently mutated following the birth of a cancer cell rather than before is consistent with and strongly supportive of a temporal scenario predicted by an OSES model for carcinogenesis.

The OSES cancer model can be further substantiated by studying differentiation-related gene complexes, e.g., TS suppressor gene complexes. There is evidence that several tumor suppressor genes (TS's), i.e., genes notoriously found mutationally inactivated or deleted in cancer cells, may comprise one such group of genes that normally functions in enactment of differentiation/cell lineage development (Schmid et al, "Expression of p53 during mouse embryogenesis", *Development,* 113:857-865 (1991); Kent et al, "The evolution of WT1 sequence and expression pattern in the vertebrates", *Oncogene,* 11:1781-1792 (1995); Cordon-Cardo et al, "Expression of the retinoblastoma protein is regulated in normal human tissues", *Am. J. Path.,* 114:500-510 (1994); Marquis et al, "The developmental pattern of Brca1 expression implies a role in differentiation of the breast and other tissues", *Nat. Genet.,* 11: 17-26 (1995)).

Such investigation would include, e.g., experiments studying whether TS's are largely down-regulated in stem cells (during the majority of their cell cycle); if TS's are initially epigenetically down-regulated in cancer cells (i.e., reflecting a state inherited directly from stem cells); and whether mutational inactivation of TS's in cancer cells occurs subsequent to an initial epigenetically down-regulated state. While the results of any one of these experiments alone might not be sufficient to differentiate between a neo-Darwinian and an OSES model, demonstration of all three conditions in a given tumor would provide strong evidence in support of the validity of an OSES model.

Findings Which Would Support Novel Predictions of OSES Model

1. Are TS's Largely Down-Regulated in Stem Cells?

There is evidence, arising largely from a combination of experimental analyses sought to determine both endogenous TS expression as well as the consequences of loss of TS function, that several TS's can play key roles in directing proper development of embryonic as well as adult tissues. For example, TP53 has been shown to function in normal hematopoiesis, WT-1 in early mesodermal differentiation and kidney development, RB-1 in developing CNS and hematopoietic systems, and BRCA-1 during mammary gland morphogenesis. Moreover, expression level differences in TP53, WT-1, and RB-1 between proliferating precursor cell compartments and their early maturing progeny have led some to propose that timely expression level changes of certain TS's in potent cells may be a prerequisite for the developmentally-controlled switch from proliferation to differentiation (Schmid et al, "Expression of p53 during mouse embryogenesis", *Development,* 113:857-865 (1991); Kent et al, "The evolution of WT1 sequence and expression pattern in the vertebrates", *Oncogene,* 11:1781-1792 (1995); Cordon-Cardo et al, "Expression of the retinoblastoma protein is regulated in normal human tissues", *Am. J. Path.,* 114:500-510 (1994); Marquis et al "The developmental pattern of Brca1 expression implies a role in differentiation of the breast and other tissues", *Nat. Genet.,* 11:17-26 (1995)). It would follow from such a model that if up-regulation of certain TS's and/or their pathways led to enactment of a differentiation program then a native down-regulated state for TS's and/or their pathways would be expected to exist in non-differentiating proliferating cells (i.e., embryonic precursor cells or adult stem cells). That TS's can indeed provoke cell differentiation is an idea supported by certain in vitro studies illustrating that up-regulation of TS's (e.g., TP53) induces (epithelial and hematopoietic) differentiation while expression of mutant TS's (e.g., TP53) can lead to aberrant (thyroid cell) differentiation (Soddu et al, "Wild Type p53 Gene Expression Induces Granulocytic Differentiation of HL-60 Cells", *Blood,* 83:2230-2237 (1994); Battista et al, "A mutated p53 gene alters thyroid cell differentiation", *Oncogene,* 11:2029-2037 (1995); Sherley et al, "Expression of the wild type p53 anti-oncogene induces guanine nucleotide-dependent stem cell division kinetics", *Proc. Natl. Acad. Sci. USA,* 92:136-140 (1995)).

While the mechanism by which either transient or permanent expression level changes of certain TS's and/or their pathways can effect cell differentiation has yet to be determined, there is some preliminary experimental evidence that this process can result from TS-induction of stem cells to produce progeny destined to differentiate via an asymmetric mitotic mechanism. Namely, Sherley et al have recently shown that up-regulation of p53 causes immortalized murine epithelial cells to switch from an exponential to a linear growth pattern. Demonstration that quiescent but viable cell progeny are produced following this switch indicates that adoption of division kinetics characteristic of renewing stem cells, rather than that of cell senescence, might be the most accurate explanation for these findings. Moreover, division history analysis of single p53-induced cells plated at low density demonstrates indeed that a non-random mitotic process (i.e., maintenance of one immortal daughter cell) characteristic of asymmetric stem cell mitosis was responsible for the p53-induced change in cellular growth kinetics (Sherley et al, "Expression of the wild type p53 antioncogene induces guanine nucleotide-dependent stem cell division kinetics", *Proc. Natl. Acad. Sci. USA,* 92:136-140 (1995)).

Related experiments using inducible constructs of additional TS's should determine whether or not enactment of asymmetric mitosis is a common mechanism of action for these genes. In addition, temporal and spatial localization of TS gene products in renewing tissues may ultimately determine whether these genes function specifically as inducers of asymmetric stem cell mitosis in vivo as predicted by the OSES model. By such a model, TS expression level changes would be expected to be detectable at the interface between renewing stem cells and early maturing stem cell progeny with or without maintenance of this expression level change in late maturing cells. Interestingly, up-regulation of p53 expression has been detected predominantly during early differentiation events of mouse embryogenesis and decreased during terminal differentiation (Schmid et al, "Expression of p53 during mouse embryogenesis", *Development,* 113:857-865 (1991)). In addition, WT-1 is expressed in mesenchymal stem cells and immature epithelial cells during vertebrate development and largely down-regulated in maturing progeny (Kent et al, "The evolution of WT1 sequence and expression pattern in the vertebrates", *Oncogene,* 11: 1781-1792 (1995)). Similarly, RB-1 expression is also confined to distinguishable compartments in developing adult tissues (Cordon-Cardo et al, "Expression of the retinoblastoma protein is regulated in normal human tissues", *Am. J. Path,* 114:500-510 (1994)). Namely, cells of stratified epithelia display pRB expression in maturing suprabasal layers whereas the basal layer shows lower expression levels (Cordon-Cardo, C., and Richon, V. M. Expression of the retinoblastoma protein is regulated in normal human tissues, *Am. J. Path.,* 114:500-510 (1994)). Further elucidation of the downstream molecular elements leading to TS-induced changes in cell growth kinetics should confirm whether the action of certain TS's involves a one step switch in mitotic mode.

2. Are TS's Initially Epigenetically Down-Regulated in Cancer Cells?

If TS's do normally play a role in maintaining the division kinetics of renewing stem cells in maturing mammalian tissues, then it would follow that TS's and/or their pathways should be largely down-regulated in stem cells during the majority of their cell cycle. Since by the OSES model cancer cells inherit the expression profile of stem cells en bloc, genes which are natively down-regulated in stem cells (e.g., TS's) should be correspondingly unexpressed in cancer cells. While direct evidence for such a proposal remains to be demonstrated, there are a variety of data suggesting that expression of certain TS's and/or their pathways may be altered and in some cases down-regulated in certain tumors without an obvious mutational cause for this. For example, there is a subset of tumors in which epigenetic down-regulation of a wild type TS has been offered as a mechanism to explain the enigmatic presence of loss of heterozygosity (LOH) of a TS accompanied by a seemingly wild type remaining allele (e.g., in the case of TP53, WT-1, and RB-1) (Feinberg, "Genomic imprinting and gene activation in human cancer", *Nat. Genet.,* 2:110-113 (1993)). While definitive evidence for altered expression of wild type WT-1 or RB-1 remains to be demonstrated in these cases, altered p53 protein expression without detectable concomitant somatic TP53 mutation has indeed been described in a variety of human tumor specimens of hematologic, colonic, and pituitary origin. While these results had originally been attributed simply to insufficient TP53 sequence analyses, more rigorous genomic sequencing coupled with the reproducibility of these findings by several independent laboratories indicates that altered regulation of wild type TS expression, at least in the case of TP53, is an actual cancer-related phenomenon for which alternative mechanisms might be required to adequately explain (Ohue et al, "A Frequent Alteration of p53 Gene in Carcinoma in Adenoma of Colon", *Cancer Res.,* 54:4798-4804 (1994); Kaklamanis et al, "p53 Expression in Colorectal Adenomas", *Am. J. Path.,* 142:87-93 (1993)); et al, "p53 gene mutations in pituitary adenomas: rare events", *Clin. Endocrinology,* 41:809-814 (1994); Greenblatt et al, "Mutations in the p53 Tumor Suppressor Gene: Clues to Cancer Etiology and Molecular Pathogenesis", *Cancer Res.,* 54:4855-4878 (1994); Ueda et al, "Functional inactivation but not structural mutation of p53 causes liver cancer", *Nat. Genet.,* 9:41-47 (1995)). Some other possible explanations offered for such findings within the confines of a conventional mutation-selection model include altered splicing or promoter-region mutations causing changes in wild type TP53 expression. While these hypothetical mechanisms certainly remain viable until adequately tested, they do not appear capable of accounting for all cases of cancer-related expression changes in wild type TS's. Namely, while down-regulation of wild type BRCA-1 mRNA has been reported in a number of sporadic human breast cancers, close inspection reveals that both differential splicing and promoter region mutations are unlikely explanations for such findings. Accordingly, it has been proposed that mutational inactivation of a BRCA-1 regulatory gene might be another conceivable explanation, within the boundaries of conventional mutation-selection, for these seemingly enigmatic data (Thompson et al, "Decreased expression of BRCA-1 accelerates growth and is often present during sporadic breast cancer progression", *Nat. Genet.,* 9:444-450 (1995)). However, these findings are precisely those to be expected by an OSES model wherein certain TS's are initially epigenetically down-regulated in cancer cells.

One potential problem with the conventional model which is forced to invoke mutational inactivation of unexamined loci (in this case regulatory genes) prior to actually demonstrating its presence, as with the case of implicating a MP process, is that such notions are virtually impossible to wholly disprove. Accordingly, other models should at least be considered. Namely, epigenetic down-regulation might be another explanation for the finding of an unexpressed wild type TS in certain tumors. This is not the first time such a proposal has been offered (Feinberg, "Genomic imprinting and gene activation in human cancer", *Nat. Genet.,* 2:110-113 (1993)). Namely, reports that alterations in p53 protein accumulation present at the onset of certain early sporadic colonic neoplasms prior to the occurrence of any major mutational damage has led some to invoke a non-mutational mechanism for these p53 expression level alterations (Greenblatt et al, "Mutations in the p53 Tumor Suppressor Gene: Clues to Cancer Etiology and Molecular Pathogenesis", *Cancer Res.,* 54:4855-4878 (1994)). While an epigenetic etiology for a change in TS expression could in theory reflect either a generalized neo-Darwinian or an OSES process, an OSES model would be the favored explanation if epigenetic down-regulation of a given TS was demonstrated in both tumor cell as well as stem cell of the same tissue type, i.e., circumstantial evidence for direct inheritance. Even more convincing for an OSES model would be demonstration that certain TS mutations had occurred subsequent to an initial epigenetically down-regulated state.

3. Does Mutational Inactivation of TS's in Cancer Cells Occur Subsequent to an Initial Epigenetically Down-Regulated State?

By the OSES model, cancer cells are susceptible to reversion via the inducing effects of local "differentiation signals". Therefore, those cancer cells situated at the periphery of a growing neoplastic mass should be most subject to differentiation/reversion and thus more prone to selection for mutant differentiation-defective outgrowths than their more centrally-located counterparts. In this manner, as mentioned, those mutants situated at the periphery of a tumor might effectively "shield" a smaller subpopulation of centrally-located cancer cells from differentiation induction (i.e., selection) thereby allowing such cells to preserve their genetic integrity and thus or the hard evidence for an OSES origin for cancer. Accordingly, there may exist only a small window of opportunity during the initial phases of spontaneous tumor development and only a small centrally-located stem line of cells for which to demonstrate experimentally the prediction by the OSES model that epigenesis precedes mutagenesis.

There is at least one particular experiment which may demonstrate such a related phenomenon. Namely, in liver cancers derived from transgenic mice expressing a single hepatitis B virus (HBV) transgene, the encoded viral protein, HBx, binds p53 protein and prevents its entrance into the nucleus thereby effectively epigenetically down-regulating the p53 pathway. Interestingly, however, is that while analysis of tumor cell DNA derived from early lesions reveals no evidence of p53 mutation (a finding consistent with an epigenetic mechanism for its down-regulation), more advanced lesions do display a small number of cells with acquired TP53 base substitutions, a process which apparently occurred subsequent to an initially epigenetically down-regulated TP53 state (Ueda et al, "Functional inactivation but not structural mutation of p53 causes liver cancer", *Nat. Genet.*, 9:41-47 (1995)). By conventional models, it is not abundantly clear why epigenetic inactivation of a cancer-related gene would be followed by its mutational inactivation during tumor "progression", i.e., why would there be selection for mutational inactivation of a gene which was already (epigenetically) inactivated? One potential explanation consistent with conventional models is that epigenetic inactivation provides an initial growth advantage to cells but is not as absolute as mutational inactivation (Ueda et al, "Functional inactivation but not structural mutation of p53 causes liver cancer", *Nat. Genet.*, 9:41-47 (1995)). However, this idea like that of a MP is difficult to disprove. Moreover, that transdifferentiation of one mature cell type to another is not a common phenomenon in mammals is evidence that epigenetic alterations leading to cell fate decisions is a relatively permanent process in no need of accompanying genomic alterations (Rubin, H., "Cancer as a Dynamic Developmental Disorder", *Cancer Res.*, 45:2935-2942 (1985)). Additional transgenic experiments of the type mentioned above examining other TS's should corroborate preliminary findings that mutational inactivation of a TS can follow epigenetic inactivation. In addition, more intensive molecular analyses of tumor specimens at the RNA level (e.g., by in situ reverse transcription polymerase chain reaction) should better elucidate the temporal relationships between certain mutational and epigenetic events during the early phases of carcinogenesis.

As presented above, there exists a patchwork of preliminary evidence that the expression of certain TS's and/or their pathways may follow the predictions of the OSES model. For example, there is evidence that TP53 functions in adult tissue development as a provoker of differentiation possibly via a cell cycle-coordinated induction of an asymmetric mitotic program in stem cells (Sherley et al, "Expression of the wild type p53 antioncogene induces guanine nucleotide-dependent stem cell divisionkinetics", *Proc. Natl. Acad. Sci. USA*, 92:136-140 (1995)). It follows from these data that TP53 should be largely down-regulated in the native non-dividing state of stem cells. Moreover, there are also findings that alterations in TP53 expression may be present in tumor cells without evidence of a somatic mutation (Ohue et al, "A Frequent Alteration of p53 Gene in Carcinoma in Adenoma of Colon", *Cancer Res.*, 54:4798-4804 (1994); Kaklamanis et al, "p53 Expression in Colorectal Adenomas", *Am. J. Path.*, 142:87-93 (1993); Levy et al, "p53 gene mutations in pituitary adenomas: rare events", *Clin. Endocrinology*, 41:809-814 (1994)). Whether these data reflect an initial inherited down-regulated state for TP53 with subsequent up-regulation and deductibility during cancer cell differentiation rather than a neo-Darwinian "progression" of mutant forms may warrant more intensive molecular dissection to determine whether wild-type TP53 RNA levels positively correlate with decreasing histopathologic grade of a given tumor portion, as would be predicted by an OSES model. In addition, the preliminary evidence that TP53 mutation could potentially follow an initial epigenetic down-regulated TP53 state in some tumors, as illustrated by the HBV transgenic mouse model (Ueda et al, "Functional inactivation but not structural mutation of p53 causes liver cancer", *Nat. Genet*, 9:41-47 (1995)), indicates that this particular prediction of the OSES model is possible. Are other TS's for which evidence suggests a down-regulated state in stem cells (e.g., WT-1, RB-1) and an epigenetically down-regulated state in cancer cells (e.g., BRCA-1) also mutationally inactivated only after an initial epigenetically inactivated state? (Cordon-Cardo et al, "Expression of the retinoblastoma protein is regulated in normal human tissues", *Am. J. Path.*, 114:500-510 (1994); Marquis et al, "The developmental pattern of Brca1 expression implies a role in differentiation of the breast and other tissues", *Nat. Genet.*, 11:17-26 (1995); Thompson et al, "Decreased expression of BRCA-1 accelerates growth and is often present during sporadic breast cancer progression", *Nat. Genet.*, 9:444-450 (1995)). Corroboration of this latter point with future experiments would be strongly supportive of an OSES model for cancer development and difficult for conventional models to reconcile.

Recent neo-Darwinian models have invoked several mechanisms including a MP, mutational inactivation of as yet unidentified/undefined genetic loci (e.g., regulatory genes or promoter regions), and most recently the concept of epigenetic down-regulation not being as absolute as mutational inactivation in order to account for a variety of enigmatic cancer-related findings. However, based on the foregoing, the OSES cancer model provides a more reasonable and logical explanation of carcinogenesis which obviates the inaccuracies and ambiguities associated with prior neo-Darwinian cancer models. Moreover, as mentioned, the OSES model can better account than can conventional models for instances of 1) elevated transformation rates not explained by somatic mutation alone, 2) tumor differentiation and reversibility, and 3) the presence of mutations in both early and late human neoplastic lesions surprisingly without evidence of selection.

OSES-Based Cancer Diagnostic Methods and Therapies

Thus, the present invention provides novel methods for the detection and for the treatment of cancer which are based on the OSES model. The OSES concludes that a clandestine slow-growing relatively mutationally-spared founder line, termed the cancer stem line, (created via a one-step epigenetic switch from asymmetric to symmetric stem cell mitosis and then persistent throughout the life of the tumor) exists within tumors and is responsible for fueling tumor immortality. Like its normal stem cell counterpart (from which it is derived and to which it shares many features), the cancer stem line is slow-growing and rears a transit population of highly proliferative (often mutant) progeny which makes up the bulk of the resulting mass. This transit population in tumors, like in normal tissues, likely has limited proliferative potential (versus its progenitor cancer stem line population which is immortal).

Previous conventional cancer models have focused on the fast-growing highly mutant cell population in tumors. This population is widely believed to have arisen by an evolutionary process involving stepwise mutation-selection at the cellular level. However, such conventional models have not considered the presence of a cancer stem line (of the type proposed by the OSES model)—a significant difference which renders the OSES model and its novel detection methods and therapies for cancer clearly distinguishable from those of conventional cancer models.

Thus, based on the OSES model, the present invention provides 1) novel methods of cancer detection which may detect cancer at an earlier stage than conventional detection methods, as well as 2) novel cancer therapies which may be more apt to cure cancer (i.e. by eradicating its immortal portion) and thereby less prone to relapse than conventional therapies. Conventional methods of cancer detection rely on the presence of relatively large numbers of proliferative cancer cells (e.g., large numbers of cells are necessary to allow detectability by conventional methods such as physical exam, radiologic studies, blood tests, etc.) thereby making cancer detection possible only at a relatively later stage than would be possible by detection methods derived from the OSES model which seeks to identify a small cancer stem line sub-population created early in tumorigenesis. Similarly, conventional cancer therapies (e.g., chemical chemotherapies, irradiation, immunotherapies, experimental gene therapies) are designed to target highly proliferative cells, thereby sparing a cancer stem line (of the type described by the OSES model) and thus making these types of therapy prone to cancer relapse. OSES-based therapeutic regimens will target the cancer stem line and thus may be less susceptible to relapse and more prone to true cancer cure. Such OSES-based therapies could be used in combination with classical chemotherapies to accelerate diminution of tumor burden while also targeting the clandestine cancer stem line.

Novel Therapies Provided by the Invention

As discussed, it is widely accepted that a cancer cell arises via a multi-step progression from a normal cell to an increasingly "cancer-like" (i.e. pre-cancerous) cell leading ultimately to a full-fledged cancer cell with malignant capability. This process, as is currently described, is driven by neo-Darwinian evolution whereby those increasingly "cancer-like" cells with the most advantageous mutations (e.g., growth-promoting ones) undergo natural selection and expansion over their less "fit" competitors. In this manner, multiple rounds of mutation followed by selection lead ultimately to a malignant cancer cell which is both highly proliferative and highly mutated. It is this generally accepted paradigm for cancer development by which conventional cancer chemotherapies are based. Namely, classic cancer chemotherapies (e.g., alkylating agents such as cyclophosphamide, anti-metabolites such as 5-Fluorouracil, plant alkaloids such as vincristine) as well as irradiation-based therapies have been employed in cancer treatment because of their adverse effects on cellular growth and DNA replication and thus toxicity to highly proliferative (cancer) cells. In a similar manner, certain immunotherapies as well as newer experimental gene therapies have also focused on highly proliferative (and often mutant) cells as the prime targets for cancer treatment. However, while some of these mentioned therapies (i.e. namely the more conventional chemical chemotherapies and irradiation regimens) can induce remission (and occasionally cure) in a subset of cancer types, such therapies do not prolong survival for the majority of patients with cancer. This unfortunate fact is often attributed to technical reasons such as inability to give large enough doses (e.g., due to toxicities), or to the development by cancer cells of resistance to therapy. However, it should be noted that such therapies could also be of limited clinical benefit for other reasons—namely, if the neo-Darwinian paradigm for cancer development (i.e. the basis of conventional as well as newer therapies) were flawed then so too would therapies wholly based on this model.

As an alternative to conventional models, the OSES model, as mentioned, argues that a tumor does indeed largely consist of highly proliferative and mutated cells (in agreement with conventional models) but makes the additional novel proposal that tumors are also (in contradistinction to conventional models) fueled by a clandestine founder sub-population of slow-growing relatively mutationally-spared cells (termed a "cancer stem line") which is not formed by neo-Darwinian cellular evolution but rather by a "quantum leap" of sorts (i.e. a one-step switch in mitotic mode). In this manner, the cancer stem line fuels tumor growth by acting as its immortal founder line which rears a much larger (and thus more readily identifiable) population of highly proliferative mutated progeny cells—i.e., that proliferative mutant population of cells which as mentioned has been the focus of classic chemotherapies, immunotherapies, as well as newer gene therapies. Accordingly, by the OSES model, therapies based on the conventional neo-Darwinian model of cancer (by virtue of their design to target highly proliferative and/or mutant cells) while destroying proliferative mutant cells (i.e. progeny of the cancer stem line which themselves are largely mortal) fail to eradicate the slow-growing relatively mutationally-spared cancer stem line responsible for fueling tumor immortality. Thus, while such conventionally-based treatments may induce clinical remission by transiently reducing overall tumor cell burden, by the OSES model these therapies will ultimately fail to cure cancer in most cases because of a failure of eradicate the cancer stem line which possesses the potential to repopulate the tumor thereby causing relapse (FIGS. 2A and 2B).

In very simple terms, this scenario would be analogous to transiently killing roaches with "Raid" without eradicating their eggs (i.e. stem line) which would need to be targeted by different means (e.g., "Combat") to prevent relapse. That is, conventional therapies use "Raid-like" regimens, while OSES-based therapies would use "Combat-like" regimens. This is not to say that the conventional manner (using classic chemotherapies or newer gene therapies) of destroying the highly proliferative mutated cells (which comprise a large majority of the cells within a given tumor) has no clinical utility—it obviously does by significantly lowering the tumor cell burden which at times can produce clinical remission—but by the OSES model a clandestine cancer stem line still remains untreated (FIGS. 2A and 2B).

Accordingly, it follows from the OSES model that it is the not-yet-appreciated cancer stem line sub-population which is responsible for fueling tumor immortality, a population which escapes classic therapies which themselves are based on a flawed but widely accepted neo-Darwinian paradigm wherein the key cancer cells which should be targeted by therapy are those which are highly proliferative and highly mutated. This flaw extends not only to classic chemical therapies and irradiation modalities but also to other newer and more experimental cancer therapies including tumor-directed monoclonal antibody immunotherapies which have targeted novel antigens present on highly proliferative (often mutant) cancer cells as well as certain newer experimental gene therapies designed (with the conventional paradigm in mind) to correct or override those mutations accrued by cancer cells during their evolution, e.g., by but not exclusive to either 1) destroying mutant cells, as attempted by certain preliminary DNA or RNA (e.g., antisense or ribozyme) therapies "custom-designed" to lethally target certain specific cancer-related mutant genes or their gene products, or 2) "correcting" mutant cells, as demonstrated by recent preliminary gene-directed therapies designed to "override" certain cancer-related mutations via insertion of wild-type versions of these genes into cancer cells (Karp, et al, "New Directions in Molecular Medicine", *Cancer Res.*, 54:653-665 (1994), Kashani-Sabet et al, "Suppression of the Neoplastic Phenotype in Vivo by an Anti-ras Ribozyme", *Cancer Res.*, 54:900-902 (1994)). However, while these conventionally-based methods of cancer treatment may eradicate a significant proportion of the tumor mass by destroying the highly proliferative and mutant neoplastic population thus potentially resulting in clinical remission, in time the tumor may recur at the same or different site(s) for the same reasons that classic chemical chemotherapies often fail. A number of reasons for tumor relapse and chemotherapeutic failure have been offered within the conventional paradigm. These include insufficient chemotherapeutic dosage (limited by onset of significant side effects), and/or emergence of cancer clones (e.g., mutants) which are resistant to therapy. By the OSES model, the emergence of mutant cancer clones (which mayor may not be immortal) may occur in concert with the presence of an underlying cancer stem line, the latter of which has yet to be properly targeted by therapy (FIG. 2A).

The OSES model, as mentioned, offers an alternative explanation for relapse wherein a clandestine slow-growing mutationally-spared cancer stem line, not targeted by conventional therapies, is the immortal founder line of the tumor which may in time gradually regrow the tumor mass. As mentioned, since such a cancer stem line shares growth kinetics with normal stem cells (from which it is directly derived via a one-step epigenetic switch in mitotic mode), i.e. that being a slow-growing immortal cell population which rears progeny cells which themselves are fast-growing and mutant, therapies designed to target fast-growing mutant cells will spare the cancer stem line. Accordingly, novel therapies are needed which specifically target this cancer stem line. This can be accomplished by, but is not exclusive to, newly designed therapies which 1) are specifically cytotoxic to the cancer stem line, e.g., via targeting specific surface antigens, cellular contents, other gene products present in the cancer stem line by immune or other directed cytotoxic therapies "tailor-made" to target the cancer stem line, or 2) force the cancer stem line to switch, permanently or otherwise, from exponential (symmetric) malignant growth to a less "dangerous" arithmetic (asymmetric) growth pattern, or 3) extinguish the cancer stem line by forcing it to permanently adopt a terminal differentiation or apoptotic (i.e. programmed cell death) program. Moreover, it is a goal of such OSES-based cancer therapy to spare normal stem cells of significant therapy-associated toxicity.

Since the malignant stem line is equivalent to symmetrically-dividing stem cells, therapies for eradication of such a cell population will include, but not be exclusive to:

I. immunotherapy directed at normal adult stem cells antigens since such antigens will largely be present on a cancer stem line derived from stem cells of a given tissue type having been inherited en bloc via a one-step epigenetic switch) (FIG. 3A); and/or II. induction of a switch from symmetric to asymmetric mitosis in the cancer stem line by activating or suppressing positively or negatively-acting factors, respectively, which are normally involved in controlling this switch in normal stem cells thereby effecting a change from exponential to arithmetic tumor growth (FIG. 3B); and/or III. induction in the stem line of terminal differentiation or apoptosis (i.e. programmed cell death) by causing a switch from a symmetric proliferative mitotic program which normally responds to differentiation-inducing signals or starvation by assuming an metric quiescent growth phase (thereby retaining a proliferative capability for later use) to one that switches to a symmetric but terminal differentiation or apoptotic program whereby a proliferative capability is irreversibly lost (FIG. 3C). By this method, mitotic mode is uncoupled from differentiation—a process which occurs to various degrees in lower eukaryotes.

These are three examples of how the cancer stem line could be targeted and contained for the treatment of cancer. Therapies to treat cancer based on the OSES model include such methods but are not exclusive to them and may involve additional modalities as newer technologies are developed and additional information on the molecular mechanisms of how a stem line (normal or neoplastic) (behaves) becomes available which will provide new heretofore unknown cancer stem line targets. The mentioned therapies are described in greater detail below, but are not intended to be exhaustive.

I. Targeting a Cancer Stem Line Via Novel Immunotherapy

Cancer immunotherapy in the past has been designed to target antigens which are mutated and/or present on highly proliferative cancer cells, which by the OSES model would constitute antigens present on cancer stem line progeny rather than the cancer stem line itself. Accordingly, by the OSES model, classic immunotherapy (like classic chemotherapies and irradiation treatments) is similarly flawed because while it may destroy the bulk of cancer stem line progeny, it will not target the underlying cancer stem line which fuels tumor immortality.

As mentioned, according to the OSES model, cancer cells are symmetrically-dividing stem cells. Therefore, certain antigens present on normal stem cells will also be present on cancer cells for "neutral" reasons (i.e. because of en bloc inheritance) rather than for reasons of "selection". In addition, antigens shared by both cancer cells and stem cells should also to some extent be preset on embryonic progenitor cells from which adult stem cells are derived (due also to inheritance). Accordingly, as embryonic progenitor cells, stem cells, and cancer cells from the same tissue of origin will share certain surface antigens (which may subsequently be lost during cell differentiation and thus not readily detectable in adult tissues), identification of such shared antigens for use as potential targets for immunotherapy for cancer (i.e., to target the cancer stem line) should be sought. This can be assisted via study of embryonic or adult stem cells, for the purpose of identifying cell surface antigens present on these non-cancerous cell types, which may be technically easier to isolate and characterize than those on cancer stem line cells themselves. A proportion of such antigens would then, according to the OSES model, be presumed to be present on a cancer stem line derived from that particular tissue and thus worthy of therapeutic targeting. This method contrasts with classic immunotherapies which have not targeted native stem cell antigens but rather antigens present on highly proliferative (often mutant) cancer cells, which by the OSES model is a cell population that does not represent the immortal population which needs to be most aggressively targeted. In support of the above OSES-derived proposal that certain wild-type cell products (e.g., cell surface antigens) may be shared by embryonic cells and adult stem cells along with cancer cells from that particular tissue type, there is evidence that some tumor cell types (both of hematopoietic as well as solid origin) share expression of isoforms of certain fetal stage-specific genes including in some cases embryonic cell-surface antigens with their normal stem cell counterparts (Sachs, "Cell Differentiation and Bypassing of Genetic Defects in the Suppression of Malignancy", Cancer Res., 47:1981-1986 (1987); Hall, "Stem Cell Is a Stem Cell Is a Stem Cell", Cell, 33:11-12, (1983); Sigal et al, "The liver as a stem cell and lineage system", Am. J. Physiol., 263:G139-G148 (1992)). For example, certain cell surface antigens (e.g., SSEA antigen family) detected on murine germ cell-derived tumors have also been detected on adult oocytes (i.e. germline stem cells) as well as on 4-8 cell mouse embryos (Hall, "Stem Cell Is a Stem Cell Is a Stem Cell", Cell, 33:11-12, (1983)). Moreover, expression of several cell surface antigens as well as other primitive gene products including alpha-fetoprotein (AFP) and IGF-2 have been detected in hepatic tumor cells, adult stem cells of the liver, as well as in fetal liver indicating shared gene expression by these temporally-distinct but related cancerous and non-cancerous cell types (Sigal et al, "The liver as a stem cell and lineage system", Am. J. Physiol., 263:G139-G148 (1992)). While conventional models might attribute such findings to dedifferentiation of an adult cell to a more primitive form, the OSES model as mentioned argues that such similarities in gene expression between cancer cells, adult stem cells, and embryonic cells is due to inheritance and not to dedifferentiation or selection. In this manner, the OSES model seems more parsimonious than conventional ones in that it need not be forced to invoke selection (as conventional models are) to explain the presence of surface antigens which appear for all intents and purposes to be "neutral" (i.e. without any selective benefit) a concept which has posed somewhat of a problem for conventional models.

It follows from this idea that if a cancer stem line shares expression of certain gene products (e.g., certain cell-surface antigens) with adult stem cells and embryonic cells of its tissue type of origin then immune-directed targeting of certain native antigens present on embryonic progenitors and stem cells from the same tissue lineage should, by the OSES model, target the cancer stem line. By contrast, cancer immunotherapies in the past have been directed toward antigens present on the highly proliferative (and often mutant) population of cancer cells and thus, in a similar manner to conventional chemical chemotherapies, will not eradicate the immortal cancer stem line whose surface antigens are likely non-mutant and distinct from those expressed by their proliferating and/or differentiating progeny.

By the OSES model, suitable cancer stem line antigens to be targeted by monoclonal antibodies may be identified by, e.g., cloning adult stem cells of various tissue types in order to determine their expression profiles and complement of cell surface antigens for a particular tissue and assuming that a proportion of these cell products will also be present in a cancer stem line derived from these stem cells (because of en bloc inheritance). Cloning of adult stem cells of hematopoietic origin is a technique previously described and now done routinely by those skilled in the art (Uchida et al, "Heterogeneity of hematopoietic stem cells", Curr. Opin. Immunol., 5:177-184 (1993)). There has now also been some preliminary success in isolating stem cells of non-hematopoietic tissues, namely gastrointestinal epithelia (Gordon et al, "Differentiation and self-renewal in the mouse gastrointestinal epithelium", Curr. Opin. Cell Bio., 6:795-803 (1994)). Improved purification methods to isolate (non-hematopoietic) stem cells from their non-stem cell neighbors will, possibly aided by separation techniques that focus on gene products differentially expressed in stem and non-stem cells as targets for separation (e.g., data gleaned from both normal and virally-infected lineage studies), will undoubtedly help in the identification of stem cell-specific gene products (e.g., integrins, as seen in epidermal stem cell systems) (Jones et al, "Stem cell patterning and fate in human epidermis", Cell, 80:83-93 (1995)), which will also include products which are cell antigens (Sigal et al, "The liver as a stem cell and lineage system", Am. J. Physiol., 263:G139-G148 (1992); Villarreal, Relationship of Eukaryotic DNA Replication to Committed Gene Expression: General Theory for Gene Control, Micrbiol. Rev., 512-542 (1991)). In other words, as more stem cell-related data become reported so too will the number of possible antigens for which to target a cancer stem line derived from a given tissue type by these novel methods.

Monoclonal antibody construction specific to hematopoietic stem cells is a technique which has been previously well-described (Uchida et al, "Heterogeneity of hematopoietic stem cells", Curr. Opin. Immunol., 5:177-184 (1993)). Although a technique not yet as perfected, cloning of non-hematopoietic stem cells and construction of monoclonal antibodies specific to them has also had some preliminary success (Hall, "Stem Cell Is a Stem Cell Is a Stem Cell", Cell, 33:11-12, (1983)). Accordingly, by the OSES model, perfection of this technique can then be used to target (via immunotherapy) a cancer stem line arising from that particular stem cell type. Construction of cell type-specific monoclonal antibodies involve methods well-known to those skilled in the art. In this manner, antibodies designed to be non-tolerant of antigens native to adult stem cells (and/or their precursor embryonic cells) will selectively home in on stem cells which are no longer environmentally sequestered (i.e., a cancer stem line). It should be noted that several monoclonal antibodies have already been constructed against non-hematologic tissues including murine embryonic cells (Hall, "Stem Cell is a Stem Cell Is a Stem Cell", Cell, 33:11-12, (1983)). Their efficacy as potential therapeutic agents for cancer (a novel idea which follows from the OSES model) awaits demonstration. Evidence that certain antigens may be shared by related but independent developing tissue types may also enable certain monoclonal antibodies made to one embryonic/stem cell type to be used to treat more than one cancer cell type thereby expediting assessment of the efficacy of this novel OSES-derived method for treating cancer (Hall, "Stem Cell Is a Stem Cell Is a Stem Cell", Cell, 33:11-12, (1983)). Thus, the OSES method of immune-directed targeting of neoplastic cells differs from previous cancer immunotherapies the latter of which have targeted mutant tumor antigens or antigens present on proliferating or differentiating stem line progeny rather than (as recommended by the OSES model) on wild type antigens normally expressed by embryonic progenitor and adult stem cells, i.e. antigens presumed to also be present on a cancer stem line.

It should also be noted that some previously described cancer immunotherapeutic regimens have attempted to augment an endogenous immune response to cancer. However, by the OSES model, this method is similarly flawed because antigens native to embryonic and adult stem cells may not normally be viewed as foreign by the immune system (since immune progenitor cells are likely exposed to such native embryonic antigens prior to adoption of immunologic tolerance) and thus the immune system might be tolerant to antigens expressed on a cancer stem line and therefore not attack it. This idea is unique to the OSES model. In this manner, simply augmenting the native immune response to a tumor by any of a variety of previously described means would not be expected to result in eradication of a non-foreign-appearing cancer stem line. On the other hand, promotion of cytotoxicity to this otherwise "normal-appearing" but pathogenic cancer stem line (such as by engineering monoclonal antibodies targeting it, as described above) would, by the OSES model, result in its demise. In addition, ex vivo induction of embryonic/stem cell antigen non-tolerance in progenitor (i.e., "impressionable") immune cells followed by their reintroduction into a patient with cancer of that particular cell type would be another way by the OSES model to effect cancer stem line immune-directed cytotoxicity. Ex vivo therapies used for other reasons have been described and are well-known by those skilled in the art.

Once monoclonal antibodies to stem cells are obtained, they may be used to produce immunotherapies by conventional methods. For example, the monoclonal antibody may be attached directly or indirectly to a therapeutic moiety, e.g., a therapeutic enzyme, chemotherapeutic agent, cytotoxin, lymphokine, cytokine, radionuclide, anti-metabolite, or derivatives thereof, or may be used alone to stimulate native immune system attack. Alternatively, the antibody may be used in pre-targeting therapies which in turn administer an antibody-(ligand or anti-ligand) conjugate which binds to targeted cells, followed by administration of a (ligand or anti-ligand) therapeutic moiety conjugate. Such methods are often favored over administration of antibody-therapeutic agent conjugates as they may reduce non-specific cytotoxicity. Also, it is desirable that the antibody be substantially non-immunogenic in the treated subject. This may be accomplished by chimerizing or humanizing the monoclonal antibody, or producing a single chain version thereof. In addition, antibody fragments, such as Fab fragments are less immunogenic because of their smaller size.

Methods for administering antibodies are well known in the art and include parenteral modes of administration such as intraperitoneal, intramuscular and intravenous injection, as well as systemic routes of administration, e.g., oral, intranasal, etc. Generally, an antibody or antibody conjugate will be administered in combination with a pharmaceutical carrier or excipient, and in conjunction with moieties that preserve the stability thereof, e.g., buffers, and compounds which maintain protein stability. The dosage amount will vary within wide limits. Generally, it will vary from about 0.001 mg to 10 m/Kg body weight.

However, a possible side effect of OSES-based treatment of a cancer stem line is potential toxicity to normal stem cells. This will depend largely on whether normal stem cells, by virtue of their environmental sequestration, are spared of stem/cancer cell immune-directed attack. In other words, it is possible that stem cells within the micro-environments of solid tissues are not accessible to immune-directed attack thereby reducing the side effects of such novel therapy. If normal stem cells are susceptible to monoclonal antibody targeting, then an alternative approach whereby such monoclonal antibodies aye used solely for detection of a cancer stem line rather than eradication thereof (e.g., via tagging to a benign identifiable marker such as fluorescence, as will be discussed later in the detection section) such that detection and localization could lead to early local conventional modes of therapy (e.g., irradiation or surgical removal) of what would have been undetectable cancer cells. This method would be without adverse effects to normal stem cells (other than temporary benign fluorescence). Moreover, successful removal of a cancer stem line might allow further characterization of its expression profile and cell surface antigens so as to determine distinguishing features from its normal stem cell counterparts to which to design more specific immunotherapy so as to avoid targeting normal stem cells if more specific therapeutic targeting is warranted.

EXAMPLE 1

A patient is found to have breast cancer by conventional detection techniques (e.g., mammogram and biopsy). Monoclonal antibodies designed to bind specific antigens present on the surfaces of normal mammary gland epithelial stem cells, also possessing an attached therapeutic moiety (e.g., cytotoxin), are delivered intravenously to the patient. This therapeutic monoclonal antibody will seek out and destroy a cancer stem line fueling the breast tumor while largely sparing environmentally-sequestered normal mammary epithelial stem cells (see FIG. 3A). Efforts to limit this toxicity further are discussed in the final section, (III.).

II. Forcing a Cancer Stem Line to Undergo Asymmetric Mitosis

An alternative tactic to immunotherapy for containing a cancer stem line is to design therapies which (rather than killing stem cells) bring about the conditions of a normally sequestered stem cell micro-environment to wayward stem cells (i.e. cancer cells) which in turn should force them to resume asymmetric mitosis and arithmetic growth kinetics. Since stem cells are not targeted for death by this form of therapy, there should be minimal toxicity to normal stem cells which presumably are already dividing asymmetrically anyway.

As mentioned, by the OSES model cancer cells are symmetrically-dividing stem cells which, while capable of transiently switching to asymmetric mitosis when induced to do so by local differentiation-inducing signals, will assume an exponential (symmetric) growth pattern when extrinsic differentiation-inducing stimuli are lacking (e.g., at more centrally-located rather than peripheral tumor regions where cancer cells are "shielded" of such signals) thereby forming a centrally-located symmetrically-dividing cancer stem line. Accordingly, efforts to contain such a "shielded" cancer stem line via targeted delivery of therapeutic effectors of asymmetric cancer cell mitosis will limit stem line size and thus potential numbers of reared progeny. Such a novel treatment modality for cancer may derive from either: 1) use of known differentiation-inducing agents (but to be used in a novel dosing manner), and/or 2) design of new differentiation-inducing agents (based on knowledge of native asymmetric mitosis/differentiation machinery). By this latter OSES-derived mode of therapy, native local differentiation-inducing factors (i.e. those normally present in a stem cell milieu) together with their downstream effectors of asymmetric stem cell mitosis will act as effectors and targets, respectively, for therapeutic interventional manipulation designed to force a cancer cell to switch from symmetric to asymmetric mitosis.

1) Induction of Asymmetric Cancer Stem Line Mitosis Via Delivery of Known Differentiation-Inducing Agents Coercion of a cancer stem line to divide via asymmetric mitosis can be effected by various means such as, but not exclusive to, e.g., delivery of a ligand which upon receptor binding leads to induction of a pathway leading to differentiation of the cancer stem line (i.e. asymmetric cancer stem line mitosis). This type of treatment modality would be transient, however, the duration of which would correlate with the half-life of the downstream effects of the delivered ligand. It should be noted that certain differentiation-inducing drugs (e.g., all-trans retinoic acid, ATRA) have indeed previously been shown to have clinical benefit in cancer therapy, and ATRA is now part of the accepted treatment regimen for acute promyelocytic leukemia (Degos, et al "All-Trans-Retinoic Acid as a Differentiation Agent in the Treatment of Acute Promyelocytic Leukemia", Blood, 85:2643-2653 (1995)). Other differentiation-inducing compounds such as Hexmethylene bisacetamide, 5-Azacytidine, and 1-beta-D-Arabinofuranosylcytosine have also been cited as potential cancer therapies, but their clinical utility awaits further demonstration (Pierce et al, "Tumors as Caricatures of the Process of Tissue Renewal: Prospects for Therapy by Directing Differentiation", Cancer Res., 48:1996-2004 (1988)). It has been somewhat enigmatic, by conventional thinking, how cancer cells (presumably having been created via a stepwise evolutionary process involving mutation-selection) could reverse such a permanent process (i.e. bypass cumulative genetic derangements) and revert to normal via differentiation. By the OSES model, however, cancer cell reversion via differentiation is much more readily explained. Namely, the mechanism by which differentiation-inducing agents act is via induction of a mitotic switch in the cancer stem line to asymmetric cancer cell mitosis (i.e. which, would appear grossly as tumor differentiation). However, this type of therapeutic mode, according to the OSES model, would be transient since after removal of a differentiation-inducing drug the stem line would resume symmetric mitosis thereby making a treated patient prone to relapse (i.e., re-institution of symmetric cancer cell mitosis) upon discontinuance of the drug. Accordingly, it would follow from the OSES model that more prolonged therapy with differentiation-inducing agents such as ATRA (but at lower doses to reduce side effects) would be a novel and more efficacious treatment program than is currently used because it would provide a continual stimulus for a cancer stem line to divide asymmetrically rather than symmetrically. Current dosages of ATRA range from 15-45 mg/m2/d for a recommended treatment duration of 30-45 days (Degos, et al "All-Trans-Retinoic Acid as a Differentiation Agent in the Treatment of Acute Promyelocytic Leukemia", Blood, 85:2643-2653 (1995)). White continuous therapy has not been shown to be efficacious at these dosages, it would follow from the OSES model that lower dosages (e.g., 2-10 mg/m2/d) to avoid toxicities for a prolonged period (e.g., 6 months or longer) should be efficacious. In addition, other differentiation agents (e.g., Hexmethylene bisacemtamide, 5-Azacytidine, and 1-beta-D-Arabinofuranosylcytosine) may also provide clinical benefit as a cancer treatment at their respective adjusted low dose and prolonged duration of therapy than is currently suggested.

As directed by the OSES model, in addition to utilizing pre-existing drugs capable of inducing cell differentiation for the treatment of cancer (some of which are mentioned above), newer more specific differentiation-inducing agents may also be employed. Namely, elucidation of the molecular mechanisms which lead to normal asymmetric stem cell mitosis will allow use of such native factors (as well as permit their use as templates for the design of "tailor-made" factors) to be exploited as therapeutic effectors of asymmetric cancer stem line mitosis for the treatment of cancer.

2) Induction of Asymmetric Cancer Stem Line Mitosis Via Delivery of New Differentiation-Inducing Agents (the Design of which is Based on Knowledge of the Native Asymmetric Mitosis Pathway)

In order to design specific differentiation-inducing cancer therapy that will force a cancer stem line to undergo asymmetric mitosis, one must look more closely at the molecular mechanisms which bring about asymmetric mitosis in normal stem cells in order to decide where and how to intervene in order to constitutively activate such a pathway in a cancer stem line. For example, by identifying genes and gene products required for normal asymmetric mitosis, therapeutic interventions can be specifically designed with high precision (e.g., via activating those identified native factors that drive asymmetric mitosis or, alternatively, blocking native factors that inhibit asymmetric mitosis) to switch a cancer stem line from a symmetric to an asymmetric mitotic program thereby altering the growth kinetics of the treated tumor. Toxicity to normal stem cells associated with this type of therapy may or may not be very significant since normal stem cells are presumably dividing asymmetrically anyway. Of course, efforts to better direct this type of therapy specifically to a cancer stem line while sparing normal stem cells (as will be discussed) would always be preferred.

The molecular machinery of asymmetric mitosis: Asymmetric mitosis is a widespread process in the animal kingdom that is functionally well-conserved in organisms ranging from yeast to nematode to insect to man. Mechanistically, it is becoming increasingly evident that cells utilize some aspect of their pre-existing structural asymmetry to initiate a mitotic cell division which is also asymmetric in nature (i.e. manifested by unequal segregation of certain intracellular factors to resulting daughter cells such that these progeny cells assume different fates, e.g., as in mammalian stem cells, one daughter cell renews pluripotency while the other terminally differentiates). Structural asymmetry can be due to a variety of factors such as an internal marker (e.g., a bud scar in yeast which marks the site of the previous cell division, or the site of sperm entry in a nematode zygote both of which may provide the cell with a nidus of asymmetry), or an external marker (e.g., the apical/basal polarity of an epithelial stem cell as determined by its environment, or the particular membrane receptor site from which the highest concentration of extrinsic signals are transduced) (Way et al, "Cell polarity and the mechanism of asymmetric cell division", Bioessays, 16:925-931 (1994); Lin et al, "Neuroblasts: a model for the asymmetric division of stem cells", Trends Genet., 13:33-39 (1997)).

By the OSES mode, the asymmetric mitotic pathway in stem cells is initiated by ligand-receptor binding whereby one or more native locally-acting differentiation factors within a stem cell milieu (e.g., but not exclusive to, gene products of Wnt, Hedgehog, Transforming growth factor, Epidermal growth factor) bind to their respective receptors (present on stem cells) and induce stem cells to enact an asymmetric mitotic program. Preliminary data from a number of different organism suggest that, following ligand-receptor binding, asymmetric stem cell mitosis proceeds via the following general pathway: a) (intrinsic or extrinsic) structural asymmetry in a stem cell is "recognized" (e.g., via inhibition of factors that block its recognition) thereby leading to asymmetric assembly of factors which unequally mobilize b) transcription factors to unequally activate c) genes responsible for determining cell fate whose products become unequally apportioned thereby leading to two qualitatively distinct daughter cells. A number of specific gene products involved at various points of this pathway have been isolated from a variety of organisms Table 1 is a preliminary list of such factors, but is not intended to be exhaustive (Way et al, "Cell polarity and the mechanism of asymmetric cell division", *Bioessays,* 16:925-931 (1994)).

It should also be noted that there may be other processes and factors (i.e. not mentioned in Table 1) that act at key points within this pathway to bring about an asymmetric mitotic cell division in normal stem cells. For example, within this preliminary general pathway for asymmetric mitosis (Table 1) there are likely to be points of convergence of signals (i.e., "bottlenecks") wherein cellular decisions are made from a consensus of signals (FIG. 4). Interestingly, there are some preliminary data that such "bottlenecks" in the mitotic pathway may, in part, consist of key cellular events that lead to somatic chromosomal pairing and subsequent exchange events which are inherently unequal and thus propagate the initial asymmetry of this entire pathway leading ultimately to an asymmetric mitotic cell division. This is discussed further below.

"Bottlenecks" in the Asymmetric Mitotic Pathway: Allelic Pairing/Exchange

As shown in (FIG. 4), the asymmetric mitotic pathway in normal stem cells may contain one or more points of convergence of signals (i.e. "bottlenecks"). It is proposed here that one cellular process which may represent such a "bottleneck" in the asymmetric mitotic pathway is that of homologous chromosomal pairing and exchange. By this model, following chromosomal replication in a stem cell, paring/exchange between one set of homologous chromosomes will mark that daughter cell (receiving the exchanged homologs) for subsequent events leading to the unequal segregation of factors preferentially to the marked (or unmarked) daughter cell thereby resulting in a difference in fate between daughter cells (i.e. asymmetric mitosis). Such a process is hypothesized to be a "bottleneck" in the pathway because it is presumed to rely on a consensus of multiple coining ligand-receptor signal transduction effects such that if a threshold of such signals is met then pairing/exchange and asymmetric mitosis will proceed, if not then pairing/exchange will not occur and there will be equal segregation of factors to daughter cells (i.e. symmetric mitosis). What evidence supports these claims?

It is well known in haploid yeast that allelic pairing/exchange leads to expression of certain cell fate-determining factors that become unequally segregated to resulting daughter cells (i.e. asymmetric mitosis) (Horvitz and Herskowitz, "Mechanisms of Asymmetric Cell Division: Two Bs or Not Two Bs, That is the Question", *Cell,* 68:237-255 (1992)). In this case, allelic exchange consists of a gene conversion event at the mating type locus (MAT) which in turn directly leads to up-regulation of a (previously silent) exchanged MAT allele whose downstream products are asymmetrically apportioned to resulting daughter cells. There is also evidence that a related process (termed "trans-sensing") occurs in higher diploid eukaryotes. Namely, it has been shown in *Drosophila* that pairing of homologous alleles in somatic cells can control expression of those paired gene complexes, (Tartof and Henikoff, "Trans-Sensing Effects from *Drosophila* to Humans", *Cell,* 65:201-203 (1991)). In an analogous manner to the yeast system where allelic pairing affects expression (of one of the paired MAT alleles) via an exchange event at the DNA level, it appears that in higher eukaryotes (e.g., *Drosophila*) allelic pairing also affects expression (of one of the paired alleles) but via an exchange event at the epigenetic rather than genetic level (e.g., which may involve nucleosomes, chromatin, and/or transcription factors). This process appears to also, in a similar manner to DNA exchange events in yeast, require intimate chromosome pairing as well as other downstream recombination-like process (e.g., heteroduplex formation) suggesting that the processes of genetic and epigenetic exchange may be mechanistically related. A number of genes have been isolated which are involved in the trans-sensing process in *Drosophila*. Some of these genes include zeste which alters expression of downstream genes such as the polycomb genes. Other genes involved in this process include white, decapentplegic, and notch (Wu et at, "The *Drosophila* zeste gene and transvection" *Trends Genet.,* 5:189-194 (1989)). While this system awaits further description, there is preliminary evidence that this trans-sensing pathway (involving zeste-polycomb), like gene conversion in yeast, is also involved in expression of cell fate determinants that are segregated to daughter cells (Pirrotta, "Transfection and Long-Distance Gene Regulation", *Bioessays,* 12: 409-414 (1990)). What about human cells?

There is evidence from a number of sources that homologous chromosomal pairing/exchange occurs in mammalian cells and that alteration of this process leads to certain developmental abnormalities (thereby indicating a role for this process in normal development). It is proposed here that the mechanism by which pairing/exchange functions in mammalian development is similar to that in yeast and possibly *Drosophila*, i.e. via affecting expression of one of the paired alleles which in turn leads to expression of downstream cell fate-determinants that are unequally apportioned to resulting daughter cells (i.e. asymmetric mitosis).

Evidence for somatic homologous pairing (and possible exchange of information) in mammalian cells is derived from a variety of sources. For example, there is evidence by interphase cytogenetics that chromosome pairing normally occurs in mammalian neural cells (Wu, "Transvection, nuclear structure, and chromatin proteins", *J. Cell. Biol.* 120:587-590 (1993)). Interestingly, some of these paired regions correspond to regions of homologous recombination in cells from patients with Bloom's Syndrome. These findings support a role for the wildtype human Blooms' syndrome helicase-like gene (BS) in inhibiting DNA exchanges during the presumably normal act of allelic pairing (Tartof and Henikoff "Trans-sensing effects from *Drosophila* to Humans", *Cell,* 65:201-203 (1991), Ellis et al, "The Bloom's Syndrome Gene Product Is Homologous to RecQ Helicases", *Cell,* 83: 655-666 (1995)).

There are also data that homologous allelic pairing/exchange (i.e. trans-sensing) occurs at additional human loci. For example, confocal laser scanning microscopy and 3-dimensional fluorescence in situ hybridization (3D FISH) have revealed that certain homologous loci (in the chromosome 15q11-13 region) clearly associate with one another in somatic cells (LaSalle et al, "Homologous Association of Oppositely imprinted Chromosomal Domains", *Science,* 272: 725-7281 (1996)). That such close associations at 15q11-13 are followed by exchange of developmentally-significant information is suggested by several lines of evidence:

1) This association occurs in well-defined spatial and temporal patterns.

2) This region is imprinted (i.e. homologous alleles harbor different epigenetic structure) thereby making an exchange of epigenetic information potentially "meaningfull" (i.e. in contrast to an exchange of identical epigenetic information which would be "meaningless").

3) Developmental abnormalities arise when pairing in this region is defective, as seen in Angelman and Prader-Willi syndromes (LaSalle et al, "Homologous Association of Oppositely Imprinted Chromosomal Domains", *Science,* 272: 725-728 (1996)). Namely, in both of these conditions, imprints between homologous alleles at 15q11-13 are identical which presumably disallows pairing/exchange which in turn leads to aberrant human development.

4) Exchange of epigenetic structure has indeed been shown to follow pairing of alleles at 15q11-13, but during meiosis, which suggests that it might also occur following pairing in other instances, e.g., mitosis (Kelsey and Reik, "Imprint switch mechanism indicated by mutations in PraderWilli and Angelman syndromes", *Bioessays,* 19:361-365 (1997)).

There is also evidence for allelic pairing/exchange (i.e. trans-sensing) in the region of human chromosome 11p15, and that such a process directs proper development. Namely, this region like 15q11-13 is also imprinted (thereby making epigenetic exchange potentially "meaningful"). In addition, developmental abnormalities also arise when imprinting (and presumably pairing) is defective in the 11p15 region (i.e. homologous alleles have identical epigenetic structure), as seen in cases of Beckwith-Wiedemann syndrome (BWS) (Fidler et al, "Trans-sensing hypothesis for the origin of Beckwith-Wiedemann syndrome", *Lancet,* 339:243 (1992)). Moreover, that exchange of epigenetic structure can indeed occur between homologous alleles in this region is evidenced by documentation that a (paternally-derived) imprint was transferred from one allele of H19 (a gene located in 11p15) to the other (presumably preceded by allelic pairing) in certain Wilms' tumors (Colot et al, "Interchromosomal transfer of epigenetic states in Ascobolus: Transfer of DNA methylation is mechanistically related to homologous recombination", *Cell,* 86:855-864 (1996)). These mentioned findings indicate that trans-sensing of certain alleles in 11p15 is a necessary condition for normal development, while inhibition of trans-sensing of other alleles in this region may be needed to prevent abnormal cellular growth.

In a related manner, it has previously been proposed that inhibition of native trans-sensing in the regions of human chromosome 3q21, 3q26, 16p13, and 16q22 may similarly predispose to abnormal cellular growth (i.e. certain hematologic malignancies, in these cases) (Tartof and Henikoff, "Trams-Sensing Effects from *Drosophila* to Humans", *Cell,* 65: 201-203 (1991)).

Trans-sensing has also been implicated in the pathogenesis of Huntington's disease (HD). Namely, in order to account for the variability of expression of this dominant phenotype, it has been suggested that trans-sensing may act between homologous HD alleles (on the short arm of human chromosome 4) in somatic cells (Laird, "Proposed genetic basis of Huntington's disease", *Trends Genet.,* 6:242-247 (1990)). The mechanism by which trans-sensing acts in this region is likely similar to that documented for the 11p15 region in somatic cells and the 15q11-13 in germ cells (and hypothesized for the HD region in germ cells) where epigenetic structure is exchanged via transfer from one homologous allele to the other (Colot et al "Interchromosomal transfer of epigenetic states in Ascobolus: Transfer of DNA methylation is mechanistically related to homologous recombination", *Cell,* 86:855-864 (1996); Kelsey and Reik, "Imprint switch mechanism indicated by mutations in Prader-Willi and Angelman syndromes", Bioessays, 19:361-365 (1997); Sabl and Laird, "Epigene conversion: A proposal with implications for gene mapping in humans", *Am. J. Hum. Genet.,* 50:1171-1177 (1992)). Accordingly, it is proposed here that exchange of epigenetic structure from one paired homologous allele to other results in a change in expression of the epigenetically altered allele due to a switch from either a euchromatin-like to a heterochromatin-like structure, or vice versa, thereby leading to down or up-regulation, respectively of the affected allele. In this manner, such an expression change would lead to induction of downstream cell fate determinants which would be unequally segregated to daughter cells. Such a proposal would be analogous to the yeast system where change in expression of an exchanged allele (of MAT) leads to induction of downs cell fate determinants that are asymmetrically apportioned to daughter cells. Only in the yeast case, an allele is transferred to an expressible chromosomal site (so that it can be expressed) whereas in the proposed human case, the reverse occurs but with the same outcome, i.e. an expressible chromosomal configuration is transferred to the allele (so that it can be expressed).

By this hypothesized model, therapy devised to activate this pathway (e.g., at the level of allelic pairing/exchange) would force a (symmetrically-dividing) cancer stem line cell to undergo asymmetric mitosis. In the opposite manner, interruption of allelic pairing/exchange in a cancer stem line would freeze a cancer stem line in a symmetric mitotic mode—a result which could, paradoxically, also be beneficial for cancer treatment, as will be discussed in subsection 3).

The following are examples of functions and gene products that may act as "bottlenecks" in the asymmetric mitotic pathway involving allelic pairing/exchange:

a) chromosomal pairing/unpairing—Helicases: Bloom's syndrome (BS), Werner's syndrome (WS), xeroderma pigmentosa, Cockayne's syndrome, trichothiodystrophy), ATM, topoisomerase-2.
Meiotic pairing genes: multiple yeast genes, as well as human, e.g., mos, MLH-1, PMS-2, BRCA-1, SIR4 (yeast), RAD50(yeast)

b) epigenetic pairing/exchange—zeste (*Drosophila*), and other trans-sensing factors.
15q11-13 imprinted genes: ZNF127, IPW, PAR5, PAR1, SNRPN, E6AP ubiquitin-protein ligase (UBE3A).
11p15 imprinted genes: IGF-2, IGF-2r, H19, p57KIP2 c) downstream of chromosomal pairing—polycombgenes (*Drosophila*), transcription factors (e.g., WT-1), APC d) modifiers of epigenetic exchange—
X-linked modifier of HD trans-sensing:
M31/HSM1, M32 e) effectors of epigenetic exchange—
alternate splicing (by RNA-binding proteins) of a host of factors in *Drosophila*, e.g.: Sx1, dsx f) resolution of recombination intermediates (e.g., heteroduplexes, triplexes)—multiple yeast recombination and repair proteins, endonucleases g) abortion of recombination—mismatch repair, methylation maintenance proteins, methylation or nick stand recognition factors (Dittrich et al, "Imprint switching on human chromosome 15 may involve alternate transcripts of the SNRPN gene", *Nature Genet.,* 14:163-170 (1996); Singh et al, "A sequence motif found in a *Drosophila* heterochromatin protein is conserved in animals and plants", *Nucleic Acids Res.,* 19:789-794 (1991); Laird, "Proposed genetic basis of Huntington's disease", *Tends Genet.,* 6:242-247 (1990); MacDougall et al, "The developmental consequences of alternate splicing in sex determination and differentiation in *Drosophila*", *Dev. Biol.,* 172:353-376 (1995)).

Accordingly, such processes (and those factors involved) may be added to the list of effectors of the machinery of asymmetric stem cell mitosis identified in Table 1. As will be discussed in this section, it follows that therapeutic activation, in a (symmetrically-dividing) cancer stem line, of native factors that drive asymmetric mitosis of normal stem cells (e.g., but not exclusive to, those mentioned in Table 1 and supra) should induce a cancer stem line to switch to asymmetric mitotic division.

As described, by the OSES model symmetric stem cell mitosis (i.e. cancer) initiates when local differentiation-inducing signals within a stem cell milieu are disturbed (e.g., due to carcinogen-induced disruption of those non-stem cells within a stem cell milieu that normally produce such differentiation-inducing factors). Accordingly, when such signals are disturbed: 1) differentiation-related genes are not turned on in stem cells, and 2) underlying structural asymmetry of a stem cell becomes "ignored" (i.e., native inhibition of asymmetric mitosis-inducing factors is maintained rather than inhibited) thereby preventing asymmetric segregation of cell fate-determining factors to resulting daughter cells. Accordingly, such a stem cell (i.e., within a disturbed milieu) would undergo mitosis without induction of differentiation related genes or its asymmetric machinery, which by definition is a symmetric mitotic division of stem cell fate-determinants (i.e., the initiation of cancer). By this model, novel OSES-derived therapies designed to activate (i.e., cause to "recognize") asymmetric mitosis-inducing factors within a cancer stem line should lead to coercion of a cancer stem line to divide via asymmetric mitosis thereby leading to its containment. Evidence that cancer cells can indeed maintain an ability to differentiate (i.e., undergo asymmetric mitosis) has been presented in the Background section, and evidence that cancer cells at the tumor periphery are more differentiated than at central regions is consistent with the OSES-derived idea that cancer cell differentiation results (not from intrinsic causes but rather) from local differentiation-inducing signals, as described. This OSES scenario, as described, depicts a tumor with a propensity for its most "shielded" cells (i.e. centrally-located ones) to be least differentiated (i.e. the cancer stem line).

It should emphasized that it is the OSES model (more so than conventional ones which themselves view the relation of cancer to tissue development simply as a stochastic result of dedifferentiation), which seeks to exploit the rapidly advancing fund of knowledge concerning gene products involved in normal tissue development (e.g., but not exclusive to those mentioned in Table 1) for potential therapeutic benefit. Conventional models, in contradistinction, have viewed cancer cells largely as "alien-like" (e.g., proliferative invasive mutants) and thus have not been as concerned (as the OSES model is) with the parallels between cancer and normal tissue development.

As will be discussed, design of novel OSES-derived therapies will be based on knowledge of those native factors which normally act in the asymmetric mitotic pathway in stem cells (Table 1) for a preliminary list) so that such factors can be activated/inhibited, as the case may be, for the purpose of coercing a cancer stem line to undergo asymmetric mitosis. The pace of current advances in developmental biology is such that this list (Table 1) continues to grow and the underlying hierarchy of action regularly updated. Elucidation of the evolutionarily conserved pathway of tissue development (i.e., asymmetric mitosis) in non-human organisms will undoubtedly assist in understanding normal human tissue development (and human cancers). Moreover, following identification of non-human development-related genes, more human homologs of these genes can then be isolated by methods used by those skilled in the well-described art of gene cloning, e.g., via low stringency hybridization in Southern blotting and/or (preceded by) use of degenerate primers to conserved regions of such sequences in Polymerase Chain Reactions (for the purpose of cloning preliminary gene fragments)—the actual human genes or sequences of which can then be used as effectors or templates, respectively, for construction of novel therapies in the manners to be discussed.

Novel OSES-derived cancer treatments which attempt to switch cancer stem line mitosis from symmetric to asymmetric (thereby altering tumor growth kinetics for the better) include certain methods designed to activate the native asymmetric mitotic program inherent in all stem cells (and thus in all cancer stem line cells). This may be accomplished at the level of: i) ligand-receptor binding, or ii) beyond (e.g., signal transduction, transcription activation/inhibition, "bottlenecks" such as somatic allelic pairing, or unequal distribution of factors to daughter cells) (see Table 1), with special attention to iii) comprehensive combination therapy utilizing multiple points of intervention in the asymmetric mitotic pathway, possibly but not necessarily used in coordination with standard chemotherapies so as to simultaneously target both the cancer stem line as well as its progeny.

As will be discussed, such interventions can be in the form of delivery to a cancer stem line of native factors (e.g., ligands, receptors, downstream intracellular elements) that normally drive asymmetric stem cell mitosis or, alternatively, delivery of artificially constructed factors designed to block native factors that normally inhibit asymmetric stem cell mitosis. As will be discussed, both of these therapies upon introduction to a cancer stem line should result in activation of its asymmetric mitotic pathway.

In addition, an alternative OSES-derived approach to cancer therapy will be presented in subsection 3) whereby a cancer stem line (rather than be forced to undergo asymmetric mitosis) is paradoxically frozen in a symmetric mitotic program but concomitantly forced to differentiate (in other words, the normally tightly linked processes of differentiation and asymmetric mitosis are uncoupled)—a novel therapy which attempts to completely eradicate a cancer stem line, as win be discussed.

i) Activation of Asymmetric Cancer Stem Line Mitosis at the Ligand-Receptor Level Section (I.) describes the use of known differentiation-inducing agents (e.g., ATRA) but in a novel (OSES-derived) dosing manner for the purpose of inducing asymmetric cancer stem line mitosis in cancer treatment, e.g., at differing dosages and dosing intervals. This section (II.) concerns the design of new more specific differentiation-inducing therapies for cancer, based on knowledge of the native pathway of asymmetric stem cell mitosis.

As mentioned, the pathway to asymmetric stem cell mitosis is initiated by locally-acting differentiation-inducing factors which bind stem cell receptors—an action that in turn leads to signal transduction resulting ultimately in asymmetric mitotic stem cell division (Table 1, FIG. 4). Accordingly, it follows from these ideas that one novel method of cancer therapy would be to deliver such native locally-acting differentiation-inducing factors (i.e., those ligands that normally induce stem cells to undergo asymmetric mitosis) to a cancer stem line for the purpose of coercing a switch from symmetric to asymmetric cancer stem line mitosis. This would occur since a cancer stem line should expresses certain cell-surface receptors (having inherited them en bloc from normal stem cells) that lead to transduction of signals resulting in asymmetric mitosis.

Such native differentiation-inducing factors to be delivered to a cancer stem line would include, but not be exclusive to, gene products of Wnt, Wnt inhibitors, Hedgehog, Transforming growth factor, Epidermal growth factor among others (some of the receptors of which are listed in section (a) of Table 1). Identification of additional ligands which act in normal tissue development in a stem cell milieu will serve to add to this list of potential therapeutic effectors. Specifically, such factors, if properly delivered to a cancer stem line, will function as highly-specific therapeutic effectors of asymmetric cancer stem line mitosis (in an analogous fashion to their native role as inducers of asymmetric mitosis in normal stem cells). Such factors could be injected directly into a tumor, or given intravenously (as is done with ATRA). Additional modifications to such ligands may be necessary to promote their stability for use as drugs—a process familiar to those skilled in the art of drug design and delivery.

Another method of activating, in a cancer stem line, the ligand-receptor portion of the asymmetric mitotic pathway would be via delivery, to a cancer stem line, not of ligand but of its cognate receptor (i.e. one which normally transduces signals that cause stem cells to undergo asymmetric mitosis) (section (a) of Table 1). This method may be more advantageous than delivering ligands in that it may more "permanently" effect asymmetric cancer stem line mitosis without the requirement for prolonged therapy (as would be necessary when delivering differentiation-inducing ligands whether native or otherwise whose transduction effects are transient). In other words, targeted delivery of factors which cause an irreversible switch in the cancer stem line to permanent (rather than transient) metric mitosis would be preferred. This would involve for example, but not be exclusive to, delivery to a cancer stem line of a constitutively active receptor (e.g., via gene-directed therapy) which induces downstream events that normally lead to asymmetric mitosis in stem cells.

For example, by the OSES model, delivery to a cancer stem line of a constitutively active receptor which normally functions in transduction of signals leading to asymmetric stem cell mitosis should result in a switch to asymmetric cancer stem line mitosis. In general, in vitro delivery (via infection or transfection) of genes encoding cell receptors can be used to activate pathways downstream of such receptors in host cells—a method which has been previously and extensively described in other circumstances. By the OSES model, infection specifically of a cancer stem line, in vivo, would require utilization of current gene therapy techniques—a technology which continues to be perfected by those skilled in the art. At present, gene-directed therapies have used both viral (e.g., adenovirus, adeno-related virus, retrovirus) as well as non-viral means of delivery (e.g., naked DNA, chromosomal, or liposomal) (Calos, "The potential of extra chromosomal replicating vectors for gene therapy", *Trends Genet.,* 12:463-466 (1996)). Accordingly, an OSES-derived gene therapy would involve delivery of a receptor-encoding gene (as part of either a viral or non-viral construct) into a cancer stem line either via injection into a tumor or possibly intravenously. Following administration of such a drug, infection of a cancer stem line with the constitutively active receptor would be expected to lead to constitutive switch from symmetric to asymmetric mitosis in the cancer stem line thereby permanently altering tumor growth kinetics. Possible receptors to use for such novel OSES-derived therapy include, but are not exclusive to, the mammalian homologs of *Drosophila* frizzled (i.e., Wnt receptor) and smoothened (i.e., Hedgehog receptor), PTC, as well as receptors for Transforming and Epidermal growth factors (Perrimon, "Serpentine Proteins Slither into the Wingless and Hedgehog Fields", *Cell,* 86:513-516 (1996)). Identification of other receptors which normally act in induction of asymmetric stem cell mitosis (e.g., via investigation of normal tissue development) will add to the list (section (a) of Table 1) of possible therapeutic effectors of asymmetric cancer stem line mitosis in the manner described.

It should be noted that these OSES-derived therapeutic goals differ significantly from those espoused by current cancer gene therapists who have sought to destroy or correct mutant cells (i.e., rather than force a relatively mutationally-spared cancer stem line to regress, as directed by the OSES model).

Certain technological difficulties associated with gene therapy in general are shared by both current gene therapists as well as by the novel OSES-based methods proposed here. For one, improved targeting of gene therapy to stem cells has been a goal for current gene therapists and likewise would be also be the case for OSES-based therapies. Targeting stem cells is important for classical uses of gene therapy because it permits permanent gene introduction (i.e. into an immortal cell type) without the need for multiple treatments (which is associated with complications such as tolerance by virtue of acquired immunity to the viral vector). OSES-derived methods would also benefit from targeting stem cells as it would similarly limit the number of necessary treatments as well as potential toxicities to non-stem cells. Such technological advances in stem cell targeting may be assisted by further study of stem cell expression profiles (e.g., following stem cell cloning and expression analysis) in order to identify stem cell-specific factors to target. In addition, differential viral infection of stem cells versus non-stem cells may also provide information on certain stem cell-specific targets to exploit for therapy. For example, polyomavirus, papillomavirus, parvovirus, Epstein-Barr virus, and cytomegalovirus all display elevated viral gene expression and gene amplification in differentiating cells while only low level episomal DNA maintenance in stem cells (Villarreal, "Relationship of Eukaryotic DNA Replication to Committed Gene Expression: General Theory for Gene Control". *Microbiol. Rev.,* 512-542 (1991)). Elucidation of those intracellular host factors involved in episomal maintenance might provide potential targets for stem cell (and thus cancer stem line) identification and therapeutic delivery.

It should be noted, however, that OSES-derived therapies require the additional ability to be able to distinguish normal stem cells from symmetrically-dividing ones (i.e., cancer stem line). This may be difficult since the two likely express many of the same genes and thus may not be readily distinguishable (other than by their differences in growth kinetics). In other words, it is conceivable that both stem cells and a cancer stem line share many of the same targets and thus would both be concomitantly infected by a given (viral or non-viral) vector for gene therapy. Determination of the differences in gene products segregated in asymmetric versus symmetric mitosis may provide a feasible means to distinguish normal stem cells from a cancer stem line—and thus to exploit for therapeutic gene delivery (to be discussed in more detail in the section (III). One may also glean expression differences between normal stem cells and a cancer stem line for which to exploit for therapeutic purposes by cloning these cell populations and performing expression analyses (e.g., via subtraction hybridization, a well described technique to determine expression differences between tissues). It is also conceivable that toxicity associated with this type of novel OSES-based therapy (i.e., induction of asymmetric cancer stem line mitosis) may not be very significant for several reasons. Firstly, one of the major reasons classic gene therapy has encountered difficulties in infecting normal stem cells is because of architectural constraints (i.e., stem cells are sequestered within environmental niches)—a condition, which ironically might actually be advantageous for OSES-based therapy. More specifically, OSES-derived gene therapy (targeted to both normal stem cells as well as a cancer stem line) might preferentially target a cancer stem line because the disorganized architecture of a tumor may actually act as a less significant barrier than a normal well-defined stem cell niche. In this way, the technical difficulties encountered by classical gene therapies could be exploited by OSES-based therapies. There is an additional reason why the toxicity to normal stem cells associated with this type of therapy (i.e., induction of asymmetric cancer stem line mitosis) may not be very significant. Namely, considering that normal stem cells are presumably already dividing via asymmetric mitosis anyway, therapy designed to induce asymmetric mitosis would not be expected to change their behavior—thus no toxicity. However, other OSES-based therapies (that do not simply induce asymmetric mitosis), to be discussed in subsection 3), may be more toxic to normal stem cells than the therapy described in this section and thus warrant more specific delivery to the cancer stem line (see Section III.).

ii) Activation of Elements Downstream of Ligand Receptor Interactions to Induce Asymmetric Cancer Stem Line Mitosis As mentioned another OSES-derived method of inducing a cancer stem line to undergo asymmetric mitosis would involve activation (in a cancer stem line) of those elements downstream of ligand-receptor binding that normally play a role in signal transduction leading ultimately to asymmetric mitotic division of stem cells. A number of genes and gene products involved in asymmetric mitosis have been identified (see Table 1, Table 2, Table 3 and Section II, subsection 2)) and may provide potential targets for therapeutic manipulation. More specifically, activation of factors which promote asymmetric mitosis or, alternatively, inhibition of factors which drive symmetric mitosis are each methods which can be used to effect reversion of a cancer stem line from exponential to arithmetic growth. One method by which this could be accomplished is via delivery to a cancer stem line of a gene itself that normally activates the asymmetric pathway or inhibits the symmetric mitotic pathway (downstream of ligand-receptor binding) in adult stem cells (specific examples will be given in the next subsection, iii). A non-exhaustive list of such gene products is contained in Table 1, Table 2 and Table 3, as well as Section II, subsection 2) of this application. Identification of additional products involved in the asymmetric mitotic program downstream of receptor binding (e.g., likely to be gleaned from ongoing investigation of normal development) will add to this of potential effectors of OSES-derived cancer therapy. Delivery of such genes would involve methods of gene therapy (e.g., utilization of viral or non-viral vectors) via injection or intravenous use in a similar manner as to that described in the previous subsection (i, for genes encoding receptors). Perfection of such techniques to maximize delivery to a specific cell population (in this case a cancer stem line) while minimizing side effects is a major priority, as mentioned before, for both classic as well as OSES-derived methods of gene therapy.

Again, to reiterate, these OSES-derived therapeutic goals differ significantly from those espoused by current cancer gene therapists who have sought to destroy or correct mutant cells (i.e. rather than force a relatively mutationally-spared cancer stem line to regress, as directed by the OSES model).

Knowledge of downstream effectors of asymmetric mitosis can also be exploited for an alternative OSES-derived method of cancer therapy. Namely, in addition to using positively-acting factors themselves (i.e., those factors that drive asymmetric mitosis) as vehicles of gene therapy for cancer, knowledge of the DNA coding sequences of those factors that normally drive symmetric mitosis (or inhibit asymmetric mitosis) can also be used as templates for the construction of elements that will block their inhibitory function (i.e. thereby also leading to asymmetric mitosis of a cancer stem line). For example, such methods would include but not be exclusive to, therapies that utilize RNA-based antisense or ribozyme modalities or other newer technologies which may arise that allow design of factors that specifically block the function of certain targeted gene products. Both of these mentioned methods take advantage of sequence information (of a targeted nucleic acid) in order to construct a highly specific therapeutic agent which will bind to its cognate (i.e., target) messenger RNA species and inactivate it before it can be properly translated into functional protein. In this manner, a specific gene product (e.g., one that normally inhibits asymmetric mitosis) can be blocked. It should be noted that there have been a number of recent advances in the technical aspects of these therapies (Ellington et al, "Ribozymes in Wonderland", *Science,* 276:546547 (1997); Roush, "Antisense aims for a renaissance", *Science,* 276:1192-1193 (1997)), which should more readily allow for their exploitation for novel OSES-derived uses. Antisense and ribozyme therapies have already been shown to be efficacious in preliminary cell culture experiments but compelling evidence for any clinical utility remains to be demonstrated. Others have indeed proposed ribozyme therapy for the treatment of cancer (e.g., via viral or non-viral delivery systems) and have used it successfully in preliminary in vitro experiments (Kashani-Sabet et al, "Suppression of the Neoplastic Phenotype in Vivo by an Anti-ras Ribozyme", *Cancer Res.,* 54:900-902 (1994)). However, it should be emphasized that such experiments were performed and viewed with the conventional model of cancer in mind whereby highly proliferative mutant cells were targeted—which according to the OSES model, is the wrong cell population to target and thus such therapy will leave a cancer stem line intact. Thus, it is proposed here that such therapies or related-ones should be used for novel purposes whereby a slow-growing relatively mutationally-spared cancer stem line is targeted.

In addition, in vitro evolution offers another method of perfecting the specificity of ribozymes, a method which can also be used to target non-nucleic acid (e.g., non-messenger RNA) species, e.g., proteins (involved in asymmetric mitosis) (Beaudry and Joyce, "Directed evolution of an RNA enzyme", *Science,* 257:635-641 (1992)). Moreover, newer technologies may soon improve on the specificity of action of antisense and ribozyme RNA-based therapies. As mentioned, by the OSES model, such therapies should be geared toward targeting the relatively mutationally-spared cancer stem line as described above. Like delivering genes themselves (i.e., those that activate asymmetric mitosis downstream of ligand-receptor binding) to a cancer stem line, delivery of specifically constructed inhibitors (e.g., but not exclusive to, antisense or ribozyme agents) to a cancer stem line can be performed via viral or non-viral means, as described by those skilled in the art, for the purpose of blocking specific factors that normally either inhibit asymmetric mitosis or activate symmetric mitosis thereby leading to the desired therapeutic effect of asymmetric cancer stem line mitosis. Specific examples will be discussed in the following subsection, (iii).

As discussed in the previous subsection (i), targeting of stem cells, and in particular symmetrically-dividing ones (i.e. the cancer stem line) should be the therapeutic goal.

iii) Combination Therapy to Force Asymmetric Cancer Stem Line Mitosis

Considering the complexity of the asymmetric mitotic pathway (Table 1, Table 2, and Table 3), it is likely that activation of such a pathway in a cancer stem line will require multiple points of intervention. With this in mind, a combination of gene-delivered therapy and gene product-inhibiting therapy (e.g., antisense, ribozyme) may be necessary to induce a cancer stem line to assume arithmetic growth kinetics.

Of course, attempts to intervene at "bottlenecks" in this pathway will be advantageous as they will necessitate fewer therapeutic maneuvers. For example, delivery to a cancer stem line of 1) factors that promote allelic pairing/exchange (e.g., but not exclusive to, zeste, SNRPN, and others) via gene therapy—by methods previously discussed, or 2) template-constructed (e.g., but not exclusive to, antisense or ribozyme) inhibitors of factors which block allelic pairing/exchange (e.g., but not exclusive to zeste-inhibitors, SNRPN-inhibitors) by methods previously discussed may alone or in combination lead to a switch from symmetric to asymmetric cancer stem line mitosis. It should be noted that those factors (mentioned in the previous sentence) preliminarily deemed to promote allelic pairing/exchange may actually block allelic pairing/exchange (and vice versa). In other words, the mechanisms of allelic pairing/exchange await further clarification, and thus these mentioned examples of therapy may need to be reversed.

While the mechanisms of gene products specifically involved in allelic pairing/exchange await further description, the mechanisms of action of other gene products involved in the general (i.e., non-"bottleneck" portion) of the asymmetric mitotic pathway are now beginning to emerge. One such pathway which leads to asymmetric mitosis, namely the Wnt signaling pathway, has begun to emerge from pooled data derived from a number of different species. Wnt gene products are involved in normal embryonic and adult tissue development (Nusse and Varmus, "Wnt genes", *Cell* 69:1073-1087 (1992)). One mechanism of action of these factors is to mark cell polarity and/or permit inherent cell polarity—a maneuver that leads ultimately to asymmetric mitotic divisions (Herman et al, "The *Caenorhabditis elegans* gene lin-44 controls the polarity of asymmetric cell divisions", *Development,* 120: 1035-1047 (1994)). A signaling pathway by which this process occurs is now becoming clearer: locally-acting Wnt proteins bind to their receptor (frizzled, in *Drosophila*) leading eventually to activation of transcription factors (e.g., LEF-1/XTCF-3 in *Xenopus*) and then to activation of certain cell fate-determining genes (e.g., engrailed, in *Drosophila*) some of which themselves, or downstream products thereof, are unequally segregated to daughter cells. Within this signaling pathway are numerous intermediate positively-acting factors such as APC and beta-catenin (mammalian), as well as certainly negatively-acting ones such as GSK-3-beta (*Xenopus*)—an inhibitor of beta-catenin (Kuhl et al, "Wnt signalling goes nuclear", *Bioessays,* 19:101-104 (1997)). It is proposed here that the binding of certain Wnt proteins to their receptors (on stem cells of adult tissues) leads to activation of the mentioned pathway and asymmetric stem cell mitosis. By this model, symmetrically-dividing stem cells (i.e., a cancer stem line) would maintain inhibition of the Wnt pathway but would be susceptible to having it therapeutically up-regulated (which would lead to a switch from symmetric to asymmetric cancer stem line mitosis).

Accordingly, for the purpose of treating cancer via novel OSES-derived therapy, one is left with multiple possible sites in the Wnt pathway at which to intervene. For example, in order to force a symmetrically-dividing cancer stem line to divide asymmetrically, one could activate positively-acting factors in the Wnt pathway (e.g., but not exclusive to APC, beta-catenin, LEF-1/XTCF-3) via gene therapy, i.e. delivery of the coding sequences of such factors to a cancer stem line in a non-viral or viral construct, as discussed in the last 2 subsections (i, ii). Alternatively, one may attempt to block those factors which normally inhibit the native Wnt pathway (e.g., but not exclusive to, GSK-3-beta), e.g., by designing a "tailor-made" antisense or ribozyme agent specific for the GSK-3-beta mRNA species and delivering such a construct to a cancer stem line by methods discussed in the last subsection (ii). By blocking this gene product (i.e. a gene product that presumably inhibits asymmetric mitosis), a cancer stem line would be forced to assume asymmetric mitotic division. Identification of other factors in the Wnt pathway will add to the list of potential genes to use in gene therapy as activators of asymmetric cancer stem line mitosis, or as templates for the construction of (e.g., but not exclusive to, antisense or ribozyme) inhibitors to block symmetric mitosis.

In addition to the Wnt pathway, there are also cumulative data emerging concerning other asymmetric mitosis-related pathways. For example, there is evidence that one highly conserved factor (cdc42) involved in yeast structural asymmetry has a downstream kinase target in humans. Such a candidate kinase (Kp78) in humans appears to be related to a gene (par-1) in nematodes which is known to affect the asymmetric action of another nematode factor (SKN-1) which itself is related to the yeast HO-inhibiting factor (Ash-1p). Thus, assuming the likely existence of a conserved human homolog for each of these genes, a potential pathway emerges whereby structural asymmetry mediated by cdc42 leads to the asymmetric action of a human kinase (Kp78) which activates a human SKN-1-homolog that in turn activates a transcription factor (e.g., human Ash-1p-related homolog) that effects expression of cell fate-determining genes (e.g., human HO-related gene product, possibly also like in yeast is involved in chromosome pairing/strand exchange). The involvement of such a gene in pairing/-exchange suggests it may act at a key "bottleneck" in the asymmetric mitotic pathway (FIG. 4). Accordingly, OSES-derived therapy might be constructed to activate positively-acting factors (e.g., cdc42, Kp78/par-1, SKN-1, HO), or block negatively-acting factors (e.g. Ash-1p) by the methods of gene therapy and gene-inhibitor (e.g., antisense and ribozyme) therapy described in this and previous subsections. It should also be noted that those factors (mentioned in the previous sentence) deemed to be positively-acting may actually be negatively-acting in asymmetric mitosis, and vice versa, and were placed in these categories here only as a preliminary gesture and are not intended to be final categorizations of gene function. Such final categorizations await additional evidence from investigational scientists working in these areas of developmental biology.

Interestingly, human Kp78, which as mentioned is related to nematode par-1, has been found to be deleted in certain human cancers—a finding consistent with the OSES model and not necessarily predicted or expected by conventional models (Way et al, "Cell polarity and the mechanism of asymmetric cell division", *Bioessays,* 16:925-931 (1994); Lin et al, "Neuroblasts: a model for the asymmetric division of stem cells", *Trends Genet.,* 13:33-39 (1997)). In other words, by the OSES model deletion of an asymmetric mitosis-related gene (e.g., Kp78) might be expected to be found among a sub-population of peripherally-located progeny of a cancer stem line, i.e., where selection for differentiation-defectiveness occurs. Conventional models, however, predict deletions to occur mostly in classic tumor suppressor genes (e.g., RB-1, TP53, BRCA-1) and thus KY78 deletion would be unexpected.

The OSES model would predict that other genes involved in normal tissue development (and more specifically in the induction of asymmetric stem cell mitosis) should also be found to be altered in progeny of the cancer stem line. Interestingly, there is evidence that PTC (patched homolog) is mutated in human basal cell carcinomas, Wnt genes are involved in mammary tumorigenesis, and alteration of hedgehog expression may contribute to neoplasia (Johnson et al, "Human Homolog of patched, a Candidate Gene for the Basal Cell Nevus Syndrome", *Science*, 272:1668-1671 (1996); Tsukamoto et al, "Expression of the int-1 gene in transgenic mice is associated with mammary gland hyperplasia and adenocarcinomas in male and female mice", *Cell*, 55:619-625 (1988)).

As previously mentioned, there is increasing evidence that gene products involved in the asymmetric mitotic pathway are highly conserved in both structure and function among distant species (e.g., cdc42 in yeast, nematode, and human) (Way et al, "Cell polarity and the mechanism of asymmetric cell division", *Bioessays*, 16:925-931 (1994); Lin et al, "Neuroblasts: a model for the asymmetric division of stem cells", *Trends Genet.*, 13:33-39 (1997)). Accordingly improved description of the asymmetric mitotic pathway in cells of non-human organisms will likely provide insight into the same process in human cells. Likewise, identification of additional gene products involved in these processes in any of a number of different organisms will not only help describe the process of asymmetric mitosis but will also provide additional molecular probes as well as key sequence information to use for the purpose of cloning their human homologs. In addition to some of the above mentioned pathways of asymmetric mitotic division, there are certainly others to be more well-described in the near future. Some of these may include the hedgehog, patched, transforming and epidermal growth factors pathways (Table 1). However, this is certainly not intended to be an exhaustive list.

It is expected, based on the teachings in this application, that one skilled in the art will be able to select other suitable targets, e.g., those mentioned above as well as other gene products (identified in the future likely via, but not exclusive to, study of developmental and stem cell biology) for which to construct OSES-based cancers therapies. More specifically, knowledge of gene products involved in asymmetric mitosis in human cells will in turn, as directed by the OSES model, provide additional targets within a cancer stem line for which to therapeutically enact a permanent switch from symmetric to asymmetric mitosis. As mentioned, identification of such mitosis-related genes will allow their use in, but not exclusive to, gene therapy, as well as provide sequence information necessary for the construction of "tailor-made" inhibitors (e.g., anti-sense or ribozyme therapies).

As discussed in the previous subsection (i), targeting of stem cells, and in particular symmetrically dividing ones (i.e. the cancer stem line) should be the therapeutic goal.

It should be well-noted that this is not intended to be an exclusive description of all possible methods which could be derived from the OSES model to effect asymmetric cancer stem line mitosis, but rather to serve as examples of some of a number of possible ways in which such novel cancer therapies could be reduced to practice. As alluded to earlier, OSES-based therapies could be used alone or in combination with standard chemotherapies as a 2-pronged attack to both contain the cancer stem line as well as concomitantly lower the tumor burden, respectively.

EXAMPLE 2

A patient is found to have pancreatic cancer by conventional detection techniques (e.g., CT scan and biopsy). A ribozyme is constructed that specifically blocks a factor (e.g., GSK-3-beta) that normally inhibits asymmetric mitosis in pancreatic epithelial stem cells. The ribozyme is placed within a viral vector and delivered intravenously to the patient. This therapeutic vector will force stem cells of pancreatic origin to divide asymmetrically thus causing the cancer stem line fueling the pancreatic tumor to assume arithmetic growth kinetics (see FIG. 3B) without significant toxicity to normal pancreatic epithelial stem cells that are dividing asymmetrically anyway.

3) Induction of Irreversible Stem Line Differentiation

As mentioned, one novel OSES-derived method of treating cancer (as described in subsection 2) is to force a cancer stem line to switch from symmetric to asymmetric mitotic division. However, in designing such a therapy, it should be remembered that when a cancer stem line is induced to differentiate it does so in an asymmetric fashion thereby preserving an immortal stem line which does not itself differentiate (i.e., one daughter cell remains as a cancer cell thereby maintaining the cancer stem be, while one daughter cell differentiates) (FIGS. 3A and 3B). Accordingly, an alternative OSES-based novel therapy for cancer would be geared toward total eradication of the cancer stem line. Such a therapy might include, but not be exclusive to, switching a cancer stem line from a symmetric program of proliferation (not to an asymmetric mitotic program but rather) to a symmetric program of differentiation whereby both daughter cells of a cancer stem cell are forced to terminally differentiate thereby potentially resulting in a complete eradication of the stem line and cancer cure (FIGS. 3A and 3B).

In order to induce a cancer stem line to undergo symmetric differentiation, one may employ methods such as but not exclusive to: i) paradoxical inhibition of the asymmetric mitotic machinery thereby effectively "freezing" a cancer stem line in a symmetric mitotic mode, followed by ii) induction of cancer stem line differentiation which must then proceed symmetrically. This is technique would effectively uncouple the normally tightly-linked processes of asymmetric mitosis and differentiation. It should be noted that asymmetric mitosis and differentiation, while tightly-linked processes in mammals, are often independent processes in lower eukaryotes (Horvitz et al, "Mechanisms of Asymmetric Cell Division: Two Bs or Not Two Bs, That is the Question", *Cell*, 68: 237-255 (1992); Villarreal, "relationship of eukaryotic DNA replication to committed gene expression: general theory for gene control", *Microbiol. Rev.*, 512-542 (1991)).

i) Paradoxical Inhibition of Asymmetric Cancer Stem Line Mitosis

One means of blocking asymmetric mitosis of a cancer stem line is the reverse of that mentioned in the previous subsection 2), i.e. block rather than activate those factors which drive asymmetric mitosis and/or activate rather than block those factors inhibit asymmetric mitosis (Table 1). This may be accomplished in a similar manner as that mentioned in the previous section, i.e. via gene-delivered therapy or gene product-inhibiting therapy (e.g., antisense, ribozyme) to a cancer stem line but with the opposite desired effect. For example, rather than deliver to a cancer stem line a receptor that normally activates asymmetric mitosis (e.g., but not exclusive to, frizzled), one should deliver an inhibitor of this pathway (e.g., but not exclusive to GSK-3-beta or Ash-1p). Alternatively, one could construct an "tailor-made" inhibitor (e.g., antisense or ribozyme) to a positively-acting factor (e.g., but not exclusive to, beta-catenin), or a "bottleneck" element (e.g., but not exclusive to, elements that promote allelic pairing/exchange such as SNRPN) in the asymmetric mitotic pathway. It should be noted that blocking the asymmetric mitotic machinery of a cancer stem line is a seemingly risky approach because it will effectively "freeze" the cancer stem line, paradoxically, in an exponential growth phase. This method of therapy has the opposite goal to that proposed in the previous subsection 2) which seeks to switch a cancer stem line to an asymmetric mitotic mode. Accordingly, by this alternative method, a cancer stem line "frozen" in a symmetric mitotic mode, if left unchecked, would continue to proliferate exponentially. Thus, this initial intervention must be promptly followed by induction of cancer stem line differentiation—which would then proceed without the asymmetric machinery (i.e., would proceed in a symmetric fashion since the asymmetric machinery has been blocked). Accordingly, cell fate (i.e., differentiation-determining) elements will be equally segregated to daughter cells thereby extinguishing the immortal stem line.

ii) Induction of Symmetric Cancer Stem Line Differentiation

Following a block to asymmetric cancer stem line mitosis as described above in (i) (i.e., freezing a cancer stem line in a symmetric mitotic mode), differentiation-induction should then proceed symmetrically resulting in eradication of the cancer stem line. By this method, the normally tightly linked processes of asymmetric mitosis and differentiation become uncoupled.

There are a number of possible methods by which to induce cancer stem line differentiation. For example, as mentioned in the previous subsection 2), delivery to a cancer stem line of differentiation-inducing agents (e.g., but not exclusive to, ATRA), differentiation-inducing ligands (e.g., but not exclusive to Wnt, see Table 1) or receptors in the asymmetric mitotic pathway (e.g., but not exclusive to frizzled, see Table 1) via the methods described in the previous section (while proposed to induce asymmetric mitosis when a cancer stem line is not "frozen" in a symmetric mitotic mode, as in subsection 2), is proposed here (as a result of uncoupling asymmetric mitosis from differentiation) to induce symmetric differentiation. Activation of positively-acting (or inhibition of negatively-acting) elements in the asymmetric mitotic pathway downstream of ligand-receptor binding, by the methods described in the previous subsection 2) (e.g., gene therapy, or antisense/ribozyme therapy), may also be employed in this scenario to induce differentiation in a cancer stem line. In this case, however, it would behoove one to intervene at the more upstream points (e.g., prior to "bottlenecks") which are dominated more by differentiation-related processes, rather than at the more downstream points (e.g., "bottlenecks" or beyond) which are dominated more by asymmetric mitotic-related processes. In other words, the goal is to induce differentiation products so that they may be equally delivered to both daughter cells. Thus, it is a hypothesis of the OSES model that differentiation induction of a stem cell normally triggers an asymmetric mitotic mechanism such that a therapeutic block to this trigger will allow differentiation to occur without activation of the asymmetric machinery (i.e. and thus symmetrically).

There may be additional methods by which to induce a cancer stem line to activate differentiation-related gene products. For example, it has been shown that starvation can induce cells to become growth quiescent and at times differentiate (or under certain conditions undergo apoptosis, i.e., programmed cell death) (Hoffman and Lieberman, "Molecular controls of apoptosis: differentiation/growth arrest primary response genes, proto-oncogenes, and tumor suppressor genes as positive and negative modulators", *Oncogene*, 9:1807-1812 (1994); Sherley et al, "Expression of the wild type p53 antioncogene induces guanine nucleotide-dependent stem cell division kinetics", *Proc. Natl. Acad. Sci. USA*, 92:136-140 (1995)). Considering evidence that certain starvation-induced responses (e.g., growth arrest/differentiation) occur asymmetrically (i.e., with preservation of a stem line of cells capable of proliferative growth following discontinuation of starvation conditions) (Sherley et al, "Expression of the wild type p53 anti-oncogene induces guanine nucleotide-dependent stem cell division kinetics", *Proc. Natl. Acad. Sci. USA*, 92:136-140 (1995)), it is proposed here that starvation conditions may approximate differentiation-induction and thus be employed for the purposes of novel OSES-based cancer therapy. In other words a starvation-treated cancer stem line, following prior blockage of the asymmetric mitotic machinery of a cancer stem line (by the methods described in this section), would (like that for a differentiation-induced cancer stem line "frozen" in a symmetric mitotic mode) also be expected to cause growth arrest/differentiation (or apoptosis) of a cancer stem line in a symmetric manner thereby resulting in its eradication.

A related case may provide some preliminary support for such novel proposals. It has been previously shown that certain starved cells in culture undergo a growth quiescent phase which has been better characterized as an asymmetric mitotic/differentiation-like program (Sherley et al, "Expression of the wild type p53 anti-oncogene induces guanine nucleotide-dependent stem cell division kinetics", *Proc. Natl. Acad. Sci. USA*, 92:136-140 (1995). Interestingly, other cell types in culture, which undergo a similar growth quiescent phase in response to starvation conditions, undergo apoptosis (presumably an alternate branch of the differentiation pathway) if their mitotic machinery is altered (e.g., by c-myc deregulation) (Evan et al, "Induction of apoptosis in fibroblasts by c-myc protein", *Cell*, 69:119-2128 (1992); Hermeking and Eick, "Mediation of c-Myc-induced apoptosis by p53", *Science*, 265:2091-2093 (1994)). It is proposed here that this differentiation (in this case apoptotic) response to starvation by c-myc deregulated cells is analogous to the hypothesized (symmetric) differentiation response to starvation by a cancer stem line "frozen" in a symmetric mitotic mode. In other words, it is proposed here that c-myc deregulation in cells in culture approximates a block to the asymmetric mitotic machinery in a cancer stem line, both of which scenarios would respond to starvation by undergoing a terminal process (e.g., apoptosis or symmetric differentiation, respectively).

Starvation has been induced by a host of methods including, but not exclusive to alterations in enzymes involved in nucleic acid synthesis (e.g., GTP), removal of essential growth factors, certain drugs and chalones (Hoffman and Lieberman, "Molecular controls of apoptosis: differentiation/growth arrest primary response genes, proto-oncogenes, and tumor suppressor genes as positive and negative modulators", *Oncogene*, 9:1807-1812 (1994); Sherley et al, "Expression of the wild type p53 anti-oncogene induces guanine nucleotide-dependent stem cell division kinetics", *Proc. Natl. Acad. Sci. USA*, 92:136-140 (1995). Accordingly, these as well as other strategies not mentioned here could be used to induce cancer stem line starvation. Preliminary testing of this method in cultured cells would involve initially "freezing" a cancer stem line a symmetric mitotic mode (by methods described in this section), and then inducing either differentiation (by the methods described in this section), or starvation (by addition of certain agents used by investigators to induce starvation, some of which are mentioned in this section). Measurement of growth kinetics of the stem line of such cells in culture, a technique previously described (Sherley et al, "Expression of the wild type p53 anti-oncogene induces guanine nucleotide-dependent stem cell division kinetics", *Proc. Natl. Acad. Sci. USA*, 92:136-140 (1995)), will determine whether a shift to symmetric differentiation/apoptosis has occurred. Such therapies could then be utilized in genetically-altered mouse models of cancer, using gene therapy vehicles (e.g., viral or non-viral), as mentioned, and then in humans.

It should be well-noted that this is not intended to be an exclusive description of all possible methods which could be derived from the OSES model to effect terminal differentiation/apoptosis, but rather to serve as examples of some of a number of possible ways in which such novel cancer therapies could be reduced to practice. As discussed in the previous subsection (i), targeting of stem cells, and in particular symmetrically-dividing ones (i.e. the cancer stem line) should be the therapeutic goal. In addition, as alluded to earlier, OSES-based therapies could be used alone or in combination with standard chemotherapies as a 2-pronged attack to both destroy the cancer stem line as well as concomitantly lower the tumor burden, respectively.

EXAMPLE 3

A patient is found to have lung cancer by conventional detection techniques (e.g., CT scan and biopsy). A ribozyme is constructed that specifically blocks a factor (e.g., SNRPN) that normally activates asymmetric mitosis in lung epithelial stem cells. The ribozyme is placed within a viral vector and delivered intravenously to the patient. This therapeutic vector will force stem cells of lung origin to divide symmetrically thus causing the cancer stem line fueling the lung tumor to assume exponential growth kinetics. This maneuver is quickly followed by intravenous administration of a starvation-inducing agent (e.g., inhibitor of nucleic acid synthesis) which forces the cancer stem line to initiate its differentiation program but in a symmetric manner thereby extinguishing the stem line (see FIG. 3C). Toxicity to normal stem cells may be minimal due to their environmental sequestration. Efforts to limit this toxicity further are discussed in the next section (III.).

III. Targeting Symmetrically-Dividing Stem Cells (Cancer Cells) while Sparing Asymmetrically Dividing (Normal) Stem Cells.

As discussed in section II., (2), end of subsection (i), technological advances in gene therapy will allow OSES-based cancer therapy to be better directed toward stem cells (by some of the means discussed) and more specifically toward the cancer stem line. While toxicities based on methods discussed in section II., (2) may not be very significant (since such methods would simply force a nodal stem cell to undergo its native mitotic mode anyway, i.e., asymmetric mitosis), toxicities based on methods discussed in section II., (3) may be more significant since they could potentially also cause normal stem cells to undergo symmetric differentiation/apoptosis (i.e., eradication) thereby leading to an inability of certain tissues to renew themselves. Accordingly, it would be beneficial, at least for latter method of therapy, to avoid normal (asymmetrically-dividing) stem cells and just target the (symmetrically dividing) cancer stem line.

It is, however, conceivable, as previously mentioned, that because of architectural constraints (i.e. stem cells are sequestered within environmental niches), OSES-derived gene therapy (targeted to both normal stem cells as well as a cancer stem line) might preferentially target a cancer stem line because the disorganized architecture of a tumor may actually act as a less significant barrier than a normal well-defined stem cell niche. Experimental verification for such an idea is needed. In the meantime, efforts to distinguish normal stem cells from a cancer stem line for the purpose of therapeutic targeting is warranted.

There are several ways in which to preferentially target symmetrically-dividing stem cells (i.e. a cancer stem line) with OSES-based therapy while sparing normal (asymmetrically-dividing) stem cells. The following are possibilities, but are not intended to be comprehensive, as other possibilities undoubtedly exist or will exist when new technologies arise.

Firstly, determination of differences in cell surface antigens between a cancer stem line and normal stem cells may permit design of vectors (viral or non-viral) which can preferentially bind to those antigens solely on a cancer stem line. One may glean expression differences (with particular attention paid to cell surface antigens) between normal stem cells and a cancer stem line by cloning these cell populations and performing expression analyses (e.g., via subtraction hybridization, a well-described technique to determine expression differences between tissues), or by protein purification and comparison of respective cell surface antigens. In addition, investigation of the mechanisms by which certain viruses differentially infect and/or act in cells of differing mitotic modes may also yield gene product (e.g., cell surface antigens) specific to cells that divide symmetrically versus asymmetrically (Villarreal, "Relationship of Eukaryotic DNA Replication to Committed Gene Expression: General Theory for Gene Control", *Microbiol. Rev.,* 512-542 (1991)).

Secondly, rather than distinguishing a cancer stem line from normal stem cells for targeted therapy by virtue of differences in cell surface antigens, one may utilize expression differences in certain intracellular gene products. This would then allow the following novel technique: pre-treatment via delivery of a "tailor-made" pre-treatment factor (PTF) which: 1) binds an intracellular element maintained solely within a cancer stem line (i.e. and not in normal stem cells) and 2) is required (e.g., act as a cofactor) for the function of an OSES-based therapy (e.g., asymmetric mitosis-inhibiting factor, AMIF) to be given following this pre-treatment. Such a technique will allow non-targeted delivery of AMIF to both a cancer stem line as well as normal stem cells, but will ensure AMIF activity solely in a cancer stem line, by virtue of the presence of a "tailor-made" PTF (in a cancer stem line but not in normal stem cells) which is necessary for function. Following pre-treatment in this manner and subsequent delivery of the AMIF (which by this method would only be active in the cancer stem line and not in normal stem cells), induction of differentiation/starvation can proceed for the purpose of eradicating a cancer stem line while sparing normal stem cells. For design of a PTF, one must identify a suitable intracellular element that is cancer stem line-specific for which to specifically bind. Qualifying as cancer stem line-specific intracellular elements may be notch, numb, or other intracellular elements (see Table 1, Table 2, and Table 3) unequally segregated during asymmetric mitosis to the non-stem cell daughter (i.e., purged from normal stem cells), but which may also be equally segregated to both daughter cells during symmetric mitosis (see FIGS. 5A and 5B). Accordingly, design of a PTF to specifically bind such a cancer stem line-specific intracellular element may proceed, e.g., but not exclusive to, via use of known cofactor binding sites (of that particular intracellular element), or via in vitro evolution selecting for ribozymes which specifically bind (but do not cleave) a cancer stem line-specific intracellular element. In addition, the PTF must also be designed with a "tailor-made" moiety which as proposed would be required (e.g., act as a cofactor) for AMIF function. Such a moiety could be (or code for) a cofactor, chaperone, activating enzyme, activating ribozyme, cleavage ribozyme, or other factor which would activate or be necessary AMIF function. For example, if the AMIF were a ribozyme, then a portion of the PTF might be a ribozyme which cleaves or folds the AMIF at some point to make it active (see FIGS. 6A and 6B).

Novel Detection Methods Provided by the Invention

Conventional cancer screening methods include, among others: physical exam, mammography (breast cancer), PAP smear (cervical cancer), stool guaiac and colonoscopy (colon cancer), PSA (prostate cancer), skin surveillance (skin cancer), sputum analysis and chest X-ray (lung cancer), among others. For a positive test result, however, all of these methods unfortunately require that a significant number of cancer cells be present in the examined patient. Accordingly, such "early" detection methods are often too late. For example, approximately 30% of patients with "early" breast cancer without gross evidence of lymphatic spread who have undergone "complete" surgical resection will still develop recurrent disease at a later date. In addition, radiographically-detectable lung tumors are often incurable despite their seemingly "small" size. These disturbing findings indicate that conventional detection techniques do not identify cancer early enough.

By the OSES model, however, cancer cells are produced not by a gradual evolutionary process at the cellular level but rather via a one step switch in stem cell mitotic mode. Accordingly, a potentially detectable neoplastic lesion would be expected to be present prior to attaining the large size (in numbers of cancer cells) required by conventional detection techniques.

Identification of symmetrically-dividing stem cells (i.e. a cancer stem line) provides, according to the OSES model, a novel and extremely sensitive method for the early detection of cancer. In order to do this, one must identify elements which are specific to the cancer stem line and then design factors which will bind specifically to them—which themselves are readily detectable. This may be effected, e.g., by attaching a readily detectable moiety (e.g., a fluorescent tag or radionuclide) to a cancer stem line-specific binding factor. This technique swill enable a cancer stem line to be readily detected, e.g., by infusing such a cancer stem line-specific binding factor (with an attached detectable moiety) into a patient and then placing the patient into a total body scanner/developer which can sense the attached moiety (e.g., fluorescent tag or radionuclide) and record its presence and bodily location on film (e.g., this could be accomplished by using fluorescent-sensitive film, or a CT or MRI scanner). In this manner, the detection of tag (e.g., fluorescence, radionuclide) in aberrant patterns within a tissue (i.e., different from the patterns of normal stem cells within a tissue) would indicate a mass of symmetrically-dividing stem cells thereby detecting early carcinogenesis. Following identification of symmetrically-dividing stem cells (i.e., a cancer stem line), such a lesion could be treated locally with, e.g., with conventional therapy such as irradiation or surgical excision much earlier than would be possible by convention detection/treatment methods.

Factors specific to the cancer stem line would include: surface antigens, intracellular factors which are differentially atoned depending on mitotic mode (e.g., of the type unequally apportioned during asymmetric mitosis (e.g., but not exclusive to, notch, numb) as described previously in section (III.) (see FIGS. 5A and 5B). Construction of factors which will specifically bind to these cancer stem line-specific entities include monoclonal antibodies to surface antigens, as well as other specific binding factors such as co-factors, or constructed ribozymes or anti-sense RNA molecules of the types described in section (III.) which can be designed to bind (but designed not to cleave) cancer stem line-specific intracellular elements. Attachment of fluorescent moieties to monoclonal antibodies for the purpose of allowing visual detection of bound antibody is a method commonly used by those skilled in the art (e.g., immunohistochemistry) and may also be used in conjunction with bound co-factors or constructed ribozymes or antisense molecules.

It should be noted that, by the OSES model, the early neoplastic lesion (i.e., collection of symmetrically-dividing stem cells) could in theory arise as an aberrancy at any point in the development of a given tissue (e.g., during adult tissue genesis or even as early as embryogenesis when tissues are being formed). There are indeed some data that the initiation of certain cancers may occur much earlier than expected by conventional evolutionary models, i.e., during early tissue development—and thus potentially detectable at these early periods.

For example, there are reports that some young women exposed to radiation at a prepubescent age (prior to mammary gland development) have elevated rates of breast cancer in adulthood (Deng et al, "Loss of Heterozygosity in Normal Tissue Adjacent to Breast Carcinomas", *Science* (Washington D.C.), 274:2057-2059 (1996)). How radiation could be carcinogenic to a tissue which has not yet developed and is not yet proliferating is a concept not adequately explained by conventional models. However, since there is evidence that the normally clonal nature of stem cell micro-environments in developing tissues is a state created early in development (Gordon et al, "Differentiation and self-renewal in the mouse gastrointestinal epithelium", *Curr. Opin. Cell Bio.*, 6:795-803 (1994)), these findings of early radiation-induced breast cancer are consistent with the OSES model wherein alterations in the initial development of the gland due to irradiation damage can result in an altered stem cell milieu and thereby predispose to the aberrant birth of a symmetrically-dividing stem cell (i.e., cancer cell). This population of symmetrically dividing stem cells (i.e., cancer cells) may take years to emerge in numbers (and thus years to detect by conventional methods) but by the OSES model is, in theory, detectable much earlier.

While the mammary gland is unique in that it undergoes the majority of its development ex utero, other tissue types develop mostly in utero thereby making detection of aberrant development (i.e., symmetric stem cell mitosis/cancer) in other tissue types possible prior to pubescence and conceivably possible as early as during embryogenesis. Interestingly, as mentioned previously, there are a group of independently reported enigmatic findings that a subset of patients possess shared genetic alterations (e.g., loss of heterozygosity of WT-1 or hypermethylation of H19, loss of heterozygosity of breast cancer-related loci, and micro-satellite mutator phenotype defects) in both tumorous as well as synchronous non-neoplastic tissues (Chao et al, "Genetic mosaicism in normal tissues of Wilms' tumor patients", *Nature Genet.*, 3:127-131 (1993); Moulton et al, "Epigenetic lesions at the H19 locus in Wilms' tumor patients", *Nature Genet.*, 7:440-447 (1994). Deng et al, "Loss of Heterozygosity in Normal Tissue Adjacent to Breast Carcinomas", *Science* (Washington D.C.), 274: 2057-2059 (1996); Parsons et al, "Mismatch Repair Deficiency in Phenotypically Normal Human Cells", *Science* (Washington D.C.), 268:738-740 (1995)). These findings indicate that such genomic alterations shared by neoplastic and non-neoplastic tissues must have occurred in the common embryonic ancestor cell which gave rise to both the neoplastic cells as well as normal-appearing cells of the same tissue type. Conventional models would expect such mutation-harboring normal tissues (like their neoplastic counterparts), by virtue of their apparent possession of cancer-predisposing alterations, to display histopathological evidence of "overgrowth"—a prediction not supported by the evidence. Such seemingly enigmatic findings, however, are consistent with the OSES model wherein such genomic alterations present in embryonic progenitor cells are passed on to adult stem cells but do not endow a selective advantage, as would be expected by conventional models, but rather predispose to aberrant differentiation of non-stem cells within a stem cell milieu thereby predisposing to subsequent symmetric stem cell mitoses. By this model, in its initial stages, symmetrically-dividing stem cells may not be histologically detectable since their cancer cell progeny are differentiating in a relatively orderly manner—however, such a lesion would be detectable by OSES-derived methods designed to detect symmetrically-dividing stem cells.

Accordingly, early detection methods arising from the OSES model should allow assessment of a cancer prophecy at an early age, at birth, or even possibly in utero. Detecting cancer this early would of course not be possible according to the conventional cancer model which is predicated upon the notion that cancer involves a series of gradual and cumulative cellular derangements occurring after tissue morphogenesis (i.e., later in life). Of course, most tumors will not be detectable this early even by the OSES method, as most tumors will not be initiated until adulthood as a result of somatic disruption (rather than early developmental disruption) of a stem cell milieu. However, adult-onset tumors will also, for similar reasons, be detectable much earlier by OSES-derived methods than by conventional means.

Such an OSES-based method for early cancer detection can be used in patients at risk for developing cancer (e.g., because of family history or environmental risks, such as job hazards or smoking) or in patients in clinical remission from cancer. In addition, perfection of such techniques could lead to their widespread utility in routine cancer screening of the asymptomatic patient.

The invention encompasses an in vivo or in vitro method of cancer diagnosis which comprises assaying for the presence or absence of a slow-growing relatively mutationally-spared cancer stemline, and diagnosing cancer based on the presence of said cancer stemline. In certain embodiments, said detection is effected using a ligand which binds to a cancer stemline-specific surface antigen. In certain embodiments, said ligand contains a detectable moiety. In certain embodiments, the detectable moiety is a fluorescent or radionuclide label. In certain embodiments, said ligand is a monoclonal antibody, cofactor which binds to a cancer stemline-specific entity, or is a constructed non-cleaving factor which binds specifically to a cancer stemline-specific intracellular factor.

In order to better illustrate preferred embodiments of the invention, Table 1, Table 2 and Table 3 are provided below which respectively identify gene products involved in asymmetric mitotic pathway stem cell markers (SCM's), and asymmetrically acting proteins, RNAs and DNAs. These list are meant to be exemplary and not exhaustive of genes that may be targeted according to the invention. Other gene targets have been identified previously, e.g. in section II, subsection 2) of the subject application.

TABLE 1

Gene Products Involved In Asymmetric Mitotic Pathway a) Factors involved in structural asymmetry:

notch (mammal) - provides inherent cellular asymmetry via localization at basolateral surface.
m-numb (mammal) - homolog of *Drosophila* numb which is a membrane associated protein asymmetrically segregated into daughter neuroblast
PTC (mammal) - transmembrane protein, represses Wnt, hh, TGF-beta
frizzled (*Drosophila*) - Wnt receptor
smoothened (*Drosophila*) - Hedgehog receptor
insecutable (*Drosophila*) - cytoskeletal binding protein, asymmetrically segregated in neuron development
prospero (*Drosophila*) - involved in asymmetric mitosis
Gip-1 (nematode) - cell surface receptor involved in asymmetric determination of cell fate
par-1, par-2, par-3, lin-17, and unc-73 (nematode) - asymmetric determination of daughter cell fate
skn-1 (nematode) - asymmetric determination of daughter cell fate
cdc24 (yeast) - involved in asymmetric mitosis
cdc42 (yeast) - membrane G-protein at previous bud site, asymmetrically segregated to one daughter cell (has nematode and human homologs)

b) Downstream transcription factors effecting asymmetric mitosis:

Isl-1 (mammal) - asymmetric determination of Islet of Langerhans cell v.s. tubule stem cell in pancreas
TTK (*Drosophila*) - downstream of numb
Unc-86 (nematode) - equally distributed in both daughter cells, turns on mec-3
lin-11 (nematode) - asymmetric determination of vulva epithelium v.s hypodermis
Sw15 (yeast) - equally distributed in both daughter cells, turns on HO gene.
Ash-1p (yeast) - inhibits HO gene c) Factors ultimately responsible for asymmetrically-defining cell type (expressed in 1 of 2 daughter cells):

En (*Drosophila*) - homeobox transcription factor
mec-3 (nematode) - transcription factor effecting neuron differentiation.
HO (yeast) - encodes endonuclease, mediates mating type recombination event[1].

[1]The yeast pheromone response pathway may also include gene products (e.g., cdc28, kar1) whose human homologs are involved in the asymmetric mitotic pathway of stem cells.)

Such genes are described in the following references: Hirsch et al, "Pheromone response in yeast", *Bioessays*, 14:367-373 (1992); Herman et al, "The *Caenorhabditis elegans* gene lin-44 controls the polarity of asymmetric cell divisions", *Development,* 120:1035-1047 (1994); Johnson et al, "Human Homolog of patched, a Candidate Gene for the Basal Cell Nevus Syndrome", *Science,* 272:1668-1671 (1996); Way et al, "Cell polarity and the mechanism of asymmetric cell division", *Bioessays,* 16:925-931 (1994); Lin et al, "Neuroblasts: a model for the asymmetric division of stem cells", *Trends Genet.,* 13:33-39 (1997), Perrimon, "Serpentine Proteins Slither into the Wingless and Hedgehog Fields", *Cell,* 86:513-516 (1996), Kuhl et al, "Wnt signalling goes nuclear", *Bioessays,* 19:101-104 (1997); Bowerman et al "The maternal gene skn-1 encodes a protein that is distributed unequally in early *C. elegans* embryos", *Cell,* 74:443-452 (1993)).

TABLE 2

Stem Cell Markers (SCM's)

| Tissue Type | Stem Cell Markers (SCM's) | Reference |
|---|---|---|
| Blood | | |
| hematopoietic stem cell | CD34, Scl/Tal-1, Flk-1/KDR, Tie-1, Tie-2, c-Kit, AC133 | 1, 2, 19, 20 |
| myeloid precursor | PU.1 | 1 |
| lymphoid precursor | ikaros | 1 |
| Skin | | |
| basal stem cell | beta-a alpha 2,3,5 integrin, cytokeratin19 | 3 |
| | basonuclin, skin 1a-i/Epoc-1/ Oct 11, LEF-1 | 4 |
| Lung | | |
| basal stem cell | cytokeratin 14 | 5 |
| type II pneumocyte | SP-1, SP-2, EGF-R | 5 |
| | MUC-1 | 6 |
| Liver, Pancreas | | |
| hepatic (oval) stem cell | cytokeratin 14, c-Kit, CF | 7 |
| | Ag's 270, 38, 374, 3, 18, 11, | 8 |
| | AFP, IGF-2, TGF-alpha/beta, GGT | 8 |
| Pancreatic stem cell | lsl-1, FA-1 | 9, 10 |
| Gonads | | |
| primordial germ cell | TRA-1-60, SSEA-1,3,4 | 11, 12 |
| GI tract | | |
| intestinal crypt stem cell | BCL-2 | 13 |
| Breast | | |
| mammary stem cell | Muc-1, ESA | 14 |
| Prostate | | |
| basal prostatic stem cell | HMWCk (5, 14), pp32, CD44 | 15, 16 |
| CNS | | |
| neural stem cells | notch, numb, nestin, p75 | 17, 18 |

References for Table 2:
1. Robb et al, The Scl/Tal1 genes: roles in normal and malignant haematopoiesis, *Bioessays*, 19: 607-612 (1997).
2. Robb et al, The hemangioblast - an elusive cell captured in culture, *Bioessays*, 20: 611-614 (1998).
3. Watt, Epidermal stem cells: markers, patterning and the control of stem cell fate, *Phil. Trans. Soc. Lond. B*, 353: 831-837 (1998).
4. Byrne, Regulation of gene expression in developing epidermal epithelial, *Bioessays*, 19: 691-698 (1997).
5. Otto, Lung stem cells, *Int. J. Exp. Path.*, 78: 291-310 (1997).
6. Jarrad et al, MUC1 is a novel marker for the type II pneumocyte lineage during lung carcinogenesis, *Cancer Res.*, 58: 5582-5589 (1998).
7. Allison et al, Liver stem cells: when the going gets tough they get going, *Int. J. Exp. Path.*, 78: 365-381 (1997).
8. Sigal et al, The liver as a stem cell and lineage system, *Am. J. Physiol.*, 26: G139-G148 (1992).
9. Way et al, Cell polarity and the mechanism of asymmetric cell division, *Bioessays*, 16: 925-931 (1994).
10. Tornehave et al, FA1 immunoreactivity in endocrine tumors and during development of human fetal pancreas; negative correlation with glucagon expression, *Histochem. Cell Biol.*, 106: 535-542 (1996).
11. Andrews, Teratocarcinomas and human embryology: Pluripotent human EC cell lines, *APMIS*, 106: 158-168 (1998).
12. Shamblott et al, Derivation of pluripotent stem cells from cultured human primordial germ cells, *Proc. Natl. Acad. Sci. USA*, 95: 13726-13731 (1998).
13. Potten et al, The intestinal epithelial stem cell: the mucosal governor, *Int. J. Exp. Path.*, 78: 219-243 (1997).
14. Eaves et al, Phenotypic and functional characterization in vitro of a multipotent epithelial cell present in the normal adult human breast, *Differentiation*, 63: 201-13 (1998).
15. Foster et al, Stem cells in prostatic epithelial, *Int. J. Exp. Path.*, 78: 311-329 (1997).
16. Bui, M., et al, Stem cell genes in androgen-independent prostate cancer, *Cancer Metast. Rev.*, 17: 391-399 (1999).
17. Lin et al, Neuroblasts: a model for the asymmetric division of stem cells, 13: 33-39 (1997).
18. Anderson, D. J., et al, Cell lineage determination and the control of neuronal identity in the neural crest, *CSHSQB*, 62: 493-504 (1997).
19. Ziegler, B. L., et al, KDR receptor: A key marker defining hematopoietic stem cells, *Science*, 285: 1553-1558 (1999).
20. Yin, A. H., et al AC133, a novel marker for human hematopoietic stem and progenitor cells, *Blood*, 90: 5002-5012 (1997).

TABLE 3

| | References |
|---|---|
| Asymmetrically-Acting Proteins | |
| Notch 1-4** | 1, 2 |
| Pit-1, p78, lsl-1, mPAR-1, MARK | 3-7 |
| TFIIIA, Y-box proteins | 8 |
| piwi/hiwi/elF2C/prg-1/rde-1 homolog** | 9, 10 |
| mut-7-homolog | 11 |
| X-linked modifiers of HD, PWS | 12-15 |
| glycipan-3 (X-linked modifier of IGF2) | 16 |
| m-Numb, HASH-1/2, dHAND, BC1 | 17-19 |
| Tan-1, SCL, Oct-2, spectrosome | 20-22 |
| hnRNP's (e.g., hnRNP1, A2), snRNP's (e.g., U1-snRNP**) | 8, 23 |
| POMp75, POMp100 | 24 |
| Myo-D, Myf (1, 5) | 25 |
| Asymmetrically-acting RNA and/or DNA endogenous sense RNA's: | |
| H19 | 26 |
| SNRPN, 1PW, PAR (1, 5 SN), ASR (1, 2), BD | 27-29 |
| ZNF127 (homology with RNP's) | 30 |
| aminoacyl tRNA's | 43 |
| endogenous anti-sense RNA's: | |
| H19, IGF2, IGF2R, KvLQT1 | 31-33 |
| ZNF127AS, UBE3A | 30, 34 |
| other interacting RNA and/or DNA: | |
| Ins2 | 35 |
| U2af (homology with U2-snRNP) | 39, 36 |
| X-linked modifier of X transmission | 37 |
| loci 3q21, 3q26, 4qter, 16p13, 16q22 | 38, 39 |
| loci 15p (and centromere), 1 (centromere) | 40, 41 |
| DNA pairing activity: | |
| HPP-1, polypeptides (100 & 75 kDa) | 42 |
| U1-snRNP** | 23 |
| POMp75, POMp100 | 24 |

References for Table 3
1. Lendahl, U. A growing family of Notch ligands, *Bioessays*, 20: 103-107 (1998).
2. Artavanis-Tsakonas, S., et al, Notch signaling: Cell fate control and signal integration in development, *Science*, 284: 770-776 (1999).
3. Hall, P. A., et al, Stem cells: the generation and maintenance of cellular diversity, *Development*, 106: 619-633 (1989).
4. Guo, S., et al, par-1, a gene required for establishing polarity in *C. elegans* embryos, encodes a putative Ser/Thr kinase that is asymmetrically distributed, *Cell*, 19: 611-620 (1995).
5. Parsa, I. Loss of a Mr 78,000 marker in chemically induced transplantable carcinomas and primary carcinoma of the pancreas, *Cancer Res.*, 48: 2265-2272 (1988).
6. Way et al, Cell polarity and the mechanism of asymmetric cell division, *Bioessays*, 16: 925-931 (1994).
7. Jan, Y. N., et al, Asymmetric cell division, *Nature*, 392: 775-778 (1998).
8. Ladomery, M. Multifunctional proteins suggest connection transcriptional and post-transcriptional processes, *Bioessays*, 19: 903-909 (1997).
9. Benfey, P. N., Stem cells: A tale of two kingdoms, *Curr. Biol.*, 9: R171-R172 (1999).
10. Tabara, H., et al, The rde-1 gene, RNA interference, and transposon silencing in *C. elegans*, *Cell*, 99: 123-132 (1999).
11. Ketting, R. F., et al, mut-7 of *C. elegans*, required for transposon silencing and RNA interference, is a homolog of Werner Syndrome helicase and RNaseD, *Cell*, 99: 133-141 (1999).
12. Sabl, J. F., et al, Epigene conversion: A proposal with implications for gene mapping in humans, *Am. J. Hum. Genet.*, 50: 1171-1177 (1992).
13. Laird, C. Proposed genetic basis of Huntington Æs disease ô, *Trends Genet.*, 6: 242-247 (1990).
14. Singh, P. B., et al, A sequence motif found in a *Drosophila* heterochromatin protein is conserved in animals and plants, *Nucleic Acids Res.*, 19: 789-794 (1991).
15. Nicholls, R. D. Inciminating gene suspects, Prader-Willi style ô, *Nature Genet.*, 23: 132-134 (1999).
16. Hastie, N. Disomy and disease resolved, *Nature*, 389: 785-786 (1997).
17. Zhong, W. Asymmetric localization of a mammalian Numb homolog during mouse cortical neurogenesis, *Neuron*, 17: 43-53 (1996).
18. Gestblom, C., et al, The basic helix-loop-helix transcription factor dHAND, a marker gene for the developing human sympathetic nervous system, is expressed in both high- and low-stage neuroblastomas, *Lab. Invest.*, 79: 67-79 (1999).
19. Miyamoto, T., et al, A SacII polymorphism in the human ASCL2 (HASH2) gene region, *J. Hum. Genet.*, 43: 69-70 (1998).
20. Ellisen, L. W. TAN-1, the human homolog of the *Drosophila* Notch gene, is broken by chromosomal translocations in T lymphoblastic neoplasms, *Cell*, 66: 649-661 (1991).
21. Robb, L., et al, The SCL/TAL1 gene: roles in normal and malignant hematopoiesis, *Bioessays*, 19: 607-613 (1997).
22. Robb, L., et al, The hemangioblast - an elusive cell captured in culture, *Bioessays*, 20: 611-614 (1998).
23. Dowjat, K. Anti-(U1)snRNP autoantibodies inhibit homologous pairing activity of the human recombination complex, *DNA Cell Biol.*, 16: 819-827 (1997).
24. Bertrand, P. Human POMp75 is identified as the pro-oncoprotein TLS/FUS: both POMp75 and POMp100 DNA homologous pairing activities are associated to cell proliferation, *Oncogene*, 18: 4515-4521 (1999).
25. Braun, T., et al, Myf-5 and myoD genes are activated in distinct mesenchymal stem cells and determine different skeletal muscle cell lineage, *EMBO J*, 15: 10-18 (1996).

TABLE 3-continued

References

26. Schmidt; J. V. et al, Enhancer competition between H19 and Igf2 does not mediate their imprinting, *Proc. Natl. Acad. Sci. USA*, 96: 9733-9738 (1999).
27. Dittrich, B., et al, Imprint switching on human chromosome 15 may involve alternative transcripts of the SNRPN gene, *Nat. Genet.*, 14: 163-170 (1996).
28. Barlow, D. Competition - a common motif for the imprinting mechanism, *EMBO J.*, 16: 6899-6905 (1997).
29. Kelsey, G., et al, Imprint switch mechanism indicated by mutations in Prader-Willi and Angelman syndromes, *Bioessays*, 19: 361-365 (1997).
30. Jong, M. T. C., et al, A novel imprinted gene, encoding a RING zinc-finger protein, and overlapping antisense transcript in the Prader-Willi syndrome critical region, *Hum. Molec. Genet.*, 8: 783-793 (1999).
31. Moore, T., et al, Multiple imprinted sense and anti-sense transcripts, differential methylation and tandem repeats in putative imprinting control region upstream of mouse Igf2, *Proc. Natl. Acad. Sci. USA*, 94: 12509-12514 (1997).
32. Wutz, A., et al, Imprinted expression of the Igf2r gene depends on an intronic CpG island, *Nature*, 389: 745-749 (1997).
33. Smilinich, N. J., et al, A maternally methylated CpG island in KvLQT1 is associated with an antisense paternal transcript and loss of imprinting in Beckwith-Wiedemann syndrome, *Proc. Natl. Acad. Sci. USA*, 96: 8064-8069 (1999).
34. Rougelle, C., et al, An imprinted antisense RNA overlaps UBE3A and a second maternally expressed transcript, *Nat. Genet.*, 19: 15-16 (1998).
35. Duvillie, B., et al, Imprinting at the mouse Ins2 locus: evidence for cis- and trans-allelic interactions, *Genomics*, 47: 52-57 (1998).
36. Feil, R., et al, Parental chromosome-specific chromatin conformation in the imprinted U2afl-rs1 gene in the mouse, *J. Biol. Chem.*, 272: 20893-20900 (1997).
37. Naumova, A. K., et al, Parental origin-dependent male offspring-specific transmission ratio distortion at loci on the human X chromosome. *Am. J. Hum. Genet.*, 62: 1493-1499 (1998).
38. Tartof, K. D., et al, Trans-sensing effects from *Drosophila* to humans, *Cell*, 65: 201-203 (1991).
39. Stout, K., et al, Somatic pairing between subtelomeric chromosomal regions: implications for human genetic disease, *Chrom. Res.*, 7: 323-329 (1999).
40. Lewis, J. P., et al, Somatic pairing of centromeres and short arms of chromosome 15 in the hematopoietic and lymphoid system, *Hum. Genet.*, 92: 577-582 (1993).
41. Arnoldus, P. J., et al, Somatic pairing of chromosome 1 centromeres in interphase nuclei of human cerebellum, *Hum. Genet.*, 83: 231-234 (1989).
42. Akhmedov, A. T., et al, Characterization of two nuclear mammalian homologous DNA-pairing activities that do not require associated exonuclease activity, *Proc. Natl. Acad. Sci. USA*, 92: 1729-1733 (1995).
43. Jansen, R.-P. RNA - cytoskeletal associations, *FASEB J.*, 13: 455-466 (1999).

Summary

I. Gene Targets that are Identified in the Present Invention

With regard to Section I of Novel Therapies Provided by the Invention pertaining to immunotherapy direct at stem cell antigens, there are indeed a number of published stem cell antigens. Specifically, stem cell antigens (a.k.a. stem cell markers, a.k.a. cancer stem line-specific markers) are known for a number of tissue types (see Table 2) and are available as potential targets for therapy. This list (Table 2) is not meant to be exhaustive, but merely exemplary of stem cell antigens that may be targeted in the subject therapies.

With regard to Section II of Novel Therapies Provided by the Invention pertaining to induction of a switch from symmetric to asymmetric cancer stem line mitosis, there have been a number of published molecules involved in this switch. Specifically, stem cell-specific (or, cancer stem line-specific) molecules involved in the symmetric asymmetric mitotic switch are known for a number of tissue types (see, e.g., Table 1 and Table 3 and targets identified in Section II) and are available as potential targets for therapy. Those targets listed in Table 1 and Table 3, as well as targets identified in Section II are also meant to be exemplary and not exhaustive of potential targets that may be targeted in this aspect of the invention. Since, as described in Section II, the therapeutic goal of this aspect of the invention is to force a cancer stem line from symmetric to asymmetric mitosis, these targets (listed in Table-1, Table 2, and Section II of the specification) causing this switch would require therapeutic activation whereas those targets inhibiting this switch will require therapeutic blockage. It should be noted that depending on the tissue type and cellular context some of the listed targets can at times cause (and at other times inhibit) asymmetric mitosis—thus all asymmetrically-acting species in general (whether seemingly causing or inhibiting asymmetric mitosis) should be considered potential targets for therapy and have been listed as such.

With regard to Section III of Novel Therapies Provided by the Invention pertaining to eradication of a cancer stem line via its induction to symmetrically differentiate, again there have been a number of published cancer stem line-specific molecules involved in this induction. Specifically, as mentioned supra, stem cell-specific (or, cancer stem line-specific) molecules involved in the symmetric-asymmetric mitotic switch are known for a number of tissue types (see Table 3 and Section II) and are available as potential targets for therapy. Those targets listed in Table 3 are again to be considered exemplary and supplementary to those identified Table-1 and Section II of the subject application. However as described for the methods of Section III, and in contradistinction to the methods of Section II, the therapeutic goal here is not to force asymmetric mitosis but rather to maintain a cancer stem line in symmetric mitosis. Such methodology requires the opposite of what is described in Section II. In other words, those targets causing a switch to asymmetric mitosis would require therapeutic blockage while those targets inhibiting this switch would require therapeutic activation. Again, since there is variability as to the causative versus inhibitory actions (with respect to induction of asymmetric mitosis) by the listed targets, depending on the tissue type and cellular context, it is likely that one target may be causative in one context (and thus worthy of activation by the methods described in Section II) while inhibitory in another context (and thus also worthy of activation by the methods described in Section III).

It should be noted that the molecules/gene products listed in Table 3 (as well as in Table 1 and Section II) can be generally characterized as species of protein, ribo-protein, RNA, and DNA which are asymmetrically-acting—and it is this peculiar asymmetrically-acting quality that makes these cancer stem line-specific molecular species such good targets. More specifically, what is meant by asymmetrically-acting is that such molecular species cause asymmetric mitosis and do so because they function as:

1) proteins or riboprotein complexes that
i) unequally segregate to one or another daughter cell (e.g., Notch, Numb, p78) thereby causing differences in cell fate
ii) effect unequal segregation not of themselves but of RNA's to daughter cells
iii) unequally effect the outcome of RNA:RNA interactions (e.g. RNP's, mut-7)
iv) unequally effect the outcome of DNA:DNA interactions (e.g. POM's)
v) unequally effect the fate of daughter of cells via other mechanisms (e.g., piwi, X-linked modifiers)
2) RNA's that
i) unequally effect (imprinted) allele expression (e.g., H19, SNRPN)
ii) act as endogenous anti-sense RNA's to unequally effect (imprinted) allele expression (e.g., UBE3A)
iii) unequally effect the outcome of DNA:DNA interactions (e.g., RNP's) 3) DNA's that i) are themselves involved in unequal interallelic pairing (e.g., 11p15, 15q11-13).

Accordingly, forcing a cancer stem line to switch to an asymmetric mitotic phase (i.e., see next section regarding the goal of Section II) can be accomplished by either therapeutically activating unequally-acting targets (e.g., those listed in Table 1 and Table 3), or by therapeutically blocking the inhibitors of unequally-acting targets (e.g. those listed in Table 1, and Table 3). Alternatively, forcing a cancer stem line to remain in a symmetric mitotic phase (see next section regarding the goal of Section III) can be accomplished by either blocking unequally-acting targets, or by activating inhibitors of unequally-acting targets.

II. Updated Use/Design/Construction of Novel Therapeutics

With regard to Section I of Novel Therapies Provided by the Invention pertaining to immunotherapy directed at stem cell antigens, there is indeed available a number of monoclonal antibodies specific to stem cell markers (a.k.a. cancer stem line markers). For example, monoclonal antibodies specific to hematopoietic stem cell markers (i.e., monoclonal antibody to Flk-1/KDR), and to lung stem cell markers (i.e., monoclonal antibody to SP-A) have been well-described (ref.'s 1-4). Also, therapeutic efficacy has been demonstrated, e.g. in the case of monoclonal antibodies to the hematopoietic stem cell marker Flk-1/KDR, albeit in a slightly different context (i.e., as an anti-angiogenic) (ref. 2). Considering that the methods of construction of monoclonal antibodies are well-known by those skilled in the art, additional monoclonal antibodies specific to the known cancer stem line-specific targets (listed in Table 2) can be readily made (with or without attached therapeutic, e.g. radionuclide, moieties, as described in Section I) and tested for therapeutic efficacy.

With regard to Section II of Novel Therapies Provided by the Invention pertaining to induction of a switch from symmetric to asymmetric cancer stem line mitosis, there is indeed available a number of (DNA-, RNA-, antibody, protein, and other molecularly-based) therapeutics that can target and dysregulate cancer stem line-specific asymmetrically-acting molecular species (e.g., those molecular species list in Table 1, Table 3 and Section II that determine the mitotic phase—i.e., asymmetric versus symmetric). For example, as previously mentioned in Section II:

1) DNA-based therapeutics (i.e., gene therapy) can be used to activate genes that cause asymmetric mitosis—thereby causing a cancer stem line to switch from symmetric to asymmetric mitosis. Alternatively, DNA-based therapeutics (i.e., gene therapy) can be used to activate genes that block the inhibition of asymmetric mitosis—thereby causing a cancer stem line to switch from symmetric to asymmetric mitosis.

2) RNA-based therapeutics (e.g., antisense or ribozyme therapy) can be used to block expression of gene products that inhibit asymmetric mitosis—thereby causing a cancer stem line to switch from symmetric to asymmetric mitosis.

Indeed, working published examples of this are the use of custom-designed antisense RNA to specifically inhibit asymmetrically-acting piwi homologs (ref. 5), and to inhibit asymmetric RNP action (ref. 6), in both cases resulting in significant cell fate changes (ref.'s 5, 6). Also, since portions of the 3'UTR (untranslated region) of some RNA's are largely responsible for the asymmetric action of such RNA's, coupled with the data that these 3'UTR portions contain well-conserved motifs—antisense/ribozyme therapeutics can be readily constructed, by those skilled in the art, to these motifs so as to inhibit in a general way the unequal action of asymmetrically-acting RNA species—as has been described (ref. 6).

Also not previously mentioned in Section II, but presented here is an updated version of additional therapeutics (i.e. in addition to those DNA- and RNA-based is therapies mentioned):

3) RNA-based therapeutics which use endogenous asymmetrically-acting sense RNA species (e.g., H19, SNRPN) to either activate or block the inhibition of asymmetric mitosis—thereby causing a cancer stem line to switch from symmetric to asymmetric mitosis.

4) RNA-based therapeutics which use endogenous asymmetrically-acting antisense RNA species (e.g., ZNF127AS, UBE3A) to either activate or block the inhibition of asymmetric mitosis—thereby causing a cancer stem line to switch from symmetric to asymmetric mitosis.

5) Antibody-based therapeutics which block molecular species that normally inhibit asymmetric mitosis—thereby causing a cancer stem line to switch from symmetric to asymmetric mitosis.

Indeed, a working published example of this is the use of antibodies to U1-snRNP to inhibit inter-allelic interactions occurring via DNA:DNA interactions (ref. 9).

6) Protein-based therapeutics which use either endogenous or constructed protein species to either cause asymmetric mitosis or block inhibition of asymmetric mitosis—thereby causing a cancer stem line to switch from symmetric to asymmetric mitosis. For example, certain endogenous inhibitors of Notch (e.g., notch-less) could be used to change the mitotic phase of a cancer stem line (i.e., from symmetric to asymmetric mitosis) (ref.'s 7, 8).

Moreover and more generally, since the asymmetric action of certain asymmetrically-acting proteins can be traced to their RNA-binding action, coupled with the data that RNA-binding is due to certain well-conserved protein motifs (e.g., DEAH, or KH protein domains) (ref. 6), peptide mimics can be readily constructed by those skilled in the art (e.g., as described for farnesyl transferase inhibitor protein-based therapeutics, see ref. 21) for the purpose of therapeutically competing with (i.e., inhibiting) endogenous asymmetrically-acting protein species thereby forcing a cancer stem line to assume an asymmetric mitotic phase. Also, like in the case of farnesyl transferase inhibitor peptides (ref. 21), readily enabled screening assays can be constructed, by those skilled in the art, to search for improved (in this case, anti-symmetric mitosis) compounds of protein or other molecular species make-up.

Techniques for more efficient in vivo delivery of RNA-based therapeutics have been described (e.g., construction of exonuclease-resistant RNA species) (ref. 23), as have techniques for more efficient in vivo delivery of protein-based therapeutics (e.g., lipophilic or peptidase-resistant protein species) (ref.'s 21, 22). Continued technical improvements of this sort will enable more efficient in vivo delivery of the novel therapeutics described in this application.

In addition to those specific published working examples cited above that support the idea that asymmetric mitosis can be therapeutically-induced via delivery of certain DNA-, RNA-, antibody-, and protein-based compounds (e.g. as mentioned, in the cases of antisense RNA to asymmetrically-acting piwi homologs and RNP-related complexes, as well as antibodies to RNA's), a number of more generally-acting compounds have also been shown to adversely effect the mitotic machinery. These include cytoskeletal inhibitors (e.g., colcemid, colchicine, cytochalasin D, latrunculin A, arsenic and other heavy metals, taxanes, monastrol) which while not very specific with regard to their molecular targets (as compared to novel DNA-, RNA-, antibody-, and protein-based therapeutics) do still show well-described anti-cancer activity—albeit with associated toxicities attributable to their lack of target specificity. Thus these compounds serve as good controls for which to compare newer more specific therapeutic inhibitors of symmetric mitosis.

Also, a number of generally-acting differentiation/starvation-inducing compounds are known to have anti-cancer activity through their action on the differentiation/asymmetric mitosis pathway—some of these compounds include, but are not exclusive to, retinoic acid, enzymes involved in nucleic acid (DNA or RNA) synthesis, protein synthesis, the removal of essential growth factors, the use of drugs, or the use of chalones that induce a cellular starvation response, histone deacetylase inhibitors (e.g. trichostatin), sodium phenylbutyrate, sodium phenylacetate, DMSO, HMBA, PMA, tetramethyl urea, amino acid analogs (e.g., AzC, 6MMPR, L-alanosine, PALA), inosine, monophosphate dehydrogenase inhibitors (e.g., mycophenolic acid), methotrexate, rRNA inhibitors (e.g., heparin, synthetic peptide substrate of casein kinase II, actinomycin D, puromycin aminonucleoside, DRB, H1o histone), inhibitors of charging tRNA or protein translation (e.g., histidinol, EIF46 cleavage), guanine nucleotide inhibitors (e.g., virazole, 6-chloropurine), and differentiation-inducing ligands/receptor pathway components (e.g., Wnt/frizzled and downstream components, Hedgehog/Patched and downstream components, Notch/Delta/Serrate and downstream components). It should be noted that these compounds can effect both differentiation/starvation as well as more downstream events involving the asymmetric mitotic machinery—thus can also (like the mentioned cytoskeletal inhibitors) serve as good controls for which to compare newer more specific therapeutic inhibitors of symmetric mitosis.

With regard to section III of Novel Therapies Provided by the Invention pertaining to induction of symmetric differentiation in the cancer stem line, i.e., by 1) inhibition of asymmetric cancer stem line mitosis, followed by 2) induction of cancer stem line differentiation) there is indeed available as mentioned a number of (DNA-, RNA-, antibody-, and protein-based) therapeutics that can target cancer stem line-specific asymmetrically-acting molecular species are listed in Table 1, and Table 3 and Section II of this application). Also to be included as therapeutics that alter the mitotic program and/or differentiation/starvation state of a cancer stem line are the previously mentioned cytoskeletal inhibitors (e.g., colcemid, et al) and differentiation/starvation inducers (e.g., retinoic acid, et al). It should be noted that the differentiation/starvation inducers (e.g., retinoic acid, et al) may have overlapping roles as both 1) dysregulator of mitosis, and 2) inducer of differentiation, and thus some of these compounds may be used for both of these processes.

It should also be aptly noted that, unlike for Section II where the therapeutic goal is to induce asymmetric mitosis (e.g., by either activating factors that cause asymmetric mitosis, or blocking factors that inhibit asymmetric mitosis), the therapeutic goal of Section III is the opposite—i.e., to either block factors that cause a switch from symmetric to asymmetric mitosis, or activate factors that inhibit asymmetric mitosis. In this way (i.e., the therapeutic goal outlined in Section III):

1) a cancer stem line will be forced to assume a symmetric mitotic program (versus the therapeutic goal outlined in Section II which is to force a cancer stem line to assume an asymmetric mitotic program). This can be accomplished crudely by cytoskeletal inhibitors (e.g., colcemid, et al) and differentiation/starvation inducers (e.g., retinoic acid, et al), or specifically by the described novel DNA-, RNA-, antibody-, protein, and other molecularly-based therapies.

2) after the cancer stem line is induced to remain in a symmetric mitotic program, the final therapeutic goal (as outlined in Section III) is to cause it to undergo a differentiation/starvation program—which will be symmetric in nature since the cancer stem line has been therapeutically frozen in a symmetric mitotic program. This can be accomplished most efficiently by differentiation/starvation inducers (e.g., retinoic acid, et al), but may also be effected by cytoskeletal inhibitors (e.g., colcemid, et al) or the described novel DNA-, RNA-, antibody-, protein, and other molecularly-based therapies.

There are indeed data supportive of these ideas. Namely, as outlined in Section III, the therapeutic goal is a two-step one: 1) inhibit (cancer stem line) asymmetric mitosis, and then 2) induce (cancer stem line) differentiation. There are indeed published examples, albeit preliminary, of a related 2-step therapeutic design whereby cancer cells are 1) affected at the level of their mitotic machinery, and 2) affected via differentiation/starvation. These examples provide scientific evidence in support of the premise of the efficacy of the therapeutic methods of the invention. For example, cancer cells have been shown to respond to the following therapeutic combinations:

| Agent effecting mitotic phase | Agent effecting differentiation/starvation | Therapeutic Effect | Reference |
|---|---|---|---|
| Arsenic | retinoic acid | differentiation and apoptosis | 10 |
| Arsenic | GM-CSF | differentiation | 11 |
| activation c-myc | sodium phenylbutyrate | apoptosis | 20 |
| activation c-myc | serum starvation | apoptosis | 12 |
| activation c-myc | p53 | apoptosis | 13 |
| inhibition GTP-tubulin | p53 | differentiation | 14, 15 |
| E7 | HMBA | apoptosis | 16 |
| p130 (Rb-like) | cytokine-deprivation | differentiation | 17 |
| loss of Rb | mitogen-deprivation | apoptosis | 18 |
| loss senescence | serum deprivation | apoptosis | 19 |

That c-myc activates apoptosis in the context of a cellular conflict (i.e. opposing signals of mitosis and differentiation/starvation) is indeed an increasingly well-appreciated concept, and was a topic of a recent review (ref. 24).

Accordingly, these systems which have been already been shown capable of differentiation/apoptosis (in response to relatively crude methods), can serve as controls for which to test (and optimize) the novel DNA-, RNA-, antibody-, protein-, and other molecularly-based therapies described in this application.

REFERENCES CITED IN SUMMARY

1. Ziegler, B. L., et al, "KDR receptor: A key marker defining hematopoietic stem cells," *Science*, 285: 1553-1558 (1999).
2. Witte, L., et al, "Monoclonal antibodies targeting the VEGF receptor-2 (Flk1/KDR) as an anti-angiogenic therapeutic strategy," *Cancer Metast. Rev.*, 17: 155-161 (1998).
3. Ten Have-Opbroek, A. A. W., et al, "The alveolar type II cell is a pluripotential stem cell in the genesis of human adenocarcinomas and squamous cell carcinomas", *Histol. Histopathol.*, 12: 319-336 (1997).
4. SP-1 monoclonal body is commercially available from Byk Gulden Co. (Lomberg Chemische Fabrik GmbH, D-78467 Konstanz) Germany.
5. Benfey, P. N., "Stem cells: A tale of two kingdoms," *Curr. Biol.*, 9:R171-R172 (1999).
6. King, M. L., et al, "Polarizing genetic information in the egg: RNA localization in the frog oocyte," *Bioessays*, 21: 546-557 (1999).
7. Panin, V. M, et al, "Modulators of Notch signaling," *Semin. Cell Biol.*, 9: 609-617 (1998).
8. Royet, J., et al, "Notchless encodes a novel WD40-repeat-containing protein that modulates Notch signaling activity," *EMBO J.*, 17: 7351-7360 (1998).
9. Dowjat, K. "Anti-(U1)snRNP autoantibodies inhibit homologous pairing activity of the human recombination complex," *DNA Cell Biol.*, 16: 819-827 (1997).
10. Soignet, S. L., et al, "Complete remission after treatment of acute promyelocytic leukemia with arsenic trioxide," *N. Eng. J. Med.*, 339:1341-1348 (1998).

11. Kizaki, M., et al, "Application of heavy metal and cytokine for differentiation-inducing therapy in acute promyelocytic leukemia," *J. Natl. Cancer Inst.,* 90: 1906-1907 (1998).
12. Evan, G. I., et al, "Induction of apoptosis in fibroblasts by c-mycprotein", *Cell,* 69: 119-128 (1992).
13. Hermeking, H., et al, "Mediation of c-myc-induced apoptosis by p53," *Science,* 265: 2091-2093 (1994).
14. Li, Y. M., et al, "Arsenic targets tubulins to induce apoptosis in myeloid leukemia cells", *Cancer Res.,* 59: 776-780 (1999).
15. Sherley, J. L., et al, "δExpression of the wild-type p53 antioncogene induces guanine nucleotide-dependent cell division kinetics", *Proc. Natl. Acad. Sci. USA,* 92: 136-140 (1995).
16. Richon, V. M., et al, "Two cytodifferentiation agent-induced pathways, differentiation and apoptosis, are distinguished by the expression of papillomavirus 16 E7 in human bladder carcinoma cells," *Cancer Res.,* 57:2789-2798 (1997).
17. Mori, A., et al, "Granulocytic differentiation of myeloid progenitor cells by p130, the retinoblastoma tumor suppressor homologue," *Oncogene,* 18: 6209-6221 (1999).
18. Wang, J., et al, "Rb functions to inhibit apoptosis during myocyte differentiation," *Cancer Res.,* 57: 351-354 (1997).
19. Preston, G. A., et al, "Regulation of apoptosis by low serum in cells of different stages of neoplastic progression: enhanced susceptibility after loss of a senescence gene and decreased susceptibility after loss of a tumor suppressor gene," *Cancer Res.,* 54: 4214-4223 (1994).
20. Bernhard, D., et al, "Apoptosis induced by the histone deacetylase inhibitor sodium butyrate in human leukemic lymphoblasts," *FASEB J.,* 13:1991-2001 (1999).
21. Lobell, R. B., et al, "Pre-clinical development of farnesyltransferase inhibitors," *Cancer Metast. Rev.,* 17: 203-210 (1998).
22. Schumacher, T. N. M, et al, "Identification of D-peptide ligands through mirror-image phage display," *Science,* 271: 1854-1857 (1996).
23. Teplova, M., et al, "Structural origins of the exonuclease resistance of a zwitterionic RNA," *Proc. Natl. Acad. Sci. USA,* 96: 14240-14245 (1999).
24. Fuhrmann, G., et al, "The MYC dualism in growth and death," *Mutation Res.,* 437: 205-217 (199).

The invention may be embodied in other specific forms without departing from its spirit or essential characteristics. The described embodiments are to be considered in all respects only as illustrative and not restrictive, and the scope of the invention is, therefore, indicated by the appended claims rather than by the foregoing description. All modifications which come within the meaning and range of the lawful equivalency of the claims are to be embraced within that scope.

What is claimed is:

1. A method for detecting the presence of solid tumor stem cells in a patient having a solid tumor, comprising:
    (a) contacting cells obtained from a solid tumor of the subject with an antibody that binds ESA;
    (b) selecting cells that bind to said antibody; and
    (c) assaying the ability of the cells to regrow a tumor mass; wherein the ability of the cells that bind to said antibody to regrow a tumor mass indicates the presence of solid tumor stem cells in the patient.

2. The method of claim 1, wherein the antibody is attached to a detectable moiety.

3. The method of claim 2, wherein the detectable moiety is a fluorescent tag.

4. The method of claim 2, wherein the detectable moiety is a radionuclide tag.

5. The method of claim 1, wherein the cancer stem cells are colon cancer stem cells, brain cancer stem cells, neural cancer stem cells, breast cancer stem cells, liver cancer stem cells, skin cancer stem cells, gastrointestinal cancer stem cells, pancreatic cancer stem cells, ovarian cancer stem cells, or lung cancer stem cells.

* * * * *